(12) United States Patent
Peled

(10) Patent No.: US 8,846,393 B2
(45) Date of Patent: Sep. 30, 2014

(54) METHODS OF IMPROVING STEM CELL HOMING AND ENGRAFTMENT

(75) Inventor: Tony Peled, Mevasseret Zion (IL)

(73) Assignee: Gamida-Cell Ltd., Jerusalem (IL)

( * ) Notice: Subject to any disclaimer, the term of this patent is extended or adjusted under 35 U.S.C. 154(b) by 1049 days.

(21) Appl. No.: 12/085,406

(22) PCT Filed: Nov. 29, 2006

(86) PCT No.: PCT/IL2006/001381
§ 371 (c)(1),
(2), (4) Date: May 15, 2009

(87) PCT Pub. No.: WO2007/063545
PCT Pub. Date: Jun. 7, 2007

(65) Prior Publication Data
US 2010/0061963 A1     Mar. 11, 2010

Related U.S. Application Data

(63) Continuation-in-part of application No. 11/289,004, filed on Nov. 29, 2005, now abandoned.

(51) Int. Cl.
| | |
|---|---|
| C12N 5/02 | (2006.01) |
| C12N 5/07 | (2010.01) |
| C12N 5/071 | (2010.01) |
| C12N 5/0789 | (2010.01) |
| A61K 35/12 | (2006.01) |

(52) U.S. Cl.
CPC .......... *C12N 5/0647* (2013.01); *C12N 2501/00* (2013.01); *C12N 2501/50* (2013.01); *A61K 2035/124* (2013.01); *C12N 2500/38* (2013.01)
USPC ............................. 435/377; 435/325; 435/372

(58) Field of Classification Search
CPC .......... C61K 2035/124; C12N 5/0647; C12N 2501/00; C12N 2501/50
USPC .......................... 435/377, 325, 372
See application file for complete search history.

(56) References Cited

U.S. PATENT DOCUMENTS

| | | | |
|---|---|---|---|
| 3,687,808 A | 8/1972 | Merigan, Jr. et al. | |
| 3,715,345 A | 2/1973 | Smith | |
| 3,791,932 A | 2/1974 | Schuurs et al. | 195/103.5 |
| 3,839,153 A | 10/1974 | Schuurs et al. | 195/103.5 |
| 3,850,578 A | 11/1974 | McConnell | 23/230 B |
| 3,850,752 A | 11/1974 | Schuurs et al. | 195/103.5 |
| 3,853,987 A | 12/1974 | Dreyer | 424/1 |
| 3,863,008 A | 1/1975 | Grant | |
| 3,867,517 A | 2/1975 | Ling | 424/1 |
| 3,876,623 A | 4/1975 | Jackson et al. | |
| 3,879,262 A | 4/1975 | Schuurs et al. | 195/63 |
| 3,901,654 A | 8/1975 | Gross | 23/230 B |
| 3,935,074 A | 1/1976 | Rubenstein et al. | 195/103.5 |
| 3,984,533 A | 10/1976 | Uzgiris | 424/12 |
| 3,996,345 A | 12/1976 | Ullman et al. | 424/12 |
| 4,034,074 A | 7/1977 | Miles | 424/1 |
| 4,036,945 A | 7/1977 | Haber | |
| 4,098,876 A | 7/1978 | Piasio et al. | 424/1 |
| 4,331,647 A | 5/1982 | Goldenberg | |
| 4,469,863 A | 9/1984 | Ts'o et al. | |
| 4,476,301 A | 10/1984 | Imbach et al. | |
| 4,642,120 A | 2/1987 | Nevo et al. | |
| 4,666,828 A | 5/1987 | Gusella | 435/6 |
| 4,683,202 A | 7/1987 | Mullis | 435/91 |
| 4,687,808 A | 8/1987 | Jarrett et al. | |
| 4,801,531 A | 1/1989 | Frossard | 435/6 |
| 4,806,484 A | 2/1989 | Petrossian et al. | |
| 4,816,567 A | 3/1989 | Cabilly et al. | |
| 4,866,052 A | 9/1989 | Hider et al. | |
| 4,868,116 A | 9/1989 | Morgan et al. | |
| 4,879,219 A | 11/1989 | Wands et al. | 435/7 |
| 4,946,778 A | 8/1990 | Ladner et al. | |
| 4,980,286 A | 12/1990 | Morgan et al. | |
| 5,011,771 A | 4/1991 | Bellet et al. | 435/7.94 |
| 5,013,830 A | 5/1991 | Ohtsuka et al. | |
| 5,023,243 A | 6/1991 | Tullis | |
| 5,034,506 A | 7/1991 | Summerton et al. | |
| 5,081,035 A | 1/1992 | Halberstadt et al. | |
| 5,149,797 A | 9/1992 | Pederson et al. | |
| 5,166,315 A | 11/1992 | Summerton et al. | |
| 5,166,320 A | 11/1992 | Wu et al. | |
| 5,177,196 A | 1/1993 | Meyer, Jr. et al. | |
| 5,185,444 A | 2/1993 | Summerton et al. | |

(Continued)

FOREIGN PATENT DOCUMENTS

| | | |
|---|---|---|
| AU | 759 522 | 8/1999 |
| AU | 770 896 | 6/2000 |

(Continued)

OTHER PUBLICATIONS

Donovan et al., The end of the beginning for pluripotent stem cells. Nature. Nov. 1, 2001;414(6859):92-7. Review.*

(Continued)

*Primary Examiner* — Maria Leavitt
(74) *Attorney, Agent, or Firm* — Ivor R. Elrifi; Matthew Pavao; Cooley LLP

(57) ABSTRACT

A method of enhancing cell engraftment potential is provided. The method comprising ex-vivo or in-vitro subjecting a population of cells to an amount of nicotinamide for a period of time sufficient to effect the population of cells, thereby enhancing cell engraftment potential.

10 Claims, 7 Drawing Sheets

(56) References Cited

U.S. PATENT DOCUMENTS

| | | | |
|---|---|---|---|
| 5,188,897 A | 2/1993 | Suhadolnik et al. | |
| 5,192,659 A | 3/1993 | Simons | 435/6 |
| 5,214,134 A | 5/1993 | Weis et al. | |
| 5,216,141 A | 6/1993 | Benner | |
| 5,220,007 A | 6/1993 | Pederson et al. | |
| 5,235,033 A | 8/1993 | Summerton et al. | |
| 5,256,775 A | 10/1993 | Froehler | |
| 5,264,423 A | 11/1993 | Cohen et al. | |
| 5,264,562 A | 11/1993 | Matteucci | |
| 5,264,564 A | 11/1993 | Matteucci | |
| 5,272,057 A | 12/1993 | Smulson et al. | 435/6 |
| 5,276,019 A | 1/1994 | Cohen et al. | |
| 5,278,302 A | 1/1994 | Caruthers et al. | |
| 5,281,521 A | 1/1994 | Trojanowski et al. | 435/7.5 |
| 5,286,717 A | 2/1994 | Cohen et al. | |
| 5,320,963 A | 6/1994 | Knaack et al. | |
| 5,321,131 A | 6/1994 | Agrawal et al. | |
| 5,342,781 A | 8/1994 | Su | |
| 5,366,878 A | 11/1994 | Pederson et al. | |
| 5,378,725 A | 1/1995 | Bonjouklian et al. | |
| 5,399,676 A | 3/1995 | Froehler | |
| 5,403,711 A | 4/1995 | Walder et al. | |
| 5,405,938 A | 4/1995 | Summerton et al. | |
| 5,405,939 A | 4/1995 | Suhadolnik et al. | |
| 5,434,257 A | 7/1995 | Matteucci et al. | |
| 5,437,994 A | 8/1995 | Emerson et al. | |
| 5,453,496 A | 9/1995 | Caruthers et al. | |
| 5,455,233 A | 10/1995 | Spielvogel et al. | |
| 5,466,677 A | 11/1995 | Baxter et al. | |
| 5,470,967 A | 11/1995 | Huie et al. | |
| 5,476,925 A | 12/1995 | Letsinger et al. | |
| 5,480,906 A | 1/1996 | Creemer et al. | |
| 5,486,359 A | 1/1996 | Caplan et al. | |
| 5,489,677 A | 2/1996 | Sanghvi et al. | |
| 5,491,133 A | 2/1996 | Walder et al. | |
| 5,504,103 A | 4/1996 | Bonjouklian et al. | |
| 5,519,126 A | 5/1996 | Hecht | |
| 5,536,821 A | 7/1996 | Agrawal et al. | |
| 5,539,082 A | 7/1996 | Nielsen et al. | |
| 5,541,306 A | 7/1996 | Agrawal et al. | |
| 5,541,307 A | 7/1996 | Cook et al. | |
| 5,545,806 A | 8/1996 | Lonberg et al. | |
| 5,545,807 A | 8/1996 | Surani et al. | |
| 5,550,111 A | 8/1996 | Suhadolnik et al. | |
| 5,561,225 A | 10/1996 | Maddry et al. | |
| 5,563,253 A | 10/1996 | Agrawal et al. | |
| 5,565,350 A | 10/1996 | Kmiec | |
| 5,569,825 A | 10/1996 | Lonberg et al. | |
| 5,571,799 A | 11/1996 | Tkachuk et al. | |
| 5,587,361 A | 12/1996 | Cook et al. | |
| 5,596,086 A | 1/1997 | Matteucci et al. | |
| 5,602,240 A | 2/1997 | De Mesmaeker et al. | |
| 5,608,046 A | 3/1997 | Cook et al. | |
| 5,610,289 A | 3/1997 | Cook et al. | |
| 5,612,211 A | 3/1997 | Wilson et al. | |
| 5,618,704 A | 4/1997 | Sanghvi et al. | |
| 5,623,065 A | 4/1997 | Cook et al. | |
| 5,623,070 A | 4/1997 | Cook et al. | |
| 5,625,050 A | 4/1997 | Beaton et al. | |
| 5,625,126 A | 4/1997 | Lonberg et al. | |
| 5,631,219 A | 5/1997 | Rosenthal et al. | |
| 5,633,360 A | 5/1997 | Bischofberger et al. | |
| 5,633,425 A | 5/1997 | Lonberg et al. | |
| 5,652,355 A | 7/1997 | Metelev et al. | |
| 5,652,356 A | 7/1997 | Agrawal | |
| 5,654,186 A | 8/1997 | Cerami et al. | |
| 5,661,016 A | 8/1997 | Lonberg et al. | |
| 5,663,312 A | 9/1997 | Chaturvedula | |
| 5,674,750 A | 10/1997 | Kraus et al. | |
| 5,677,437 A | 10/1997 | Teng et al. | |
| 5,677,439 A | 10/1997 | Weis et al. | |
| 5,700,922 A | 12/1997 | Cook | |
| 5,712,154 A | 1/1998 | Mullon et al. | |
| 5,714,331 A | 2/1998 | Buchardt et al. | |
| 5,716,411 A | 2/1998 | Orgill et al. | |
| 5,716,616 A | 2/1998 | Prockop et al. | |
| 5,719,262 A | 2/1998 | Buchardt et al. | |
| 5,733,541 A | 3/1998 | Taichman et al. | |
| 5,736,396 A | 4/1998 | Bruder et al. | |
| 5,741,899 A | 4/1998 | Capon et al. | |
| 5,770,378 A | 6/1998 | Hwang et al. | |
| 5,770,580 A | 6/1998 | Ledley et al. | |
| 5,776,699 A | 7/1998 | Klein et al. | |
| 5,789,245 A | 8/1998 | Dubensky, Jr. et al. | |
| 5,789,543 A | 8/1998 | Ingham et al. | |
| 5,792,751 A | 8/1998 | Ledley et al. | |
| 5,814,482 A | 9/1998 | Dubensky, Jr. et al. | |
| 5,830,760 A | 11/1998 | Tsai et al. | |
| 5,837,544 A | 11/1998 | Capon et al. | |
| 5,843,723 A | 12/1998 | Dubensky, Jr. et al. | |
| 5,844,079 A | 12/1998 | Ingham et al. | |
| 5,851,832 A | 12/1998 | Weiss et al. | |
| 5,851,984 A | 12/1998 | Matthews et al. | |
| 5,877,207 A | 3/1999 | Klein et al. | |
| 5,945,309 A | 8/1999 | Ni et al. | |
| 5,945,337 A | 8/1999 | Brown | |
| 5,952,345 A | 9/1999 | Klein et al. | |
| 5,958,954 A | 9/1999 | Klein et al. | |
| 5,990,329 A | 11/1999 | Klaus et al. | |
| 6,008,204 A | 12/1999 | Klein et al. | |
| 6,015,686 A | 1/2000 | Dubensky, Jr. et al. | |
| 6,015,694 A | 1/2000 | Dubensky, Jr. et al. | |
| 6,063,797 A | 5/2000 | Fesus et al. | |
| 6,077,947 A | 6/2000 | Capon et al. | |
| 6,090,810 A | 7/2000 | Klein et al. | |
| 6,117,850 A | 9/2000 | Patchen et al. | |
| 6,130,230 A | 10/2000 | Chambon et al. | |
| 6,133,309 A | 10/2000 | Bollag et al. | |
| 6,165,747 A | 12/2000 | Ingham et al. | |
| 6,218,128 B1 | 4/2001 | Klein et al. | |
| 6,228,848 B1 | 5/2001 | Klein et al. | |
| 6,232,291 B1 | 5/2001 | Ni et al. | |
| 6,255,112 B1 | 7/2001 | Thiede et al. | |
| 6,261,786 B1 | 7/2001 | Marigo et al. | |
| 6,270,964 B1 | 8/2001 | Michnick et al. | |
| 6,271,363 B1 | 8/2001 | Ingham et al. | |
| 6,284,540 B1 | 9/2001 | Milbrandt et al. | |
| 6,294,330 B1 | 9/2001 | Michnick et al. | |
| 6,303,374 B1 | 10/2001 | Zhang et al. | |
| 6,306,575 B1 | 10/2001 | Thomas et al. | |
| 6,326,174 B1 | 12/2001 | Joyce et al. | |
| 6,326,198 B1 | 12/2001 | Emerson et al. | |
| 6,329,169 B1 | 12/2001 | Ni et al. | |
| 6,335,195 B1 | 1/2002 | Rodgers et al. | |
| 6,338,942 B2 | 1/2002 | Kraus et al. | |
| 6,342,219 B1 | 1/2002 | Thorpe et al. | |
| 6,342,221 B1 | 1/2002 | Thorpe et al. | |
| 6,342,372 B1 | 1/2002 | Dubensky, Jr. et al. | |
| 6,342,581 B1 | 1/2002 | Rosen et al. | |
| 6,372,210 B2 | 4/2002 | Brown | |
| 6,372,473 B1 | 4/2002 | Moore et al. | |
| 6,376,236 B1 | 4/2002 | Dubensky, Jr. et al. | |
| 6,384,192 B1 | 5/2002 | Ingham et al. | |
| 6,413,772 B1 * | 7/2002 | Block | 435/370 |
| 6,413,773 B1 | 7/2002 | Ptasznik et al. | |
| 6,642,019 B1 | 11/2003 | Anderson et al. | |
| 6,645,489 B2 | 11/2003 | Pykett et al. | |
| 6,680,166 B1 | 1/2004 | Mullon et al. | |
| 6,887,704 B2 | 5/2005 | Peled et al. | |
| 6,962,698 B1 | 11/2005 | Peled et al. | |
| 7,169,605 B2 | 1/2007 | Peled et al. | |
| 7,247,477 B2 | 7/2007 | Itskovitz-Eldor et al. | |
| 7,344,881 B2 | 3/2008 | Peled et al. | |
| 2001/0014475 A1 | 8/2001 | Frondoza et al. | |
| 2002/0001826 A1 | 1/2002 | Wager et al. | |
| 2002/0090603 A1 | 7/2002 | Lipton et al. | |
| 2002/0114784 A1 | 8/2002 | Li et al. | |
| 2002/0114789 A1 | 8/2002 | Peled et al. | |
| 2002/0146678 A1 | 10/2002 | Benvenisty | |
| 2002/0146816 A1 | 10/2002 | Vellinger et al. | |
| 2002/0159981 A1 | 10/2002 | Peled et al. | |
| 2002/0159984 A1 * | 10/2002 | Brown | 424/93.21 |
| 2002/0182728 A1 | 12/2002 | Ramiya et al. | |
| 2003/0002363 A1 | 1/2003 | Le et al. | |

(56) References Cited

U.S. PATENT DOCUMENTS

| | | | |
|---|---|---|---|
| 2003/0031665 A1 | 2/2003 | Dang et al. | 424/141.1 |
| 2003/0113913 A1 | 6/2003 | Purton et al. | |
| 2003/0125410 A1 | 7/2003 | Keita et al. | |
| 2003/0149074 A1 | 8/2003 | Melese et al. | |
| 2003/0215445 A1 | 11/2003 | Serrero | |
| 2003/0235909 A1 | 12/2003 | Hariri et al. | |
| 2004/0076603 A1 | 4/2004 | Peled et al. | |
| 2004/0247574 A1 | 12/2004 | Christopherson, II et al. | 424/93.7 |
| 2005/0008624 A1 | 1/2005 | Peled et al. | 424/93.21 |
| 2005/0031595 A1 | 2/2005 | Peled et al. | |
| 2005/0054097 A1 | 3/2005 | Peled et al. | 435/372 |
| 2005/0054103 A1 | 3/2005 | Peled et al. | |
| 2005/0069527 A1 | 3/2005 | Laughlin et al. | |
| 2005/0084961 A1 | 4/2005 | Hedrick et al. | |
| 2005/0095228 A1 | 5/2005 | Fraser et al. | |
| 2005/0118150 A1 | 6/2005 | Peled et al. | |
| 2005/0214262 A1 | 9/2005 | Peled et al. | |
| 2005/0220774 A1 | 10/2005 | Peled et al. | |
| 2005/0260748 A1 | 11/2005 | Chang et al. | |
| 2006/0093605 A1 | 5/2006 | Campana et al. | |
| 2006/0171932 A1 | 8/2006 | Hendricks et al. | |
| 2006/0205071 A1 | 9/2006 | Hasson et al. | |
| 2007/0077652 A1 | 4/2007 | Peled et al. | 435/325 |
| 2008/0279828 A1 | 11/2008 | Peled et al. | |
| 2010/0183564 A1 | 7/2010 | Boitano et al. | |
| 2014/0023623 A1 | 1/2014 | Peled et al. | |
| 2014/0023626 A1 | 1/2014 | Peled et al. | |

FOREIGN PATENT DOCUMENTS

| | | |
|---|---|---|
| AU | 759522 B2 | 4/2003 |
| AU | 770896 B2 | 3/2004 |
| EP | 0 331 464 | 9/1989 |
| EP | 0 331 464 A2 | 9/1989 |
| EP | 1 332 673 | 8/2003 |
| EP | 1 332 673 A1 | 8/2003 |
| EP | 1 332 676 | 8/2003 |
| EP | 1 332 676 A1 | 8/2003 |
| EP | 1 424 389 | 6/2004 |
| JP | 2005528088 A | 9/2005 |
| KR | 20090065814 A | 6/2009 |
| WO | WO 89/02468 | 3/1989 |
| WO | WO-89/02468 A1 | 3/1989 |
| WO | WO 89/05345 | 6/1989 |
| WO | WO-89/05345 A1 | 6/1989 |
| WO | WO 89/07136 | 8/1989 |
| WO | WO-89/07136 A2 | 8/1989 |
| WO | WO 92/07573 | 5/1992 |
| WO | WO-92/07573 A1 | 5/1992 |
| WO | WO 92/11355 | 7/1992 |
| WO | WO-92/11355 A1 | 7/1992 |
| WO | WO 93/09220 | 5/1993 |
| WO | WO-93/09220 A1 | 5/1993 |
| WO | WO 93/18132 | 9/1993 |
| WO | WO-93/18132 A1 | 9/1993 |
| WO | WO 94/18991 | 9/1994 |
| WO | WO-94/18991 A1 | 9/1994 |
| WO | WO 95/14078 | 5/1995 |
| WO | WO-95/14078 A1 | 5/1995 |
| WO | WO 95/21911 | 8/1995 |
| WO | WO-95/21911 A1 | 8/1995 |
| WO | WO 95/24464 | 9/1995 |
| WO | WO-95/24464 A1 | 9/1995 |
| WO | WO 96/01108 | 1/1996 |
| WO | WO-96/01108 A1 | 1/1996 |
| WO | WO 96/40876 | 12/1996 |
| WO | WO-96/40876 A1 | 12/1996 |
| WO | WO 97/04707 | 2/1997 |
| WO | WO-97/04707 A1 | 2/1997 |
| WO | WO 97/31647 | 9/1997 |
| WO | WO-97/31647 A1 | 9/1997 |
| WO | WO 97/33978 | 9/1997 |
| WO | WO-97/33978 A1 | 9/1997 |
| WO | WO 97/41209 | 11/1997 |
| WO | WO-97/41209 A1 | 11/1997 |
| WO | WO 97/41224 | 11/1997 |
| WO | WO-97/41224 A1 | 11/1997 |
| WO | WO 98/25634 | 6/1998 |
| WO | WO-98/25634 A1 | 6/1998 |
| WO | WO 99/07831 | 2/1999 |
| WO | WO-99/07831 A1 | 2/1999 |
| WO | WO 99/18885 | 4/1999 |
| WO | WO-99/18885 A1 | 4/1999 |
| WO | WO 99/40783 | 8/1999 |
| WO | WO-99/40783 A1 | 8/1999 |
| WO | WO 99/64566 | 12/1999 |
| WO | WO-99/64566 A2 | 12/1999 |
| WO | WO 00/18885 | 4/2000 |
| WO | WO-00/18885 A1 | 4/2000 |
| WO | WO 00/30635 | 6/2000 |
| WO | WO-00/30635 A1 | 6/2000 |
| WO | WO 00/46349 | 8/2000 |
| WO | WO-00/46349 A1 | 8/2000 |
| WO | WO 00/66712 | 11/2000 |
| WO | WO-00/66712 A2 | 11/2000 |
| WO | WO 00/73421 | 12/2000 |
| WO | WO-00/73421 A2 | 12/2000 |
| WO | WO 02/064755 | 8/2002 |
| WO | WO-02/064755 A2 | 8/2002 |
| WO | WO 02/080995 | 10/2002 |
| WO | WO-02/080995 A1 | 10/2002 |
| WO | WO-02102299 A2 | 12/2002 |
| WO | WO 03/004626 | 1/2003 |
| WO | WO-03/004626 A1 | 1/2003 |
| WO | WO-03051419 A1 | 6/2003 |
| WO | WO 03/062369 | 7/2003 |
| WO | WO-03/062369 A2 | 7/2003 |
| WO | WO 03/062404 | 7/2003 |
| WO | WO-03/062404 A1 | 7/2003 |
| WO | WO 03/072557 | 9/2003 |
| WO | WO-03/072557 A1 | 9/2003 |
| WO | WO 03/078567 | 9/2003 |
| WO | WO-03/078567 A2 | 9/2003 |
| WO | WO 2004/016731 | 2/2004 |
| WO | WO-2004/016731 A2 | 2/2004 |
| WO | WO 2004/078917 | 9/2004 |
| WO | WO-2004/078917 A2 | 9/2004 |
| WO | WO 2005/007073 A2 | 1/2005 |
| WO | WO-2005/007073 A2 | 1/2005 |
| WO | WO 2005/007799 | 1/2005 |
| WO | WO 2005/086845 * | 9/2005 |
| WO | WO-2005/086845 A2 | 9/2005 |
| WO | WO 2005/086845 A2 | 9/2005 |
| WO | WO 2006/030442 A2 | 3/2006 |
| WO | WO-2006/030442 A2 | 3/2006 |
| WO | WO-2006050270 A2 | 5/2006 |
| WO | WO 2007/063545 | 6/2007 |
| WO | WO-2007/063545 A2 | 6/2007 |
| WO | WO-2008020815 A1 | 2/2008 |
| WO | WO 2008/056368 | 5/2008 |
| WO | WO-2011080740 A1 | 7/2011 |
| WO | WO-2011139357 A1 | 11/2011 |
| WO | WO-2013121426 A1 | 8/2013 |
| WO | WO-2013121427 A1 | 8/2013 |

OTHER PUBLICATIONS

Xia et al., Surface fucosylation of human cord blood cells augments binding to P-selectin and E-selectin and enhances engraftment in bone marrow 2004 104: 3091-3096.*

Ferrari et al., Muscle regeneration by bone marrow-derived myogenic progenitors. Science. Mar. 6, 1998;279(5356):1528-30. Erratum in: Science Aug. 14, 1998;281(5379):923.*

Yang et al, 2004, Mesenchymal stem/progenitor cells developed in cultures from UC blood Cytotherapy pp. 476-486.*

Zhang et al. "Human Placenta-Derived Mesenchymal Progenitor Cells Support Culture Expansion of Long-Term Culture-Initiating Cells From Cord Blood CD34+ Cells", Experimental Hematology, 32: 657-664, Jul. 2004.

European Patent Office Re.: Application No. 05784625.5, "Communication Pursuant to Article94(3) EPC" Dated Nov. 17, 2009.

(56) References Cited

OTHER PUBLICATIONS

European Patent Office Re.: Application No. 06821601.9, "Communication Pursuant to Article 94(3) EPC" Dated Aug. 20, 2009.
Israel Patent Office Re.: Application No. 181976 "Office Action (and Its Translation Into English)" Dated Nov. 29, 2009.
Singapore Intellectual Property Office Issued by the Australian Patent Office Re.: Application No. SG 200804154-3 "Search Report and Written Opinion" Dated Aug. 10, 2009.
U.S. Patent and Trademark Office Re.: U.S. Appl. No. 11/606,525, "Official Action" Dated Oct. 23, 2009.
Campbell et al. "CD26 Inhibition and Hematopoiesis: A Novel Approach to Enhance Transplantation." *Front Biosci*. 1(2008):1795-1805.
Campbell et al. "Inhibition of CD26 in Human Cord Blood CD34+ Cells Enhance Their Engraftment of Nonobese Diabetic/Severe Combined Immunodeficiency Mice." *Stem Cells Dev*. 16.3(2007):347-354.
Farre et al. "FGF-4 Increases In Vitro Expansion Rate of Human Adult Bone Marrow-Derived Mesenchymal Stem Cells." *Growth Factors*. 25.2(2007):71-76.
Psaltis et al. "Enrichment for STRO-1 Expression Enhances the Cardiovascular Paracrine Activity of Human Bone Marrow-Derived Mesenchymal Cell Populations." *J. Cell. Physiol*. 223(2010):530-540.
Handgretinger et al., "Biology and Plasticity of CD133+ Hematopoietic Stem Cells", Annals of the N.Y. Acad. Sci., 996:141-151, May 2003.
Morita et al., "Heterogeneity and Hierarchy Within Most Primitive Hematopoietic Stem Cell Compartment" The J. of Exp. Med, JEM, 207(6): 1173-1182, Jun. 7, 2010.
Aiuti et al. "The Chemokine SDF-1 Is a Chemoattractant for Human CD34+ Hematopoietic Progenitor Cells and Provides a New Mechanism to Explain the Mobilization of CD34+ Progenitors to Peripheral Blood", Journal of Experimental Medicine, 185(1): 111-120, 1997.
Anderlini et al. "The Use of Mobilized Peripheral Blood Stem Cells From Normal Donors for Allografting", Stem Cells, 15: 9-17, 1997.
Arriero et al. "Adult Skeletal Muscle Stem Cells Differentiate Into Endothelial Lineage and Ameliorate Renal Dysfunction After Acute Ischemia", American Journal of Physiology—Renal Physiology, 287: F621-F627, 2004.
Baggiolini "Chemokines and Leukocyte Traffic", Nature, 392: 565-568, 1998.
Banasik et al. "Specific Inhibitors of Poly(ADP-Ribose) Synthetase and Mono(ADP-Ribosyl)Transferase", The Journal of Biological Chemistry, 267(3): 1569-1575, 1992.
Bernhard et al. "Generation of Immunostimulatory Dendritic Cells From Human CD34+ Hematopoietic Progenitor Cells of the Bone Maroow and Peripheral Blood", Cancer Research, 55: 1099-1104, 1995.
Bohmer et al. "Fetal Cell Isolation From Maternal Blood Cultures by Flow Cytometric Hemoglobin Profiles", Fetal Diagnosis and Therapy, 17(2): 83-89, 2002.
Bongers et al. "Kinetics of Dipeptidyl Peptidase IV Proteolysis of Growth Hormone-Releasing Factor and Analogs", Biochimica et Biophysica Acta, 1122: 147-153, 1992.
Broxmeyer "Regulation of Hematopoiesis by Chemokine Family Members", International Journal of Hematology, 74: 9-17, 2001.
Brugger et al. "Reconstitution of Hematopoiesis After High-Dose Chemotherapy by Autologous Progenitor Cells Generated Ex Vivo", New England Journal of Medicine, 333(5): 283-287, 1995.
Christopherson II et al. "Cell Surface Peptidase CD26/Dipeptidylpeptidase IV Regulates CXCL12/Stromal Cell-Derived Factor-1α-Mediated Chemotaxis of Human Cord Blood CD34+ Progenitor Cells", The Journal of Immunology, 169: 7000-7008, 2002.
Christopherson II et al. "Modulation of Hematopoietic Stem Cell Homing and Engraficuent by CD26", Science, 305: 1000-1003, 2004.
Corda et al. "Functional Aspects of Protein Mono-ADP-Ribosylation", The EMBO Journal, 22(9): 1953-1958, 2003.
Czyz et al. "Potential of Embryonic and Adult Stem Cell In Vitro", Biological Chemistry, 384: 1391-1409, 2003.
De La Cruz et al. "Do Protein Motifs Read the Histone Code?", BioEssays, 27.2: 164-175, 2005.
Donovan et al. "The End of the Beginning for Pluripotent Stem Cells", Nature, 414(6859): 92-97, 2001.
Emerson, S.G. "Ex Vivo Expansion of Hematopoietic Precursors, Progenitors, and Stem Cells: The Next Generation of Cellular Therapeutics", Blood, 87(8): 3082-3088, 1996.
Ferrari et al. "Muscle Regeneration by Bone Marrow-Derived Myogenic Progenitors", Science, 279(5356): 1528-1530, 1998. Erratum in: Science, 281(5379): 923, 1998.
Fisch et al. "Generation of Antigen-Presenting Cells for Soluble Protein Antigens Ex Vivo From Peripheral Blood CD34+ Hematopoietic Progenitor Cells in Cancer Patients", European Journal of Immunology, 26: 595-600, 1996.
Freedman et al. "Generation of Human T Lymphocytes From Bone Marrow CD34+ Cells In Vitro", Nature Medicine, 2(1): 46-51, 1996.
Gluckman et al. "Hematopoietic Reconstitution in a Patient With Fanconi's Anemia by Means of Umbilical-Cord Blood From an HLA-Identical Sibling", The New England Journal of Medicine, 321(17): 1174-1178, 1989.
Heslop et al. "Long-Term Restoration of Immunity Against Epstein-Barr Virus Infection by Adoptive Transfer of Gene-Modified Virus-Specific T Lymphocytes", Nature Medicine, 2(5): 551-555, 1996.
Hühn et al. "Molecular Analysis of CD26-Mediated Signal Transduction in T Cells", Immunology Letters, 72: 127-132, 2000.
Imai et al. "Selective Secretion of Chemoattractants for Haemopoietic Progenitor Cells by Bone Marrow Endothelial Cells: A Possible Role in Homing of Haemopoietic Progenitor Cells to Bone Marrow", British Journal of Haematology, 106: 905-911, 1999.
Imitola et al. "Directed Migration of Neural Stem Cells to Sites of CNS Injury by the Stromal Cell-Derived Factor 1α/CXC Chemokine Receptor 4 Pathway", Proc. Natl. Acad. Sci. USA, 101(52): 18117-18122, 2004.
Jackson et al. "Regeneration of Ischemic Cardiac Muscle and Vascular Endothelium by Adult Stem Cells", The Journal of Clinical Investigation, 107(11): 1395-1402, 2001.
Kähne et al. "Dipeptidyl Peptidase IV: A Cell Surface Peptidase Involved in Regulating T Cell Growth (Review)", International Journal of Molecular Medicine, 4: 3-15, 1999.
Koller et al. "Large-Scale Expansion of Human Stem and Progenitor Cells From Bone Marrow Mononuclear Cells in Continous Perfusion Cultures", Blood, 82(2): 378-384, 1993.
Lambeir et al. "Kinetic Investigation of Chemokine Truncation by CD26/Dipeptidyl Peptidase IV Reveals a Striking Selectivity Within the Chemokine Family", The Journal of Biological Chemistry, 276(32): 29839-29845, 2001.
Lebkowski et al. "Rapid Isolation and Serum-Free Expansion of Human CD34+ Cells", Blood Cells, 20: 404-410, 1994.
Lee et al. "Repair of Ischemic Heart Disease With Novel Bone Marrow-Derived Multipotent Stem Cells", Cell Cycle, 4(7): 861-864, 2005.
Lupi et al. "Endogenous ADP-Ribosylation of the G Protein β Subunit Prevents the Inhibition of Type 1 Adenylyl Cyclase", The Journal of Biological Chemistry, 275(13): 9418-9424, 2000.
McGrath et al. "Embryonic Expression and Function of the Chemokine SDF-1 and Its Receptor, CXCR4", Developmental Biology, 213: 442-456, 1999.
Miraglia et al. "A Novel Five-Transmembrane Hematopoietic Stem Cell Antigen: Isolation, Characterization, and Molecular Cloning", Blood, 90(12): 5013-5021, 1997.
Nagaya et al. "Intravenous Administration of Mesenchymal Stem Cells Improves Cardiac Functions in Rats With Acute Myocardial Infarction Through Angiogenesis and Myogenesis", American Journal of Physiology—Heart Circulation Physiology, 287: H2670-H2676, 2004.
Orlic et al. "Bone Marrow Cells Regenerate Infarcted Myocardium", Nature, 410: 701-705, 2001.
Palmiter, R.D. "Regulation of Metallothionein Genes by Heavy Metals Appears to be Mediated by a Zinc-Sensitive Inhibitor That Interacts With a Constitutively Active Transcription Factor, MTF-1", Proc. Natl. Acad. Sci. USA, 91: 1219-1223, 1994.

(56) References Cited

OTHER PUBLICATIONS

Peled et al. "Dependence of Human Stem Cell Engraftment and Repopulation of NOD/SCID Mice on CXCR4", Science, 283: 845-848, 1999.
Prockop et al. "Isolation and Characterization of Rapidly Self-Renewing Stem Cells From Cultures of Human Marrow Stromal Cells", Cytotherapy, 3(5): 393-396, 2001.
Protti et al. "Particulate Naturally Processed Peptides Prime a Cytotoxic Response Against Human Melanoma In Vitro", Cancer Research, 56: 1210-1213, 1996.
Rankin et al. "Quantitative Studies of Inhibitors of ADP-Ribosylation In Vitro and In Vivo", The Journal of Biological Chemistry, 264(8): 4312-4317, 1989.
Roach et al. "Methods for the Isolation and Maintenance of Murine Embryonic Stem Cells", Methods in Molecular Biology—Embryonic Stem Cells: Methods and Protocols, 185: 1-16, 2002.
Rosenberg et al. "Prospective Randomized Trial of High-Dose Interleukin-2 Alone or in Conjunction With Lymphokine-Activated Killer Cells for the Treatment of Patients With Advanced Cancer", Journal of the National Cancer Institute, 85(8): 622-632, 1993.
Rowley et al. "Isolation of CD34+ Cells From Blood Stem Cell Components Using the Baxter Isolex System", Bone Marrow Transplantation, 21: 1253-1262, 1998.
Rubinstein et al. "Processing and Cryopreservation of Placental/Umbilical Cord Blood for Unrelated Bone Marrow Reconstitution", Proc. Natl. Acad. Sci. USA, 92: 10119-10122, 1995.
Sandstrom et al. "Effects of CD34+ Cell Selection and Perfusion on Ex Vivo Expansion of Peripheral Blood Mononuclear Cells", Blood, 86(3): 958-970, 1995.
Shioda et al. "Anti-HIV-1 and Chemotactic Activities of Human Stromal Cell-Derived Factor 1α (SDF-1α) and SDF-1β Are Abolished by CD26/Dipeptidyl Peptidase IV-Mediated Cleavage", Proc. Natl. Acad. Sci. USA, 95: 6331-6336, 1998.
Siena et al. "Massive Ex Vivo Generation of Functional Dendritic Cells From Mobilized CD34+ Blood Progenitors for Anticancer Therapy", Experimental Hematology, 23: 1463-1471, 1995.
Simmons et al. "Identification of Stromal Cell Precursors in Human Bone Marrow by a Novel Monoclonal Antibody, STRO-1", Blood, 78(1): 55-62, 1991.
Smith, A.G. "Embryo-Derived Stem Cells: of Mice and Men", Annual Reviews of Cell and Developmental Biology, 17: 435-462, 2001.
Smith, S. "The World According to PARP", Trends in Biochemical Sciences, 26(3): 174-179, 2001.
Struyf et al. "Natural Truncation of RANTES Abolishes Signaling Through the CC Chemokine Receptors CCR1 and CCR3, Impairs Its Chemotactic Potency and Generates a CC Chemokine Inhibitor", European Journal Immunology, 28: 1262-1271, 1998.
Sylvester et al. "Stem Cells: Review and Update", Archives of Surgery, 139: 93-99, 2004.
Tögel et al. "Administered Mesenchymal Stem Cells Protect Against Ischemic Acute Renal Failure Through Differentiation-Independent Mechanisms", American Journal of Physiology—Renal Physiology, 289: F31-F42, 2005.
Trounson, A.O. "The Derivation and Potential Use of Human Embryonic Stem Cells", Reproduction, Fertility and Development, 13: 523-532, 2001.
Tse et al. "Angiogenesis in Ischaemic Myocardium by Intramyocardial Autologous Bone Marrow Mononuclear Cell Implantation", The Lancet, 361: 47-49, 2003.
Uchida et al. "Direct Isolation of Human Central Nervous System Stem Cells", Proc. Natl. Acad. Sci. USA, 97(26): 14720-14725, 2000.
Ueda et al. "ADP-Ribosylation", Annual Reviews of Biochemistry, 54: 73-100, 1985.
Van Epps et al. "Harvesting, Characterization, and Culture of CD34+ Cells From Human Bone Marrow, Peripheral Blood, and Cord Blood", Blood Cells, 20(2-3): 411-423, 1994.

Vanham et al. "Decreased Expression of the Memory Marker CD26 on Both CD4+ and CD8+ T Lymphocytes of HIV-Infected Subjects", Journal of Acquired Immune Deficiency Syndromes, 6: 749-757, 1993.
Virág et al. "The Therapeutic Potential of Poly(ADP-Ribose) Polymerase Inhbititors", Pharmacological Reviews, 54(3): 375-429, 2002.
Williams et al. "Selection and Expansion of Peripheral Blood CD34+ Cells in Autologous Stem Cell Transplantation for Breast Cancer", Blood, 87(5): 1687-1691, 1996.
Xia et al. "Surface Fucosylation of Human Cord Blood Cells Augments Binding to P-Selectin and E-Selectin and Enhances Engraftment in Bone Marrow", Blood, 104(10): 3091-3096, 2004.
Yau et al. "Endogenous Mono-ADP-Ribosylation Mediates Smooth Muscle Cell Proliferation and Migration Via Protein Kinase N-Dependent Induction of C-Fos Expression", European Journal of Biochemistry, 270: 101-110, 2003.
Zimmerman et al. "Large-Scale Selection of CD34+ Peripheral Blood Progenitors and Expansion of Neutrophil Precursors for Clinical Applications", Journal of Hematotherapy, 5: 247-253, 1996.
Acsadi et al. "Human Dystrophin Expression in Mdx Mice After Intramuscular Injection of DNA Constructs", Nature, 352: 815-818, 1991.
Alter "Fetal Erythropoiesis in Stress Hemopoiesis", Experimental Hematology, 7(5): 200-209, 1979.
American Cancer Society "Chelation Therapy", ACS, p. 1-5, 2006.
Aoki et al. "In Vivo Transfer Efficiency of Antisense Oligonucleotides Into the Myocardium Using HVJ-Liposome Method", Biochemical and Biophysical Research Communications, 231: 540-545, 1997.
Armentano et al. "Expression of Human Factor IX in Rabbit Hepatocytes by Retrovirus-Mediated Gene Transfer: Potential for Gene Therapy of Hemophilia B", Proc. Natl. Acad. Sci. USA, 87: 6141-6145, 1990.
Asahara et al., "Stem cell therapy and gene transfer for regeneration", *Gene Therapy*, 7:451-457 (2000).
Auger et al. "PDGF-Dependent Tyrosine Phosphorylation Stimulates Production of Novel Polyphosphoinositides in Intact Cells", Cell, 57: 167-175, 1989.
Avital et al. "Isolation, Characterization, and Transplantation of Bone Marrow-Derived Hepatocyte Stem Cells", Biochemical and Biophysical Research Communications, 288(1): 156-164, 2001.
Bae et al. "Copper Uptake and Intracellular Distribution During Retinoic Acid-Induced Differentiation of HL-60 Cells", Journal of Nutritional Biochemistry, Food Science and Human Nutrition Department, 5: 457-461, 1994.
Banno et al. "Anemia and Neutropenia in Eldery Patients Caused by Copper Deficiency for Long-Term Eternal Nutrition", Rinsho-Ketsueki, 35: 1276-1280, 1994.
Baum et al. "Isolation of a Candidate Human Hematopoietic Stem-Cell Population", Proc. Natl. Acad. Sci. USA, 89: 2804-2808, 1992.
Belovari et al. "Differentiation of Rat Neural Tissue in a Serum-Free Embryo Culture Model Followed by In Vivo Transplantation", Croatian Medical Journal, 42(6): 611-617, 2001. Abstract.
Berardi et al. "Individual CD34+CD38lowCD19-CD10-Progenitor Cells From Human Cord Blood Generate B Lymphocytes and Granulocytes", Blood, 89(10): 3554-3564, 1997.
Berkner "Development of Adenovirus Vectors for the Expression of Heterologous Genes", BioTechniques, 6(7): 616-629, 1988.
Bertagnolo et al. "Phosphoinositide 3-Kinase Activity is Essential for all-trans-Retinoic Acid-induced Granulocytic Differentiation of HL-60 Cells", Cancer Res., 59: 542-546, 1999.
Bhatia et al. "Purification of Primitive Human Hematopoietic Cells Capable of Repopulating Immune-Deficient Mice", Proc. Natl. Acad. Sci. USA, 94: 5320-5325, 1997.
Bhat-Nakshatri, et al., "Tumour necrosis factor and PI3-kinase control oestrogen receptor alpha protein level and its transrepression function", *Br. J. Cancer*, 90:853-859 (2004).
Bi et al. "Effect of Lactoferrin on Proliferation and Differentiation of the Jurkat Human Lymphoblastic T Cell Line", Arch. Immunol. Ther. Exp., 45(4): 315-320, 1997. Abstract.

(56) References Cited

OTHER PUBLICATIONS

Bieback et al., "Critical Parameters for the Isolation of Mesenchymal Stem Cell from Umbilical Cord Blood", *Stem Cells*, 22:625-634 (2004).
Bird et al. "Single-Chain Antigen-Binding Proteins", Science, 242: 423-426, 1988.
Birkenkamp, et al., "An inhibitor of PI3-K differentially affects proliferation and IL-6 protein secretion in normal and leukemic myeloid cells depending on the stage of differentiation", *Exp. Hematol.*, 28:1239-1249 (2000).
Blau et al. "Fetal Hemoglobin in Acute and Chronic Stage of Erythroid Expansion", Blood, 81(1): 227-233, 1993.
Boerner et al. "Production of Antigen-Specific Human Monoclonal Antibodies From In Vitro-Primed Human Splenocytes", The Journal of Immunology, 147(1): 86-95, 1991.
Borthwick et al. "A Comparison of Cupruretic Responses to Various Tetramines and D-Penicillamine", Journal of Laboratory and Clinical Medicine, 95(4): 575-580, 1980.
Brandt et al. "Ex Vivo Expansion of Autologous Bone Marrow CD34+ Cells With Porcine Microvascular Endothelial Cells Results in a Graft Capable of Rescuing Lethally Irradiated Baboons", Blood, 94(1): 106-113, 1999.
Brazelton et al. "From Marrow to Brain: Expression of Neuronal Phenotypes in Adult Mice", Science, 290(5497): 1775-1779, 2000. Abstract.
Breitman et al. "Induction of Differentiation of the Human Promyelocytic Leukemia Cell Line (HL-60) by Retinoic Acid", Proc. Natl. Acad. Sci., 77(5): 2936-2940, 1980.
Briddell et al. "Purification of CD34+ Cells Is Essential for Optimal Ex Vivo Expansion of Umbilical Cord Blood Cells", Journal of Hematotherapy, 6: 145-150, 1997.
Brigham et al. "Rapid Communication: In Vivo Transfection of Murine Lungs With a Functioning Prokaryotic Gene Using a Liposome Vehicle", The American Journal of the Medical Sciences, 298(4): 278-281, 1989.
Brott et al. "Flow Cytometric Characterization of Perfused Human Bone Marrow Cultures: Identification of the Major Cell Lineages and Correlation With the CFU-GM Assay", Cytometry Part A, 53A: 22-27, 2003.
Brugger et al. "Ex Vivo Expansion of Enriched Peripheral Blood CD34+ Progenitor Cells by Stem Cell Factor, Interleukin-1? (IL-1?), IL-6, IL-3, Interferon-?, and Erythropoietin", Blood, 81(10); 2579-2584, 1993.
Brugnera et al. "Cloning, Chromosomal Mapping and Characterization of the Human Metal-Regulatory Transcription Factor MTF-1", Nucleic Acids Research, 22(15): 3167-3173, 1994.
Bryder et al. "Hematopoietic Stem Cells: the paradigmatic tissue-specific stem cell." Am J Pathol., 169(2):338-46, 2006.
Burgada et al. "Synthesis of New Phosphonated Tripod Ligands as Putative New Therapeutic Agents in the Chelation Treatment of Metal Intoxications", European Journal of Organic Chemistry, p. 349-352, 2001.
Buskin et al. "Identification of a Myocyte Nuclear Factor That Binds to the Muscle-Specific Enhancer of the Mouse Muscle Creatine Kinase Gene", Molecular and Cellular Biology, 9(6): 2627-2640, 1989.
Butt "Introduction to Chemical Reactor Theory", Reaction Kinetics and Reactor Design, Chap.4: 184-241, 1980.
Cable et al. "Exposure of Primary Rat Hepatocytes in Long-Term DMSO Culture to Selected Transition Metals Induces Hepatocyte Proliferation and Formation of Duct-Like Structure", Hepatoloty, 26(6): 1444-1457, 1997.
Cakir-Kiefer et al. "Kinetic Competence of the cADP-Ribose-CD38 Complex as an Intermediate in the CD38/NAD+ Glycohydrolase-Catalysed Reactions: Implication for CD38 Signalling", Biochemical Journal, 358: 399-406, 2001.
Caliaro et al. "Response of Four Human Ovarian Carcinoma Cell Lines to All-Trans Retinoic Acid: Relationship With Induction of Differentiation and Retinoic Acid Receptor Expression", International Journal of Cancer, 56: 743-748, Mar. 1, 1994.
Casal et al. "In Utero Transplantation of Fetal Liver Cells in the Mucopolysaccharidosis Type VII Mouse Results in Low-Level Chimerism, But Overexpression of Beta-Glucuronidase Can Delay Onset of Clinical Signs", Blood, 97(6): 1625-1634, 2001.
Cepko "Overview of the Retrovirus Transduction System", Short Protocols in Molecular Biology, Unit 9.10-9.14: 9-41-9-57, 1984.
Charrier et al. "Normal Human Bone Marrow CD34+CD133+ Cells Contain Primitive Cells Able to Produce Different Categories of Colony-Forming Unit Megacaryocytes In Vitro", Experimental Hematology, 30: 1051-1060, 2002.
ChemMasters "Duraguard 100", Safety Data Sheet, p. 1-4, 1999.
Chen et al. "Differentiation of Rat Marrow Mesenchymal Stem Cells into Pancreatic Islet Beta-Cells", World Journal of Gastroeneterology, 19(20): 3016-3020, 2004.
Chen et al. "Fibroblast Growth Factor (FGF) Signaling Through PI 3-Kinase and Akt/PKB Is Required for Embryoid Body Differentiation", Oncogene, 19: 3750-3756, 2000. p. 3752-3755.
Chen et al. "Therapeutic Benefit of Intravenous Administration of Bone Marrow Stromal Cells After Cerebral Ischemia in Rats", Stroke, 32(4): 1005-1011, 2001.
Chisi et al. "Inhibitory Action of the Peptide AcSDKP on the Proliferative State of Hematopoietic Stem Cells in the Presence of Captopril But Not Lisinopril", Stem Cells, 15(6): 455-460, 1997.
Chowdhury et al. "Long-Term Improvement of Hypercholesterolemia After Ex Vivo Gene Therapy in LDLR-Deficient Rabbits", Science, 254: 1802-1805, 1991.
Cicuttini et al. "Support of Human Cord Blood Progenitor Cells on Human Stromal Cell Lines Transformed by SV40 Large T Antigen Under the Influence of an Inducible (Metallothionein) Promoter", Blood, 80(1): 102-112, 1992.
Cole et al. "The EBV-Hybridoma Technique and Its Application to Human Lung Cancer", Monoclonal Antibodies and Cancer Therapy, p. 77-96, 1985.
Colter et al. "CD34+ Progenitor Cell Selection: Clinical Transplantation, Tumor Cell Purging, Gene Therapy, Ex Vivo Expansion, and Cord Blood Processing", Journal of Hematology, 5: 179-184, 1996.
Cóteet al. "Response to Histone Deacetylase Inhibition of Novel PML/RARα Mutants Detected in Retinoic Acid-Resistant APL Cells", Blood, 100(7): 2586-2596, 2002.
Coutinho et al. "Effects of Recombinant Human Granulocyte Colony-Stimulating Factor (CSF), Human Granulocyte Macrophage-CSF, and Gibbon Interleukin-3 on Hematopoiesis in Human Long-Term Bone Marrow Culture", Blood, 75(11): 2118-2129, 1990.
Cristiano et al. "Hepatic Gene Therapy: Adenovirus Enhancement of Receptor-Mediated Gene Delivery and Expression in Primary Hepatocytes", Proc. Natl. Acad. Sci. USA, 90: 2122-2126, 1993.
Curiel et al. "Adenovirus Enhancement of Transferrin-Polylysine-Mediated Gene Delivery", Proc. Natl. Acad. Sci. USA, 88: 8850-8854, 1991.
Czauderna, et al., "Functional studies of the Pl(3)-kinase signalling pathway employing synthetic and expressed siRNA. ", *Nuc. Acid Res.*, 31(2):670-682 (2003).
Dabeva et al. "Transcription Factor and Liver-Specific mRNA Expression in Facultative Epithelial Progenitor Cells of Liver and Pancreas", American Journal of Pathology, 147: 1633-1648, 1995. Abstract.
Dahl et al. "Tranformation of Hematopoietic Cells by the Ski Oncoprotein Involves Repression of Retinoic Acid Receptor Signaling", Proc. Natl. Acad. Sci. USA, 95(19): 11187-11192, 1998.
Dai et al. "Gene Therapy Via Primary Myoblasts: Long-Term Expression of Factor IX Protein Following Transplantation In Vivo", Proc. Natl. Acad. Sci. USA, 89: 10892-10895, 1992.
Dalyot et al. "Adult and Neonatal Patterns of Human Globin Gene Expression Are Recapitulated in Liquid Cultures", Experimental Hematology, 20: 1141-1145, 1992.
Danos et al. "Safe and Efficient Generation of Recombinant Retroviruses With Amphotropic and Ecotropic Host Ranges", Proc. Natl. Acad. Sci. USA, 85: 6460-6464, 1988.
Datta et al. "Ionizing Radiation Activates Transcription of the EGR1 Gene Via CArG Elements", Proc. Natl. Acad. Sci. USA, 89: 10149-10153, 1992.

(56) References Cited

OTHER PUBLICATIONS

De Bruyn et al. "Comparison of the Coexpressioin of CD33 and HLA-DR Antigens on CD34+ Purified Cells From Human Cord Blood and Bone Narrow", Stem Cells, 13: 281-288, 1995.
De Luca et al. "Retinoic Acid Is a Potent Regulator of Growth Plate Chondrogenesis", Endocrinology, 141(1): 346-353, 2000. Abstract.
De Wynter et al. "CD34+AC133+ Cells Isolated From Cord Blood Are Highly Enriched in Long-Term Culture-Initiating Cells, NOD/SCID-Repopulating Cells and Dendritic Cell Progenitors", Stem Cells, 16: 387-396, 1998.
Defacque et al. "Expression of Retinoid X Receptor Alpha Is Increased Upon Monocytic Cell Differentiation", Biochemical and Biophysical Research Communications, 220: 315-322, 1996.
Dexter et al. "Conditions Controlling the Proliferation of Haemopoietic Stem Cells In Vitro", Journal of Cell Physiology, 91: 335-344, 1976.
Dosil et al., "Mitogenic signalling and substrate specificity of the Flk2/Flt3 receptor tyrosine kinase in fibrobiasis and interleukin 3-dependent hematopoietic cells", *Mo. Cell Biol.*, 13(10):6572-6585 (1993). Abstract.
Douer et al. "All-trans-retinoic Acid Effects the Growth, Differentiation and Apoptosis of Normal Human Myeloid Progenitors Derived from Purified CD34+ Bone Marrow Cells ", Leukemia, 14(5): 874-881, 2000.
Drayson et al. "Cell Proliferation and CD11b Expression are Controlled Independently During HL60 Cell Differentiation Initiated by 1,25α-Dihydroxyvitamin D3 or All-trans-Retinoic Acid", Exp. Cell Res., 266(1): 126-134, 2001. Abstract.
Dubois et al. "Treatment of Wilson's Disease With Triethylene Tetramine Hydrochloride (Trientine)", Journal of Pediatric Gastroenterology and Nutrition, 10(1): 77-81, 1990. Abstract.
Duncan et al. "Repair of Myelin Disease: Strategies and Progress in Animal Models", Molecular Medicine Today, 3(12): 554-561, 1997. Abstract.
Ebner et al. "Distinct Roles for PI3K in Proliferation and Survival of Oligodendrocyte Progenitor Cells", Journal of Neuroscience Research, 62: 336-345, 2000. p. 338-344.
Eglitis et al. "Gene Expression in Mice After High Efficiency Retroviral-Mediated Gene Transfer", Science, 230: 1395-1398, 1985.
Ehring et al. "Expansion of HPCs From Cord Blood in a Novel 3D Matrix", Cytotherapy, 5(6): 490-499, 2003.
Eipers et al. "Retroviral-Mediated Gene Transfer in Human Bone Marrow Cells Grown in Continuous Perfusion Culture Vessels", Blood, 86(10): 3754-3762, 1995.
Englisch et al. "Chemically Modified Oligonucleotides as Probes and Inhibitors", Angewandte Chemie (International Edition in English), 30(6): 613-629, 1991.
Fasouliotis et al. "Human Umbilical Cord Blood Banking and Transplantation: A State of the Art", European Journal of Obstetrics & Gynecology and Reproductive Biology, 90(1): 13-25, 2000.
Feldman "Israeli Start-Up Gamida-Cell to Receive Prize", Globes—Online, 2004.
Ferbeyre "PML a Target of Translocations in APL Is a Regulator of Cellular Senescence", Leukemia, 16: 1918-1926, 2002. Abstract.
Ferrero et al. "The Metamorphosis of a Molecule: From Soluble Enzyme to the Leukocyte Receptor CD38", Journal of Leukocyte Biology, 65(2): 151-161, 1999.
Ferry et al. "Retroviral-Mediated Gene Transfer Into Hepatocytes In Vivo", Proc. Natl. Acad. Sci. USA, 88: 8377-8381, 1991.
Fibach et al. "Growth of Human Normal Erythroid Progenitors in Liquid Culture: A Comparison With Colony Growth in Semisolid Culture", International Journal of Cell Cloning, 9: 57-64, 1991.
Fibach et al. "Normal Differentiation of Myeloid Leukemic Cells Induced by a Protein Differentiation-Inducing Protein", Nature New Biology, 237(78): 276-278, 1972.
Fibach et al. "Proliferation and Maturation of Human Erythroid Progenitors in Liquid Culture", Blood, 73(1): 100-103, 1989. Abstract.
Fibach et al. "Retinoic Acid Antagonist Inhibits CD38 Antigen Expression on Human Hematopoietic Cells", Blood, 100(11): 172A & 44th Annual Meeting of the American Society of Hematology, 2002. Abstract.
Fibach et al. "The Two-Step Liquid Culture: A Novel Procedure for Studying Maturation of Human Normal and Pathological Erythroid Precursors", Stem Cells, 11(Suppl.1): 36-41, 1993. Abstract.
Fietz et al. "Culturing Human Umbilical Cord Blood: A Comparison of Mononuclear Vs CD34+ Selected Cells", Bone Marrow Transplantation, 23: 1109-1115, 1999.
Filvaroff et al. "Functional Evidence for an Extracellular Calcium Receptor Mechanism Triggering Tyrosine Kinase Activation Associated With Mouse Keratinocyte Differentiation", The Journal of Biological Chemistry, 269(34): 21735-21740, 1994.
Fishwild et al. "High-Avidity Human IgG? Monoclonal Antibodies From a Novel Strain of Minilocus Transgenic Mice", Nature Biotechnology, 14: 845-851, 1996.
Flores et al. "Akt-Mediated Survival of Oligodendrocytes Induced by Neuregulins", The Journal of Neuroscience, 20(20): 7622-7630, 2000. p. 7624-7629.
Flotte et al. "Expression of the Cystic Fibrosis Transmemebrane Conductance Regulators From a Novel Adeno-Associated Virus Promoter", The Journal of Biological Chemistry, 268(5): 3781-3790, 1993.
Flotte et al. "Gene Expression From Adeno-Associated Virus Vectors in Airways Epithelial Cells", American Journal of Respiratory Cell and Molecular Biology, 7: 349-356, 1992.
Forraz, et al., "AC133+ umbilical cord blood progenitors demonstrate rapid self-renewal and low apoptosis.", *Br. J. Haematol.*, 119(2):516-524 (2002).
Fosmire "Zinc Toxicity", American Journal of Clinical Nutrition, 51(2): 225-227, 1990. Abstract.
Fry, M. J., "Phosphoinositide 3-kinase signalling in breast cancer: how big a role might it play? ", *Breast Cancer Res.*, 3(5):304-312 (2001).
Gagnon et al. "Activation of Protein Kinase B and Induction of Adipogenesis by Insulin in 3T3-L1 Preadipocytes", Diabetes, 48: 691-698, 1999. p. 693-697.
Gallacher et al. "Isolation and Characterization of Human CD34-Lin- and CD34+Lin-Hematopoietic Stem Cells Using Cell Surface Markers AC133 and CD7", Blood, 95(9): 2813-2820, 2000.
Gloeckner et al. "New Miniaturized Hollow-Fiber Bioreactor for In Vivo Like Cell Culture, Cell Expansion, and Production of Cell-Derived Products", Biotechnology Progresses, 17: 828-831, 2001.
Gossler et al. "Transgenesis by Means of Blasocyst-Derived Embryonic Stem Cell Lines", Proc. Natl. Acad. Sci. USA, 83: 9065-9069, 1986.
Gould-Fogerite et al. "Chimerasome-Mediated Gene Transfer In Vitro and In Vivo", Gene, 84: 429-438, 1989.
Grande et al. "Physiological Levels of 1Alpha, 25 Dihydroxyvitamin D3 Induce the Monocytic Commitment of CD34+ Hematopoietic Progenitors", J. Leukoc. Biol., 71(4): 641-651, 2002.
Grenda et al. "Mice Expressing a Neutrophil Elastase Mutation Derived From Patients With Severe Congenital Neutropenia Have Normal Granulopoiesis", Blood, 100(9): 3221-3228, 2002.
Gur et al. "Toelrance Induction by Megadose Hematopoietic Progenitor Cells: Expansion of Veto Cells by Short-Term Culture of Purified Human CD34+ Cells", Blood, 99: 4174-4181, 2002.
Haj-Ahmad et al. "Development of a Helper-Independent Human Adenovirus Vector and Its Use in the Transfer of the Herpes Simplex Virus Thymidine Kinase Gene", Journal of Virology, 57(1): 267-274, 1986.
Hamilton "Stem Cell Technology to Treat Leukemia Patients Show Promise", The Wall Street Journal, Online, 2003.
Hammond et al. "Suppression of In Vitro Granulocytopoiesis by Captopril and Penicillamine", Experimental Hematology, 16(8): 674-680, 1988.
Hatayama et al. "Regulation of HSP70 Synthesis Induced by Cupric Sulfate and Zinc Sulfate in Thermotolerant HeLa Cells", Journal of Biochemistry, Tokyo, 114(4): 592-597, 1993. Abstract.
Haviernik et al., "Tissue inhibitor of matrix metalloproteinase-1 overexpression in M1 myeloblasts impairs IL-6-induced differentiation", *Oncogene*, 23(57):9212-9219 (2004). Abstract.

(56) References Cited

OTHER PUBLICATIONS

Hayashi et al. "Changes in the Balance of Phosphoinositide 3-Kinase/Protein Kinase B (AKt) and the Mitogen-activated Protein Kinases (ERK/p38MAPK) Determine a Phenotype of Visceral and Vascular Smooth Muscle Cells", J. Cell Biol., 145(4): 727-740, 1999.
Haylock et al. "Ex-Vivo Expansion and Maturation of Peripheral Blood CD34+ Cells Into the Myeloid Lineage", Blood, 80(5): 1405-1412, 1992.
Hermonat et al. "Use of Adeno-Associated Virus as a Mammalian DNA Cloning Vector: Transduction of Neomycin Resistance Into Mammalian Tissue Culture Cells", Proc. Natl. Acad. Sci. USA, 81: 6466-6470, 1984.
Herz et al. "Adenovirus-Mediated Transfer of Low Density Lipoprotein Receptor Gene Acutely Accelerates Cholesterol Clearence in Normal Mice", Proc. Natl. Acad. Sci. USA, 90: 2812-2816, 1993.
Heuchel et al. "The Transcription Factor MTF-1 Is Essential for Basal and Heavy Metal-Induced Metallothionein Gene Expression", The EMBO Journal, 13(12): 2870-2875, 1994.
Hida et al. "Existence of Retinoic Acid-Receptor-Independent Retinoid X-Receptor-Dependent Pathway in Myeloid Cell Function", Japanese Journal of Pharmacology, 85(1): 60-69, 2001.
Higashi et al., "Autologous Bone-Marrow Mononuclear Cell Implantation Improves Endothelium-Dependent Vasodilation in Patients With Limb Ischemia", *Circulation*, 109:1215-1218 (2004).
Hino et al. "A Long-Term Culture of Human Hepatocytes Which Show a High Growth Potential and Express Their Differentiated Phenotypes", Biochemical and Biophysical Research Communications, 256(1): 184-191, 1999, Abstract.
Hirase et al. "Anemia and Neutropenia in a Case of Copper Deficiency: Role of Copper in Normal in Hematopiesis", Acta Haematology, 87(4): 195-197, 1992.
Hirose et al. "Identification of a Transposon-Related RNA Down-Regulated by Retinoic Acid in Embryonal Carcinoma and Embryonic Stem Cells", Experimental Cell Research, 221(2): 294-300, 1995. Abstract.
Hmama et al. "1-Alpha, 25-Dihydroxyvitamin D3-Induced Myeloid Cell Differentiation Is Regulated by a Vitamin D Receptor-Phospatidylinositol 3-Kinase Signaling Complex", Journal of Experimental Medicine, 190(11): 1583-1594, 1999.
Hoffman et al. "Zinc-Induced Copper Deficiency", Gastroenterology, 94(2): 508-512, Feb. 1988. Abstract.
Hofmeister et al. "Ex Vivo Expansion of Umbilical Cord Blood Stem Cells for Transplantation: Growing Knowledge From the Hematopoietic Niche", Bone Marrow Transplantation, 39: 11-23, 2007.
Holleman "Triethylene Tetramine, CAS No. 112-24-3", Chemical Hazard Information Profile Draft Report, 1982. Abstract.
Hoogenboom et al. "By-Passing Immunisation. Human Antibodies From Synthetic Repertoires of Germline $V_H$ Gene Segments Rearranged In Vitro", Journal of Molecular Biology, 227: 381-388, 1992.
Hori et al. "Growth Inhibitors Promote Differentiation of Insulin-Producing Tissue From Embryonic Stem Cells", Proc. Natl. Acad. Sci. USA, 99(25): 16105-16110, 2002.
Hottinger et al. "The Copper Chelator D-Penicillamine Delays Onset of Disease A Extends Survival in a Transgenic Mouse Model of Familial Amyotrophic Lateral Sclerosis", European Journal of Neuroscience, 9(7): 1548-51, 1997. Abstract.
Howard et al. "Formation and Hydrolysis of Cyclic ADP-Ribose Catalyzed by Lymphocyte Antigen CD38", Science, 262(5136): 1056-1059, 1993, Abstract.
Huang et al. "Differentiation of Human U937 Promonocytic Cells Is Impaired by Moderate Copper Deficiency", Experimental Biology and Medicine, 226(3): 222-228, 2001.
Huber et al. "Retroviral-Mediated Gene Therapy for the Treatment of Hepatocellular Carcinoma: An Innovative Approach for Cancer Therapy", Proc. Natl. Acad. Sci. USA, 88: 8039-8043, 1991.
Hutvágner et al. "RNAi: Nature Abhors a Double-Strand", Current Opinion in Genetics & Development, 12: 225-232, 2002.
Hwu et al. "Functional and Molecular Characterization of Tumor-Infiltrating Lymphocytes Transduced With Tumor Necrosis Factor-? cDNA for the Gene Therapy of Cancer in Humans", The Journal of Immunology, 150(9): 4104-4115, 1993.
Inbar et al. "Localization of Antibody-Combining Sites Within the Variable Portions of Heavy and Light Chains", Proc. Natl. Acad. Sci. USA, 69(9): 2659-2662, 1972.
Itoh et al. "Inhibition of Urokinase Receptor (uPAR) Expression by RNA-Cleaving Catalytic DNA (DNAzyme) Containing Antisense uPAR", Molecular Therapy, 5(5/Part 2): S134, 2002.
Jelinek et al. "Novel Bioreactors for the Ex Vivo Cultivation of Hematopoietic Cells", English Life Science, 2(1): 15-18, 2002.
Jiang et al. "Phosphatidylinositol 3-Kinase Signaling Mediates Angiogenesis and Expression of Vascular Endothelial Growth Factor in Endothelial Cells", PNAS, 97(4): 1749-1753, 2000.
Johnson et al. "Synthesis and Biological Activity of High-Affmity Retinoic Acid Receptor Antagonists", Bioorganic & Medicinal Chemistry, 7(7): 1321-1338, 1999.
Johnson et al. "The Cytokines IL-3 and GM-CSF Regulate the Transcriptional Activity of Retinoic Acid Receptors in Different In Vitro Models of Myeloid Differentiation", Blood, 99(3): 746-753, 2002.
Jones et al. "Replacing the Complementarity-Determining Regions in a Human Antibody With Those From a Mouse", Nature, 321: 522-525, 1986.
Kang et al. "Retinoic Acid and Its Receptors Repress the Expression and Transactivation Functions of Nur77: A Possible Mechanism for the Inhibition of Apoptosis by Retinoic Acid", Experimental Cell Research, 256: 545-554, 2000.
Kastner et al. "Positive and Negative Regulation of Granulopoiesis by Endogenous RARalpha", Blood, 97(5): 1314-1320, 2001. Abstract.
Kaufman et al. "Translational Efficency of Polycistronic mRNAs and Their Utilization to Express Heterologous Genes in Mammalian Cells", The EMBO Journal, 6(1): 187-193, 1987.
Kawa et al. "Stem Cell Factor and/or Endothelin-3 Dependent Immortal Melanoblast and Melanocyte Populations Derived From Mouse Neural Crest Cells", Pigment Cell Research, 13(Suppl.8): 73-80, 2000.
Kay et al. "Hepatic Gene Therapy: Persistent Expression of Human ?1-Antitrypsin in Mice After Direct Gene Delivery In Vivo", Human Gene Therapy, 3: 641-647, 1992.
Keith et al. "Multicomponent Therapeutics for Networked Systems", Nature Reviews: Drug Discovery, 4: 1-8, 2005.
Kern et al., "Comparative Analysis of Mesenchymal stem cells from Bone Marrow, Umbilical Cord Blood, or Adipose Tissue", *Stem Cells*, 24:1294-1301 (2006).
Khachigian "DNAzymes: Cutting a Path to a New Class of Therapeutics", Current Opinion in Molecular Therapeutics, 4(2): 119-121, 2002.
Kim "Differentiation and Identification of the Two Catalytic Metal Binding Sites in Bovine Lens Leucine Aminopeptidase by X-Ray Crystallography", Proc. Natl. Acad. Sci. USA, 90(11): 5006-5010, 1993.
Kishimoto et al. "Molecular Mechanism of Human CD38 Gene Expression by Retinoic Acid. Identification of Retinoic Acid Response Elemen in the First Intron", Journal of Biological Chemistry, 273(25): 15429-15434, 1998.
Kitanaka, et al., "CD38 ligation in human B cell progenitors triggers tyrosine phosphorylation of CD19 and association of CD19 with lyn and phosphatidylinositol 3-kinase.",*J. Immunol.*, 159(1):184-192 (1997).
Kizaki et al. Regulation of Manganese Superoxide Dismutase and Other Antioxidant Genes in Normal and Leukemic Hematopoietic Cells and Their Relationship to Cytotoxicity by Tumor Necrosis Factor, Blood, 82(4): 1142-1150, 1993.
Kobari et al. "CD133+ cell selection is an alternative to CD34+ cell selection for ex vivo expansion of hematopoietic stem cells.", *J. Hematother Stem Cell Res*. 2001; 10(2):273-81.
Kocher et al. "Neovascularization of Ischemic Myocardium by Human Bone-Marrow-Derived Angioblasts Prevents Cardiomyocyte Apoptosis, Reduces Remodeling and Improves Cardiac Function", Nature Medicine, 7(4): 430-436, 2001.

(56) References Cited

OTHER PUBLICATIONS

Köhler et al. "Defining Optimum Conditions for the Ex Vivo Expansion of Human Umbilical Cord Blood Cells. Influences of Progenitor Enrichment, Interference With Feeder Layers, Early-Acting Cytokines and Agitation of Culture Vessels", Stem Cells, 17(1: 19-24, 1999.

Kohroki et al. "Induction of Differentiation and Apoptosis by Dithizone in Human Myeloid Leukemia Cell Lines", Leukemia Research, 22(5): 405-412, 1998.

Koizumi et al. "Large Scale Purification of Human Blood CD34+ Cells From Cryopreserved Peripheral Blood Stem Cells, Using a Nylon-Fiber Syringe System and Immunomagnetic Microspheres", Bone Marrow Transplantation, 26: 787-793, 2000.

Krause et al. "Multi-Organ, Multi-Lineage Engraftment by a Single Bone Marrow-Derived Stem Cell", Cell, 105(3): 369-377, 2001. Abstract.

Kronenwett et al. "Oligodeoxyribonucleotide Uptake in Primary Human Hematopoietic Cells Is Enhanced by Cationic Lipids and Depends on the Hematopoietic Cell Subset", Blood, 91(3): 852-862, 1998.

Ku et al. "Committing Embryonic Stem Cells to Early Endocrine Pancreas In Vitro", Stem Cells, 22: 1205-1217, 2004.

Kumagai et al. "Ligation of CD38 Suppresses Human B Lymphopoiesis", Journal of Experimental Medicine, 181(3): 1101-1110, 1995.

Labrecque et al. "Impaired Granulocytic Differentiation in Vitro in Hematopoietic Cells Lacking Retinoic Acid Receptors $\alpha 1$ and $\gamma$", Blood, 92(2): 607-615, 1998.

Lagasse et al. "Purified Hematopoietic Stem Cells Can Differentiate Into Hepatocytes In Vivo", Nature Medicine, 6(11): 1229-1234, 2000. Abstract.

Lam et al. "Preclinical Ex Vivo Expansion of Cord Blood Hematopoietic Stem and Progenitor Cells: Duration of Culture; the Media, Serum Supplements, and Growth Factors Used; and Engraftment in NOD/SCID Mice", Transfusion, 41(12): 1567-1576, 2001. Abstract.

Lange et al. "Biological and Clinical Advances in Stem Cell Expansion", Leukemia, 10: 943-945, 1996.

Lapidot et al. "Cytokine Stimulation of Multilineage Hematopoiesis From Immature Human Cells Engrafted in SCID Mice", Science, 255: 1137-1141, 1992. Abstract.

Larrick et al. "PCR Amplification of Antibody Genes", Methods: A Companion to Methods in Enzymology, 2(2): 106-110, 1991.

Lassila et al. "Role for Lys-His-Gly-NH2 in Avian and Murine B Cell Development", Cellular Immunology, 122(2): 319-328, 1989.

Lau et al. "A Peptide Molecule Mimicking the Copper (II) Transport Site of Human Serum Albumin", Journal of Biological Chemistry, 249(18): 5878-5884, 1974.

Lavigne et al. "Enhanced Antisense Inhibition of Human Immunodeficiency Virus Type 1 in Cell Cultures by DLS Delivery System", Biochemical and Biophysical Research Communications, 237: 566-571, 1997.

Lawlor et al. "Coordinate Control of Muscle Cell Survival by Distinct Insulin-Like Growth Factor Activated Signaling Pathways", The Journal of Cell Biology, 151(6): 1131-1140, 2000. p. 1133-1139.

Lee et al. "Effect of Vitamin D3 Analog, EB1089, on Hematopoietic Stem Cells From Normal and Myeloid Leukemic Blasts", Leukemia, 10: 1751-1757, 1996.

Lemarchand et al. "Adenovirus-Mediated Transfer of a Recombinant Human $\alpha 1$-Antitrypsin cDNA to Human Endothelial Cells", Proc. Natl. Acad. Sci. USA, 89: 6482-6486, 1992.

Leslie et al. "An Activating Mutation in the Kit Receptor Abolishes the Stroma Requirement for Growth of ELM Erythroleukemia Cells, But Does Not Prevent Their Differentiation in Response to Erythropoietin", Blood, 92(12): 4798-4807, 1998.

Lewandowski et al. "Phosphatidylinositol 3-Kinases Are Involved in the All-Trans Retinoic Acid-Induced Upregulation of CD38 Antigen on Human Haematopoietic Cells", British Journal of Hematology, 118(2): 535-544, 2002. Fig.8.

Li et al. "Activation of Phosphatidylinositol-3 Kinase (PI-3K) and Extracellular Regulated Kinases (Erkl/2) Is Involved in Muscarinic Receptor-Mediated DNA Synthesis in Neural Progenitor Cells", The Journal of Neuroscience, 21(5): 1569-1579, 2001. p. 1572-1578.

Lianguzova et al. "PI3-Kinase Inhibitors LY294002 and Wortmannin Have Different Effects on Proliferation of Murine Embryonic Stem Cells", Tsitologiia, 48(7): 560-568, 2006. Abstract.

Lonberg et al. "Antigen-Specific Human Antibodies From Mice Comprising Four Distinct Genetic Modifications", Nature, 368: 856-859, 1994.

Lonberg et al. "Human Antibodies From Transgenic Mice", International Review in Immunology, 13: 65-93, 1995.

Lovejoy et al. "Novel 'Hybrid' Iron Chelators Derived From Aroylhydrazones and Thiosemicarbazones Demonstrate Delective Antiproliferative Activity Against Tumor Cells", Blood, 100(2): 666-676, 2002.

Lu et al. "Intravenous Administration of Human Umbilical Cord Blood Reduces Neurological Deficit in the Rat After Traumatic Brain Injury", Cell Transplant., 11(3): 275-281, 2002. Abstract.

Luft "Making Sense Out of Antisense Oligodeoxynucleotide Delivery: Getting There Is Half the Fun". J. Mol. Med, p. 75-76. 1998.

Lutton et al. "Zinc Porphyrins: Potent Inhibitors of Hematopoieses in Animal and Human Bone Marrow", Proc. Natl. Acad. Sci. USA, 94: 1432-1436, 1997.

Ma, et al., "Inhibition of phosphatidylinositol 3-kinase causes apoptosis in retinoic acid differentiated hl-60 leukemia cells.", *Cell Cycle*, 3(1):67-70 (2004).

Mader et al. "A Steroid-Inducible Promoter for the Controlled Overexpression of Cloned Genes in Eukaryotic Cells", Proc. Natl. Acad. Sci. USA, 90: 5603-5607, 1993.

Madlambayan et al. "Controlling Culture Dynamics for the Expansion of Hematopoietic Stem Cells", Journal of Hematotherapy and Stem Cell Research, 10(4): 481-492, 2001. Abstract.

Manome et al. "Coinduction of C-Jun Gene Expression and Internucleosomal DNA Fragmentation by Ionizing Radiation", Biochemistry, 32: 10607-10613, 1993.

Mar et al. "A Conserved CATTCCT Motif Is Required for Skeletal Muscle-Specific Activity of the Cardiac Troponin T Gene Promoter", Proc. Natl. Acad. Sci. USA, 85: 6404-6408, 1988.

Marcinkowska "Does the Universal 'Signal Transduction Pathway of Differentiation' Exist? Comparison of Different Cell Differentiation Experimental Models With Differentiation of HL-60 Cells in Response to 1,25-Dihydroxyvitamin D3", Postepy Higieny i Medycyny Doświadczalnej, 53(2): 305-313, 1999. Abstract.

Marks et al. "By-Passing Immunization. Human Antibodies From V-Gene Libraries Displayed on Phage", Journal of Molecular Biology, 222: 581-597, 1991.

Marks et al. "By-Passing Immunization: Building High Affinity Human Antibodies by Chain Shuffling", Bio/Technology, 10: 779-783, 1992.

Martelli et al. "Transplants Across Human Leukocyte Antigen Barriers", Seminars in Hematology, 39(1): 48-56, 2002.

Matuoka et al. "A Positive Role of Phosphatidylinositol 3-Kinase in Aging Phenotype Expression in Cultured Human Diploid Fibroblasts", Arch. Gerontol. Geriatry, 36:203-219, 2003.

Matzner et al. "Bone Marrow Stem Cell Gene Therapy of Arylsulfatase A-Deficient Mice, Using an Arylsulfatase a Mutant That Is Hypersecreted From Retrovirally Transduced Donor-Type Cells", Human Gene Therapy, 12: 1021-1033, 2001.

McLaughlin et al. "Adeno-Associated Virus General Transduction Vectors: Analysis of Proviral Structures", Journal of Virology, 62(6): 1963-1973, 1988.

McNiece et al. "Action of Interleukin-3, G-CSF on Highly Enriched Human Hematopoietic Preogenitor Cells: Synergistic Interaction of GM-CSF Plus G-CSF", Blood, 74: 110-114, 1989.

McNiece et al. "CD34+ Cell Selection From Frozen Cord Blood Products Using the Isolex 300i and CliniMACS CD34 Selection Devices", Journal of Hematotherapy, 7: 457-461, 1998.

McNiece et al., "Ex vivo Expansion of Cord Blood Mononuclear Cells on Mesenchymal Stem Cells", *Cytotherapy*, 6(4):311-317 (2004).

Mehta et al. "Human CD38, A Cell-Surface Protein With Multiple Functions", The FASEB Journal, 10(12): 1408-1417, 1996.

(56) References Cited

OTHER PUBLICATIONS

Mehta et al. "Involvement of Retinoic Acid Receptor-α-Mediated Signaling Pathway in Induction of CD38 Cell-Surface Antigen", Blood, 89(10): 3607-3614, 1997.

Mehta et al. "Retinoid-Mediated Signaling Pathways in CD38 Antigen Expression in Myeloid Leukemia Cells", Leukemia and Lymphoma, 32(5/6): 441-449, 1999.

Meissner et al. "Development of a Fixed Bed Bioreactor for the Expansion of Human Hematopoietic Progenitor Cells", Cytotechnology, 30: 227-234, 1999.

Merck & Co. "The Merck Index, An Encyclopedia of Chemicals, Drugs and Biologicals", 10th Ed.(3742): 549, 1983.

Mezey et al. "Turning Blood Into Brain: Cells Bearing Neuronal Antigens Generated In Vivo From Bone Marrow", Science, 290(5497): 1779-1782, 2000.

Migliaccio et al. "Long-Term Generation of Colony-Forming Cells in Liquid Culture of CD34+ Cord Blood Cells in the PResence of Recombinant Human Stem Cell Factor", Blood, 79: 2620-2627, 1992.

Miller "Progress Toward Human Gene Therapy", Blood, The Journal of the American Society of Hematology, 76(2): 271-278, 1990.

Miller et al. "Expansion In Vitro of Adult Murine Hematopoietic Stem Cells With Transplantable Lympho-Myeloid Reconstituting Ability", Proc. Natl. Acad. Sci. USA, 94: 13648-13653, 1997.

Mills et al. "Regulation of Retinoid-Induced Differentiation in Embryonal Carcinoma PCC4.Aza 1 R Cells: Effects of Retinoid-Receptor Selective Ligands", Cell Growth Differ., 7(3): 327-337, 1996. Abstract.

Mood, et al., "Contribution of JNK, Mek, Mos and PI-3K signaling to GVBD in *Xenopus oocytes.*", Cell. Signalling, 16:631-642 (2004).

Moore et al. "Ex Vivo Expansion of Cord Blood-Devined Stem Cells and Progenitons", Blood Cells, 20: 468-481, 1994.

Morier-Teissier et al. "Synthesis and Antitumor Properties of an Anthraquinone Bisubstituted by the Copper Chelating Peptide Gly-Gly-L-His", Journal of Medical Chemistry, 36: 2084-2090, 1993. Abstract.

Morimoto et al. "EDTA Induces Differentiation and Suppresses Proliferation of Promyelotic Leukemia Cell Line HL-60—Possible Participation of Zinc-", Biochemistry International, 28(2): 313-321, 1992.

Morosetti et al. "Infrequent Alterations of the RARα Gene in Acute Myelogenous Leukemias, Retinoic Acid-Resistant Acute Promyelocytic Leukemias, Myelodysplastic Syndromes, and Cell Lines", Blood, 87(10): 4399-4403, May 15, 1996.

Morrison "Success in Specification", Nature, 368(6474): 812-813, 1994.

Morrison et al. "Identification of a Lineage of Multipotent Hematopoietic Progenitors", Development, 124: 1929-1939, 1997.

Morrison et al. "The Long-Term Repopulating Subset of Hematopoietic Stem Cell Is Deterministic and Isolatable by Phenotype", Immunity, 1: 661-673, 1994. Abstract.

Mueller et al. "Heterozygous PU.1 Mutations Are Associated With Acute Myeloid Leukemia", Blood, 100(3): 998-1007, 2002.

Muench et al. "Interactions Among Colony-Stimulating Factors, IL-1β, IL-6, and Kit-Ligand in the Regulation of Primitive Murine Hematopoietic Cells", Experimental Hematology, 20: 339-349, 1992.

Mulloy et al. "Maintaining the self-renewal and differentiation potential of human CD34+ hematopoietic cells using a single genetic element." Blood, 102(13):4369-76, 2003.

Munshi et al. "Evidence for a Causal Role of CD38 Expression in Granulocytic Differentiation of Human HL-60 Cells", The Journal of Biological Chemistry, 277(51): 49453-49458, 2002.

Muramatsu et al. "Reversible Integration of the Dominant Negative Retinoid Receptor Gene for Ex Vivo Expansion of Hematopoietic Stem/Progenitor Cells", Biochemical & Biophysical Research Communications, 285(4): 891-896, 2001. Abstract.

Murray et al. "Modulation of Murine Lymphocyte and Macrophage Proliferation by Parenteral Zinc", Clinical and Experimental Immunology, 53(3): 744-749, 1983.

Murray et al. "Thrombopoietin, Flt3, and Kit Ligands Together Suppress Apoptosis of Human Mobilized CD34+ Cells and Recruit Primitive CD34+Thy-1+ Cells Into Rapid Division", Experimental Hematology, 27: 1019-1028, 1999.

Murry et al., "Haematopoietic Stem Cells Do Not Transdifferentiate Into Cardiac Myocytes in Myocardial Infarcts", *Nature*, 428:664-668 (2004).

Muzyczka "Use of Adeno-Associated Virus as a General Transduction Vector for Mammalian Cells", Current Topics in Microbiology and Immunology, 158: 97-129, 1992.

Narita et al. "Cardiomycyte Differentiation by GATA-4-Deficient Embryonic Stem Cells", Development, 122(19): 3755-3764, 1996.

Neuberger "Generating High-Avidity Human Mabs in Mice", Nature Biotechnology, 14: 826, 1996.

Nicolau et al. "Liposomes as Carriers for In Vivo Gene Transfer and Expression", Methods in Enzymology, 149(Chap.16): 157-176, 1987.

Ohishi et al. "Delta-1 Enhances Marrow and Thymus Repopulating Ability of Human CD34+CD38-Cord Blood Cells", The Journal of Clinical Investigation, 110(8): 1165-1174, 2002.

Okazaki et al. "Characteristics and Partial Purification of a Novel Cytosolic, Magnesium-Independent, Neutral Sphingomyelinase Activated in the Early Signal Transduction of 1?,25-Dihydroxyvitamin D3-Induced HL-60 Cell Differentiation", The Journal of Biological Chemistry, 269(6): 4070-4077, 1994.

Okuno et al. "Differential regulation of the human and murine CD34 genes in hematopoietic stem cells." Proc Natl Acad Sci U S A., 99(9):6246-51, 2002.

Olivares et al. "Copper As an Essential Nutrient", The American Journal of Clinical Nutrition, 63: 791S-796S, 1996. Abstract.

Orlic et al. "Exogenous Hematopoietic Stem Cells Can Regenerate Infarcted Myocardium", Circulation, 102: 2672, 2000.

Orlic et al. "Mobilized Bone Marrow Cells Repair the Infarcted Heart, Improving Function and Survival", Proc. Natl. Acad. Sci. USA, 98(18): 10344-10349, 2001.

Orlic et al. "Transplanted Adult Bone Marrow Cells Repair Myocardial Infarcts in Mice", Annals of the New York Academy of Sciences, 938: 221-230, 2001. Abstract.

Osawa et al. "Long-Term Lymphohematopoietic Reconstitution by a Single CD34+-Low/Negative Hematopoietic Stem Cell", Science, 273(5272): 242-245, 1996.

Ostrakhovitch et al. Copper Ions Strongly Activate the Phosphoinositide-3-Kinase/Akt Pathway Independent of the Generation of Reactive Oxygen Species, Archives of Biochemistry and Biophysics, 397(2): 232-239, 2002. p. 235, col. 1, Paragraph 4-col.2, Paragraph 2.

Pack et al. "Improved Bivalent Miniantibodies, With Identical Avidity as Whole Antibodies, Produced by High Cell Density Fermentation of *Escherichia coli*", Bio/Technology, 11: 1271-1277, 1993.

Paling et al. "Regulation of Embryonic Stem Cell Self-Renewal by Phosphoinositide 3-Kinase-Dependent Signaling", The Journal of Biological Chemistry, 279(46): 48063-48070, 2004.

Park, et al., "Phosphatidylinositol 3-kinase regulates PMA-induced differentiation and superoxide production in HL-60 cells.", *Immunopharmacol. Immunotoxicol.*, 24(2):211-226 (2002).

Pei et al. "Bioreactors Mediate the Effectiveness of Tissue Engineering Scaffolds", The FASEB Journal, 16: 1691-1694, 2002.

Peled et al. "Cellular Copper Content Modulates Differentiation and Self-Renewal in Cultures of Cord Blood-Derived CD34+ Cells", British Journal of Haematology, 116(3): 655-661, 2002.

Peled et al., "Chelatable Cellular Copper Modulates Differentiation and Self-Renewal of Cord Blood-Derived Hematopoietic Progenitor Cells", Exp Hematol, 33:1092-1100 (2005).

Peled et al. "Copper Chelators Sustain Long-Term Expansion of Cord-Blood CD 34+ Cultures Initiated With IL-3 and G-CSF—Late Acting, Differentiation-Inducing Cytokines", Blood, 96(1): 773a, 2000. Abstract # 3343.

Peled et al. "Identification of a Serum-Derived Differentiation-Inducing Activity as the Copper-Binding Protein Ceruloplasmin", Blood, 92(10, Suppl.1, Part 1-2): 618A-619A, 1998. Abstract.

Peled et al. "Linear Polyamine Copper Chelator Tetraethylenepentamine Augments Long-Term Ex Vivo Expansion

(56) References Cited

OTHER PUBLICATIONS of Cord Blood-Derived CD34+ Cells and Increases Their Engraftment Potential in NOD/SCID Mice", Experimental Hematology, 32: 547-555, 2004.

Peled et al. "Regulation of Long-Term Expansion of Hemopoietic Stem/Progenitor Cells (HPC) by Intracellular Copper Content", Blood, 96(11/Pt.1): 776a-777a, 2000.

Peled et al. "Copper chelators enable long term CFU and CD34+ cells expansions in cultures initiated with the entire mononuclear cell (MNC) fraction.", Blood, 100 (11), 2002. Abstract # 4076.

Pera MF. 2001. Human pluripotent stem cells: a progress report. Curr Opin Gen Devel 11:595-599.

Percival "Copper and Immunity", American Journal of Clinical Nutrition, 67(5 Suppl.): 1064S-1068S, 1998. p. 1066, 1-h col., § 2-r-h col., § 2.

Percival "Neutropenia Caused by Copper Deficiency: Possible Mechanism of Action", Nutrition Reviews, 53(3): 59-66, 1995.

Percival et al. "Copper Is Required to Maintain Cu/Zn-Superoxide Dismutase Activity During HL-60 Cell Differentiation", Proc. Soc. Exp. Biol. Med., 203: 78-83, 1993.

Percival et al. "HL-60 Cells Can Be Made Copper Deficient by Incubating With Tetraethylenepentamine 1,2,3", Journal of Nutrition, 122(12): 2424-2429, 1992.

Perrotti et al. "Overexpression of the Zinc Finger Protein MZF1 Inhibits Hematopoietic Development From Embryonic Stem Cells: Correlation With Negative Regulation of CD34 and C-MYB Promoter Activity", Molecular and Cellular Biology, 15(11): 6075-6087, 1995.

Peters et al. "Long-Term Ex Vivo Expansion of Human Fetal Liver Primitive Haematopoietic Progenitor Cells in Stroma-Free Cultures", British Journal of Haematology, 119: 792-802, 2002.

Petersen et al. "Bone Marrow as a Potential Source of Hepatic Oval Cells", Science, 284(5417): 1168-1170, 1999. Abstract.

Petersen et al. "Hepatic Oval Cells Express the Hematopoietic Stem Cell Marker Thy-1 in the Rat", Hepatology, 27(2): 433-445, 1998.

Petti et al. "Complete Remission Through Blast Cell Differentiation in PLZF/RARα-Positive Acute Promyelocytic Leukemia: In Vitro and In Vivo Studies", Blood, 100(3): 1065-1067, 2002.

Petzer et al. "Differential Cytokine Effects on Primitive (CD34+CD38−) Human Hematopoietic Cells: Novel Responses to Flt3-Ligand and Thrombopoietin", Journal of Experimental Medicine, 183: 2551-2558, 1996.

Petzer et al., "Self-Renewal of Primitive Human Hematopoietic Cells (Long-Term-Culture-Initiating Cells) in vitro and Their Expansion in Defined Medium", *Proc Natl Acad Sci USA*, 93:1470-1474 (1996).

Piacibello et al. "Extensive Amplification and Self-Renewal of Human Primitive Hematopoietic Stem Cells From Cord Blood", Blood, 89(8): 2644-2653, 1997.

Pickart et al. "Growth Modulating Plasma Tripeptide May Function by Facilitating Copper Uptake Into Cells", Nature, 288(18/25): 715-717, 1980.

Podesta et al. "Extracellular Cyclic ADP-Ribose Increases Intracellular Free Calcium Concentration and Stimulates Proliferation of Human Hematopoietic Progenitors", FASEB Journal, 14(5): 680-690, 2000. Fig.1.

Podestá et al. "Cyclic ADP-Ribose Generation by CD38 Improves Human Hemopoietic Stem Cell Engraftment Into NOD/SCID Mice", The FASEB Journal, 17: 310-312, 2003.

Porter "The Hydrolysis of Rabbit γ-Globulin and Antibodies With Crystalline Papain", Biochemical Journal, 73: 119-126, 1959.

Porter et al. "Graft-Versus-Leukemia Effect of Allogeneic Bone Marrow Transplantation and Donor Mononuclear Cell Infusions", Cancer Treatment & Research, 77: 57-85, 1997. Abstract.

Presta "Antibody Engineering", Current Opinion in Structural Biology, 2: 593-596, 1992.

Puccetti et al. "AML-Associated Translocation Products Block Vitamin D3-Induced Differentiation by Sequestering the Vitamin D3 Receptor", Cancer Research, 62: 7050-7058, 2002.

Punzel et al. "The Type of Stromal Feeder Used in Limiting Dilution Assays Influences Frequency and Maintenance Assessment of human Long-Term Culture Initiating Cells", Leukemia, 13: 92-97, 1999.

Purdy et al. "Large Volume Ex Vivo Expansion of CD34+-Positive Hematopoietic Progenitor Cells for Transplantation", Journal of Hematotherapy, 4: 515-525, 1995.

Purton et al. "All-Trans Retinoic Acid Delays the Differentiation of Primitive Hematopoietic Precursors (lin⁻c-kit+sca-1+) While Enhancing the Terminal Maturation of Committed Granulocyte/Monocyte Progenitors", Blood, 94(2); 483-495, 1999.

Purton et al. "All-Trans Retinoic Acid Enhances the Long-Term Repopulating Activity of Cultured Hematopoietic Stem Cells", Blood, 95(2): 470-477, 2000. Abstract.

Purton et al. "All-Trans Retinoic Acid Facilitates Oncoretrovirus-Mediated Transduction of Hematopoietic Repopulating Stem Cells", J. Hematother. Stem Cell Res., 10(8): 815-825, 2001. Abstract.

Quantin et al. "Adenovirus as an Expression Vector in Muscle Cells In Vivo", Proc. Natl. Acad. Sci. USA, 89: 2581-2584, 1992.

Rajur et al. "Covalent Protein-Oligoneucleotide Conjugates for Efficient Delivery of Antisense Molecules", Bioconjugate Chemistry, 8(6): 935-940, 1997.

Ramsfjell et al. "Distinct Requirements for Optimal Growth and In Vitro Expansion of Human CD34+CD38−Bone Marrow Long-Term Culture-Initiating Cells (LTC-IC), Extended LTC-IC, and Murine In Vivo Long-Term Reconstituting Stem Cells", Blood, 94(12): 4093-4102, 1999.

Ratajczak et al. "Effect of Basic (FGF-2) and Acidic (FGF-1) Fibroblast Growth Factors on Early Haemopoietic Cell Development", British Journal of Hematology, 93: 772-782, 1996.

Ratajczak MZ et al., "Hunt for pluripotent stem cell—regenerative medicine search for almighty cell.", J Autoimmun 30: 151-162, 2008.

Reeves et al. "High Zinc Concentrations in Culture Media Affect Copper Uptake and Transport in Differentiated Human Colon Adenocarcinoma Cells", Journal of Nutrition, 126(6): 1701-1712, 1996. Abstract.

Reid et al. "Interactions of Tumor Necrosis Factor With Granulocyte-Macrophage Colony-Stimulating Factor and Other Cytokines in the Regulation of Dendritic Cell Growth In Vitro From Early Bipotent CD34+ Progenitors in Human Bone Marrow", Journal of Immunology, 149(8): 2681-2688, 1992. Abstract.

Reya, T., "Regulation of Hematopoietic Stem Cell Self-Renewal", *Rec Prog Horm Res*, 58:283-295 (2003).

Reyes et al. "Origin of Endothelial Progenitors in Human Postnatal Bone Marrow", Journal of Clinical Investigation, 109: 337-346, 2002.

Riechmann et al. "Reshaping Human Antibodies for Therapy", Nature, 332: 323-327, 1988.

Roberts. "Mesenchymal Stem Cells", Vox Sanguinis, 87(Suppl. 2): s38-s41, 2004.

Robinson et al., "Superior Ex vivo Cord Blood Expansion Following Co-Culture With Bone Marrow-Derived Mesenchymal Stem Cells", *Bone Marrow Transplant.*, 37:359-366 (2006).

Rosenfeld et al. "Adenovirus-Mediated Transfer of a Recombinant α1-Antitrypsin Gene to the Lung Epithelium In Vivo", Science, 252: 431-434, 1991.

Rosenfeld et al. "In Vivo Transfer of the Human Cystic Fibrosis Transmembrane Conductance Regulator Gene to the Airway Epithelium", Cell, 68: 143-155, 1992.

Ross et al. "Chelometric Indicators Titrations With the Solid-State Cupric Ion-Selective Electrode", Analytical Chemistry, 41(13): 1900-1902, 1969.

Rusten et al. "The RAR-RXR as Well as the RXR-RXR Pathway Is Involved Signaling Growth Inhibition of Human CD34+ Erythroid Progenitor Cells", Blood, 87(5): 1728-1736, 1996. Abstract.

Ryu et al. "Adenosine Triphosphate Induces Proliferation of Human Neural Stem Cells: Role of Calcium and P70 Ribosomal Protein S6 Kinase", Journal of Neuroscience Research, 72: 352-362, 2003.

Sammons et al. "Mechanisms Mediating the Inhibitory Effect of All-Trans Retinoic Acid on Primitive Hematopoietic Stem Cells in Human Long-Term Bone Marrow Culture", Stem Cells, 18(3): 214-219, 2000.

(56) References Cited

OTHER PUBLICATIONS

Samulski et al. "Helper-Free Stocks of Recombinant Adeno-Associated Viruses: Normal Integration Does Not Require Viral Gene Expression", Journal of Virology, 63(9): 3822-3828, 1989.
Santoro et al. "A General Purpose RNA-Cleaving DNA Enzyme", Proc. Natl. Acad. Sci. USA, 94: 4262-4266, 1997.
Sato et al. "In Vitro Expansion of Human Peripheral Blood CD34+ Cells", Blood, 82(12): 3600-3609, 1993.
Sauve et al. "Mechanism-Based Inhibitors of CD38: A Mammalian Cyclic ADP-Ribose Synthetase", Biochemistry, 41(26): 8455-8463, 2002.
Schechter et al. The Molecular Basis of Blood Diseases, p. 179-218, 1987.
Schmetzer et al. "Effect of GM-CSF, 1,25-Dihydroxycholecalciferol (Vit. D) and All-Trans-Retinocin Acid (ATRA) on the Proliferation and Differentiation of MDS-Bone Marrow (BM)-Cells In Vitro", Hematology, 2: 11-19, 1997.
Schwartz et al. "In Vitro Myelopoiesis Stimulated by Rapid Medium Exchange and Supplementation With Hematopoietic Growth Factors", Blood, 78(12): 3155-3161, 1991.
Seed "An LFA-3 cDNA Encodes a Phospholipid-Linked Membrane Protein Homologous to Its Receptor CD2", Nature, 329: 840-842, 1987.
Sekhar et al. "Retroviral Transduction of CD34-Enriched Hematopoietic Progenitor Cells Under Serum-Free Conditions", Human Gene Therapy, 7: 33-38, 1996.
Selden "Transfection Using DEAE-Dextran", Short Protocols in Molecular Biology, Unit 9.2: 9-9-9-11, 1984.
Selden et al. "Optimization of Transfection", Short Protocols in Molecular Biology, Unit 9.4: 262-263, 1984.
Sergeant et al. "Iron and Copper Requirements for Proliferation and Differentiation of a Human Promyelocytic Leukemia Cell Line (HL-60)", Journal of Cellular Physiology, 163(3): 477-485, 1995.
Shimakura et al. "Murine Stromal Cell Line HESS-5 Maintains Reconstituting Ability of Ex Vivo-Generated Hematopoietic Stem Cells From Human Bone Marrow and Cytokine-Mobilized Peripheral Blood", Stem Cells, 18: 183-189, 2000.
Shimizu et al. "Treatment and Management of Wilson's Disease", Pediatrics International, 41(4): 419-422, 1999. Abstract.
Sieff, et al., "Changes in cell surface antigen expression during hemopoietic differentiation.", Blood, 60(3):703-713 (1982).
Sigurdsson et al. "Copper Chelation Delays the Onset of Prion Disease", Journal of Biological Chemistry, 278(47): 46199-202, 2003.
Silvenoinen et al. "CD38 Signal Transduction in Human B Cell Precursors. Rapid Induction of Tyrosine Phosphorylation, Activation of Syk Tyrosine Kinase and Phosphorylation of Phospholipase C-Gamma and Phosphatidylinositol 3-Kinase", Journal of Immunology, 156(1): 100-107, 1996. Abstract.
Simon et al. "Copper Deficiency and Sideroblastic Anemia Associated With Zinc Ingestion", American Journal of Hematology, 28: 181-183, 1988.
Slavin et al. "Donor Lymphocyte Infusion: The Use of Alloreactive and Tumor-Reactive Lymphocytes for Immunotherapy of Malignant and Nonmalignant Diseases in Conjunction With Allogeneic Stem Cell Transplantation", Journal of Hematotherapy & Stem Cell Research, 11: 265-276, 2002.
Slavin et al. "Treatment of Leukemia by Alloreactive Lymphocytes and Nonmyeloablative Stem Cell Transplantation", Journal of Clinical Immunology, 22(2): 64-69, 2002.
Spencer et al. "Controlling Signal Transduction With Synthetic Ligands", Science, 262: 1019-1024, 1993.
Sprangrude et al. "Purification and Characterization of Mouse Hematopoietic Stem Cells", Science, 241(4861): 58-62, 1988. Abstract.
Suda et al. "A Study of Trientine Therapy in Wilson's Disease With Neurology Symptoms", No To Hattatsu, 25(5): 429-34, 1993. Abstract.
Szilvassy et al. "Differential Homing and Engraftment Properties of Hematopoetic Progenitor Cells From Murine Bone Marrow Mobilized Peripheral Blood Cells and Fetal Liver", Blood, 98(7): 2108-2115, 2001.
Takeshita et al. "Selective Stimulation by Ceramide of the Expression of the α Isoform of Retinoic Acid and Retinoid X Receptors in Osteoblastic Cells", Journal of Biological Chemistry, 275(41): 32220-32226, 2000.
Tashiro-Itoh et al. "Metallothionein Expression and Concentrations of Copper and Zinc Are Associated With Tumor Differentiation in Hepatocellular Carcinoma", Liver, 17: 300-306, 1997.
Tateishi-Yuyama et al., "Therapeutic angiogenesis for patients with limb ischaemia by autologous transplantation of bone-marrow cells: a pilot study and a randomised controlled trial", *The Lancet*, 360:427-435 (2002).
Tateno et al., "Long-term cultivation of adult rat hepatocytes that undergo multiple cell divisions and express normal parenchymal phenotypes.", *Am. J. Pathol.*, 148(2):383-392 (1996).
Tetraethylene Pentamine DOD Hazardous Material Information; 6810-00F017710 (1991).
Thiotepa Product Identification Sheet; Thiotepa; EM Science, 6505-01-047-3872 (1990).
Todisco et al. "CD38 Ligation Inhibits Normal and Leukemic Myelopoiesis", Blood, 95(2): 535-542, 2000. Abstract.
Tratschin et al. "A Human Parvovirus, Adeno-Associated Virus, as a Eucaryotic Vector: Transient Expression and Encapsidation of the Procaryotic Gene for Chloramphenicol Acetyltransferase", Molecular and Cellular Biology, 4(10): 2072-2081, 1984.
Tratschin et al. "Adeno-Associated Virus Vector for High-Frequency Integration, Expression, and Rescue of Genes in Mammalian Cells", Molecular and Cellular Biology, 5(11): 3251-3260, 1985.
Tratschin et al. "Genetic Analysis of Adeno-Associated Virus: Properties of Deletion Mutants Constructed In Vitro and Evidence for An Adeno-Associated Virus Replication Function", Journal of Virology, 51(3): 611-619, 1984.
Triethylenetetramine Product Identification Sheet; TETA, TX1235; EM Science, 6810-00N052879 (1991).
Tuba et al. "Synthesis and Structure—Activity Relationships of Neuromuscular Blocking Agents", Current Medicinal Chemistry, 9: 1507-1536, 2002.
Turnpenny L et al., "Evaluating human embryonic germ cells: concord and conflict as pluripotent stem cells.", Stem Cells 24: 212-220, 2006.
Ueno et al. "A Novel Retinoic Acid Receptor (RAR)-Selective Antagonist Inhibits Differentiation and Apoptosis of HL-60 Cells: Implications of RAR?-Mediated Signals in Myeloid Leukemic Cells", Leukemia Research, 22(6): 517-525, 1998.
Van Beusechem et al. "Long-Term Expression of human Adenosine Deaminase in Rhesus Monkeys Transplanted With Retrovirus-Infected Bone-Marrow Cells", Proc. Natl. Acad. Sci. USA, 89: 7640-7644, 1992.
Verfaillie "Can Human Hematopoietic Stem Cells Be Cultured Ex Vivo?", Stem Cells, 12(5): 466-476, 1994. Abstract.
Verfaillie "Direct Contact Between Human Primitive Hematopoietic Progenitors and Bone Marrow Stroma Is Not Required for Long-Term In Vitro Hematopoiesis", Blood, 79(11): 2821-2826, 1992.
Verlinden et al. "Interaction of Two Novel 14-Epivitamin D3 Analogs With Vitamin D3 Receptor-Retinoid X Receptor Heterodimers on Vitamin D3 Response Elements", Journal of Bone and Mineral Research, 16(4): 625-638, 2001.
Vilensky et al. "British Anti-Lewisite (Dimercaprol): an Amazing History", Ann. Emerg. Med., 41(3): 378-83, 2003. Abstract.
Vlahos, et al., "A specific inhibitor of phosphatidylinositol 3-kinase, 2-(4-morpholinyl)-8-phenyl-4H-1-benzopyran-4-one (LY294002).", *J. Biol. Chem.*, 269(7):5241-5248 (1994).
Wagers et al., "Little Evidence for Developmental Plasticity of Adult Hematopoietic Stem Cells", Science, 297(5590):2256-2259 (2002). Abstract.
Wall et al. "Inhibition of the Intrinsic NAD+ Glycohydrolase Activity of CD38 by Carbocyclic NAD Analogues", Biochemical Journal, 335(3): 631-636, 1998.

(56) References Cited

OTHER PUBLICATIONS

Walton et al. "Prediction of Antisense Oligonucleotide Binding Affinity to a Structured RNA Target", Biotechnology and Bioengineering, 65(1): 1-9, 1999.
Wang et al. "In Vitro Culture of Umbilical Cord Blood MNC and CD34+ Selected Cells", Sheng Wu Gong Cheng Xue Bao, 18(3): 343-347, 2002. Abstract.
Wang et al. "PH-Sensitive Immunoliposomes Mediate Target-Cell-Specific Delivery and Controlled Expression of a Foreign Gene in Mouse", Proc. Natl. Acad. Sci. USA, 84: 7851-7855, 1987.
Wasa et al. "Copper Deficiency With Pancytopenia During Total Parenteral Nutrition", Journal of Parenteral and Enteral Nutrition, 18(2): 190-192, 1994.
Weissmann "Translating Stem and Progenitor Cell Biology to the Clinic: Barriers and Opportunities", Science, 287(5457): 1442-1446, 2000. Abstract.
Wendling et al. "Retinoid X Receptor Are Essential for Early Mouse Development and Placentogenesis", Proc. Natl. Acad. Sci. USA, 96(2): 547-551, 1999.
Whitlow et al. "Single-Chain Fv Proteins and Their Fusion Proteins", Methods: A Companion to Methods in Enzymology, 2(2): 97-105, 1991.
Wick et al. "New Ways in Hepatocyte Cultures: Cell Immobilisation Technique", ALTEX, 14(2): 51-56, 1997. Abstract.
Wilson et al. "Hepatocyte-Directed Gene Transfer In Vivo Leads to Transient Improvement of Hypercholesterolemia in Low Density Lipoprotein Receptor-Deficient Rabbits", The Journal of Biological Chemistry, 267(2): 963-967, 1992.
Wilson et al. "Retrovirus-Mediated Transduction of Adult Hepatocytes", Proc. Natl. Acad. Sci. USA, 85: 3014-3018, 1988.
Wolff et al. "Direct Gene Transfer Into Mouse Muscle In Vivo", Science, 247: 1465-1468, 1990.
Wondisford et al. "Cloning of the Human Thyrotropin β-Subunit Gene and Transient Expression of Biologically Active Human Thyrotropin After Gene Transfection", Molecular Endocrinology, 2: 32-39, 1988.
Wu et al. "Receptor-Mediated Gene Delivery and Expression In Vivo", The Journal of Biological Chemistry, 263(29): 14621-14624, 1988.
Wulf et al. "Somatic Stem Cell Plasticity: Current Evidence and Emerging Concepts", Experimental Hematology, 29: 1361-1370, 2001.
Yang et al. "In Vitro Trans-Differentiation of Adult Hepatic Stem Cells Into Pancreatic Endocrine Hormone-Producing Cells", Proc. Natl. Acad. Sci. USA, 99(12): 8078-8083, 2002.
Yin et al. "AC133, A Novel Marker for Human Hematopoietic Stem and Progenitor Cells", Blood, 90(12): 5002-5012, 1997.
Ylä-Herttuala et al., "Gene transfer as a tool to induce therapeutic vascular growth", Nature Medicine, 9(6): 694-701 (2003).
Yoon et al., "Clonally Expanded Novel Multipotent Stem Cells From Human Bone Marrow Regenerate Myocardium After Myocardial Infarction", J. Clin. Invest., 115(2):326-338 (2005).
Zidar et al. "Observations on the Anemia and Neutropenia of Human Copper Deficiency", American Journal of Hematology, 3: 177-185, 1977.
Zocchi et al. "Ligand-Induced Internalization of CD38 Results in Intracellular Ca2+ Moblization: Role of NAD+ Transport Across Cell Membranes", The FASEB Journal, 13(2): 273-283, 1999. Abstract.
Zon et al. "Developmental Biology of Hematopoiesis", Blood, 86(8): 2876-2891, 1995.
Examination Report Dated Jun. 10, 2010 From the Intellectual Property Office of Singapore Issued by the Australian Patent Office Re.: Application No. SG 200804154-3.
From the Israel Patent Office Re. Application No. 191669 Office Action Dated Jul. 12, 2010 and its Translation Into English.
Communication Pursuant to Article 94(3) EPC Dated Aug. 5, 2010 From the European Patent Office Re. Application No. 05784625.5.
Bae et al. "Retinoic Acid-Induced HL-60 Cell Differentiation is Augmented by Copper Supplementation", J. of Nutrition 123(6): 997-1002, (1993).
European Patent Office Re.: Application No. 05784625.5, "Supplementary Partial European Search Report and the European Search Opinion" Dated Aug. 11, 2009.
International Bureau of WIPO Re.: Application No. PCT/IL2006/001381, "International Preliminary Report on Patentability" Dated Jun. 12, 2008.
International Bureau of WIPO Re.: Application No. PCT/IL2005/000994, "International Preliminary Report on Patentability" Dated Jan. 22, 2009.
Lee et al. "Clonal Expansion of Adult Rat Hepatic Stem Cell Lines by Suppression of Asymmetric Cell Kinetics (SACK)", Biotechnology and Bioengineering, 83(7): 760-771, Sep. 30, 2003.
Li et al. "Cell Life Versus Cell Longevity: Ther Mysteries Surrounding the NAD+ Precursor Nicotinamide", Current Medicinal Chemistry, XP002539111, 13(8): 883-895, Apr. 2006.
Robinson et al. "Ex Vivo Expansion of Umbilical Cord Blood", Cytotherapy, XP009120788, 7(3): 243-250, (2005).
Segev et al. "Differentiation of Human Embryonic Stem Cells Into Insulin-Producing Clusters", Stem Cells, XP009038283, 22(3): 265-274, Jan. 1, 2004. Abstract.
U.S. Patent and Trademark Office Re.: U.S. Appl. No. 11/289,004, "Official Action" Dated Jun. 28, 2006.
U.S. Patent and Trademark Office Re.: U.S. Appl. No. 11/289,004, "Official Action" Dated Sep. 20, 2006.
U.S. Patent and Trademark Office Re.: U.S. Appl. No. 11/606,525, "Official Action" Dated Nov. 25, 2008.
U.S. Patent and Trademark Office Re.: U.S. Appl. No. 11/606,525, "Official Action" Dated Mar. 20, 2009.
Vaca et al. "Nicotinamide Induces Both Proliferation and Differentiation of Embryonic Stem Cell Into Insulin-Producing Cells", Transplantion Proceedings, XP002539110, 35(5): 2021-2023, Aug. 2003, Abstract.
Verhoeyen et al. "Reshaping Human Antiodies: Grafting An Antilysozyme Activity", Science, 239: 1534-1536, 1988.
ACS, "Chelation Therapy", American Cancer Society, pp. 1-5 (2006).
Acsadi et al., "Human Dystrophin Expression in Mdx Mice After Intramuscular Injection of DNA Constructs", Nature, 352:815-818 (1991).
Alter, "Fetal Erythropoiesis in Stress Hemopoiesis", Experimental Hematology, 7(5):200-209 (1979).
Aoki et al., "In Vivo Transfer Efficiency of Antisense Oligonucleotides Into the Myocardium Using HVS Liposome Method", Biochemical and Biophysical Research Communications, 231:540-545 (1997).
Armentano et al., "Expression of Human Factor IX in Rabbit Hepatocytes by Retrovirus-Mediated Gene Transfer: Potential for Gene Therapy of Hemophilia B", Proc. Natl. Acad. Sci. USA, 87: 6141-6145 (1990).
Arriero et al., "Adult Skeletal Muscle Stem Cells Differentiate Into Endothelial Lineage and Ameliorate Renal Dysfunction After Acute Ischemia", American Journal. of Physiology—Renal Physiology, 287:F621-F627 (2004).
Auger et al., "PDGF-Dependent Tyrosine Phosphorylation Stimulates Production of Novel Polyphosphoinositides in Intact Cells", Cell, 57:167-175 (1989).
Avital et al., "Isolation, Characterization, and Transplantation of Bone Marrow-Derived Hepatocyte Stem Cells", Biochem. Biophy. Res. Comm., 288(1):156-164 (2001).
Bae et al., "Copper Uptake and Intracellular Distribution During Retonoic Acid-Induced Differentiation of HL-60 Cells", J. Nutr. Biochem., 5:457-461 (1994).
Bae et al., "Retonic Acid-Induced HL-60 Cell Differentiation is Augmented by Copper Supplementation 1-4", J Nutr., 123(6):997-1002 (1993).
Banno et al., "Anemia and Neutropenia in Eldery Patients Caused by Copper Deficiency for Long-Term Eternal Nutrition", Rinsho-Ketsueki, 35:1276-1280 (1994).
Baum et al., "Isolation of a Candidate Human Hematopoietic Stem-Cell Population", Proc. Natl. Acad. Sci. USA, 89:2804-2808 (1992).

(56) References Cited

OTHER PUBLICATIONS

Belovari et al., "Differentiation of Rat Neural Tissue in a Serum-Free Embryo Culture Model Followed by In Vivo Transplantation", *Croatian Medical Journal*, 42(6): 611-617 (2001) (Abstract).
Berardi et al., "Individual CD34+CD38lowCD19-CD10-Progenitor Cells From Human Cord Blood Generate B Lymphocytes and Granulocytes", *Blood*, 89(10):3554-3564 (1997).
Berkner, "Development of Adenovirus Vectors for the Expression of Heterologous Genes", *BioTechniques*, 6(7):616-629 (1988).
Bertagnolo et al., "Phosphoinositide 3-Kinase Activity Is Essential for all-trans-Retinoic Acid-induced Granulocytic Differentiation of HL-60 Cells", *Cancer Res.*, 59:542-546 (1999).
Bhat-Nakshatri, et al., "Tumour necrosis factor and PI3-kinase control oestrogen receptor alpha protein level and its transrepression function", *Br. I Cancer*, 90:853-859 (2004).
Bhatia et al., "Purification of Primitive Human Hematopoietic Cells Capable of Repopulating Immune-Deficient Mice", *Proc. Natl. Acad. Sci. USA*, 94:5320-5325 (1997).
Bi et al., "Effect of Lactoferrin on Proliferation and Differentiation of the Jurkat Human Lymphoblastic T Cell Line", *Arch. Immunol. Ther. Exp.*, 45(4):315-320 (1997) (Abstract).
Bird et al., "Single-Chain Antigen-Binding Proteins", *Science*, 242: 423-426 (1988).
Blau et al., "Fetal Hemoglobin in Acute and Chronic Stage of Erythroid Expansion", *Blood*, 81(1):227-233 (1993).
Boerner et al., "Production of Antigen-Specific Human Monoclonal Antibodies From In Vitro-Primed Human Splenocytes", *The Journal of Immunology*, 147(1):86-95 (1991).
Bohmer et al., "Fetal Cell Isolation From Maternal Blood Cultures by Flow Cytometric Hemoglobin Profiles", *Fetal Diagnosis and Therapy*, 17(2):83-89 (2002).
Bongers et al., "Kinetics of Dipeptyl Peptidase IV Proteolysis of Growth Hormone-Releasing Factor and Analogs", *Biochimica et Biophysica Acta*, 1122:147-153 (1992).
Borthwick et al., "A Comparison of Cupruretic Responses to Various Tetramines and D-Penicillamine", *Journal of Laboratory and Clinical Medicine*, 95(4):575-580 (1980) (Discussion, Table 1).
Brandt et al., "Ex Vivo Expansion of Autologous Bone Marrow CD34+ Cells With Porcine Microvascular Endothelial Cells Results in a Graft Capable of Rescuing Lethally Irradiated Baboons", *Blood*, 94(1):106113 (1999).
Brazelton et al., "From Marrow to Brain: Expression of Neuronal Phenotypes in Adult Mice", *Science*, 290(5497):1775-1779 (2000) (Abstract).
Breitman et al., "Induction of differentiation of the human promyelocytic leukemia cell line (HL-60) by retinoic acid", *Proc. Natl. Acad. Sci. U.S.A.*, 77(5):2936-2940 (1980).
Briddell et al., "Purification of CD34+ Cells Is Essential for Optimal Ex Vivo Expansion of Umbilical Cord Blood Cells", *Journal of Hematotherapy*, 6:145-150 (1997).
Brigham et al., "Rapid Communication: In Vivo Transfection of Murine Lungs With a Functioning Prokaryotic Gene Using a Liposome Vehicle", *The American Journal of the Medical Sciences*, 298(4):278-281 (1989).
Brott et al., "Flow Cytometric Characterization of Perfused Human Bone Marrow Cultures: Identification of the Major Cell Lineages and Correlation With the CFU-GM Assay", *Cytometry*, Part A, 53A:22-27 (2003).
Brugger et al., "Ex Vivo Expansion of Enriched Peripheral Blood CD34+ Progenitor Cells by Stem Cell Factor, Interleukin-1 p (IL-10), IL-6, IL-3, Interferon-y, and Erythropoietin", *Blood*, 81(10):2579-2584 (1993).
Brugnera et al., "Cloning, Chromosomal Mapping and Characterization of the Human Metal-Regulatory Transcription Factor MTF-1", *Nucleic Acids Research*, 22(15):3167-3173 (1994).
Bryder et al., "Hematopoietic Stem Cells: the paradigmatic tissue-specific stem cell." *Am 7 Pathol.*, 169(2):338-46 (2006).
Burgada et al., "Synthesis of New Phosphonated Tripod Ligands as Putative New Therapeutic Agents in the Chelation Treatment of Metal Intoxications", *Euro. J. Org. Chem.*, pp. 349-352 (2001).

Buskin et al., "Identification of a Myocyte Nuclear Factor That Binds to the Muscle-Specific Enhancer of the Mouse Muscle Creatine Kinase Gene", *Molecular and Cellular Biology*, 9(6):2627-2640 (1989).
Butt, "Introduction to Chemical Reactor Theory", *Reaction Kinetics and Reactor Design*, Chap.4:184-241 (1980).
Cable et al., "Exposure of Primary Rat Hepatocytes in Long-Term DMSO Culture to Selected Transition Metals Induces Hepatocyte Proliferation and Formation of Duct-Like Structure", *Hepatology*, 26(6):1444-1457 (1997).
Cakir-Kiefer et al., "Kinetic Competence of the cADP-Ribose-CD38 Complex as an Intermediate in the CD38/NAD+ Glycohydrolase-Catalysed Reactions: Implication for CD38 Signalling", *Biochemical Journal*, 358:399-405 (2001).
Caliaro et al., "Response of four human ovarian carcinoma cell lines to all-trans retinoic acid: relationship with induction of differentiation and retinoic acid receptor expression", *Int. J. Cancer*, 56(5):743-748, (1994) (Abstract Only).
Casal et al., "In Utero Transplantation of Fetal Liver Cells in the Mucopolysaccharidosis Type VII Mouse Results in Low-Level Chimerism, But Overexpression of Beta-Glucuronidase Can Delay Onset of Clinical Signs", *Blood*, 97(6): 1625-1634 (2001).
Cepko, "Overview of the Retrovirus Transduction System", *Short Protocols in Molecular Biology*, Unit 9.109.14: 9-41-9-57 (1984).
Charrier et al., "Normal Human Bone Marrow CD34+30 CD133+ Cells Contain Primitive Cells Able to Produce Different Categories of Colony-Forming Unit Megacaryocytes in Vitro", *Exper. Hema.*, 30:1051-1060 (2002).
ChemMasters, "Duraguard 100", Safety Data Sheet, pp. 1-4 (1999).
Chen et al., "Differentiation of Rat Marrow Mesenchymal Stem Cells into Pancreatic Islet BetaCells", *World Journal of Gastroenterology*, 10(20):3016-3020 (2004).
Chen et al., "Fibroblast Growth Factor (FGF) Signaling Through PI 3-Kinase and Akt/PKB Is Required for Embryoid Body Differentiation", *Oncogene*, 19:3750-3756 (2000).
Chen et al., "Therapeutic Benefit of Intravenous Administration of Bone Marrow Stromal Cells After Cerebral Ischemia in Rats", *Stroke*, 32(4)1005-1011 (2001).
Chisi et al., "Inhibitory Action of the Peptide AcSDKP on the Proliferative State of Hematopoietic Stem Cells in the Presence of Captopril But Not Lisinopril", *Stem Cells*, 15(6):455-460 (1997).
Chowdhury et al., "Long-Term Improvement of Hypercholesterolemia After Ex Vivo Gene Therapy in LDLRDeficient Rabbits", *Science*, 254:1802-1805 (1991).
Christopherson II et al., "Cell Surface Peptidase CD26/Dipeptidylpeptidase IV Regulates CXCL12/Stromal Cell-Derived Factor-la-Mediated Chemotaxis of Human Cord Blood CD34+ Progenitor Cells", *The Journal of Immunology*, 169:7000-7008 (2002).
Christopherson II et al., "Modulation of Hematopoietic Stem Cell Homing and Engraftment by CD26", *Science*, 305:1000-1003 (2004).
Cicuttini et al., "Support of Human Cord Blood Progenitor Cells on Human Stromal Cell Lines Transformed by SV40 Large T Antigen Under the Influence of an Inducible (Metallothionein) Promoter", *Blood*, 80(1): 102-112, 1992. p. 104, col.2, "Coculture of CD34 + Cells", Abstract, p. 104, 1-h col., last §, r-h col., § 2, p. 107, 1-h col., § 2, p. 110,1-h col., last §, r-h col., §1. // EP/OA of 25.4.03 in 20816.
Cole et al., "The EBV-Hybridoma Technique and-Its Application to Hum4 Lung Cancer", *Monoclonal Antibodies and Cancer Therapy*, pp. 77-96 (1985).
Colter et al., "CD34+ Progenitor Cell Selection: Clinical Transplantation, Tumor Cell Purging, Gene Therapy, Ex Vivo Expansion, and Cord Blood Processing", *Journal of Hematology*, 5:179-184 (1996).
Coutinho et al., "Effects of Recombinant Human Granulocyte Colony-Stimulating Factor (CSF), Human Granulocyte Macrophage-CSF, and Gibbon Interleukin-3 on Hematopoiesis Human Long-Term Bone Marrow Culture", *Blood*, 75(11):2118-2129 (1990).
Cristiano et al., "Hepatic Gene Therapy: Adenovirus Enhancement of Receptor-Mediated Gene Delivery and Expression in Primary Hepatocytes", *Proc. Natl. Acad. Sci. USA*, 90:2122-2126 (1993).
Curiel et al., "Adenovirus Enhancement of Transferrin-Polylysine-Mediated Gene Delivery", *Proc. Natl. Acad. Sci. USA*, 88:8850-8854 (1991).

(56) References Cited

OTHER PUBLICATIONS

Czauderna et al., "Functional studies of the Pl(3)-kinase signalling pathway employing synthetic aid expressed siRNA.", *Nuc. Acid'Res.*, 31(2):670-682 (2003).
Côté et al., "Response to Histone Deacetylase Inhibition of Novel PMURARa Mutants Detected in Retinoic Acid-Resistant APL Cells", *Blood*, 100(7):2586-2596 (2002).
Dabeva et al., "Transcription Factor and Liver-Specific mRNA Expression in Facultative Epithelial Progenitor Cells of Liver and Pancreas", *American Journal of Pathology*, 147:1633-1648 (1995) (Abstract).
Dahl et al., "Tranformation of Hematopoietic Cells by the Ski Oncoprotein Involves Repression of Retinoic Acid Receptor Signaling", *Proc. Natl. Acad. Sci. USA*, 95(19):11187-11192 (1998).
Dai et al., "Gene Therapy Via Primary Myoblasts: Long-Term Expression of Factor IX Protein Following Transplantation In Vivo", *Proc. Natl. Acad. Sci. USA*, 89:10892-10895 (1992).
Dalyot et al., "Adult and Neonatal Patterns of Human Globin Gene Expressioon Are Recapitulated in Liquid Cultures", *Experimental Hematology*, 20:1141-1145 (1992) (Abstract).
Danos et al., "Safe and Efficient Generation of Recombinant Retroviruses With Amphotropic and Ecotropic Host Ranges", *Proc. Natl. Acad. Sci. USA*, 85:6460-6464 (1988).
Datta et al., "Ionizing Radiation Activates Transcription of the EGR1 Gene Via CArG Elements", *Proc. Natl. Acad. Sci. USA*, 89:10149-10153 (1992).
De Bruyn et al., "Comparison of the Coexpressioin of CD33 and HLA-DR Antigens on CD34+ Purified Cells From Human Cord Blood and Bone Narrow", *Stem Cells*, 13:281-288 (1995).
De Luca et al., "Retinoic Acid Is a Potent Regulator of Growth Plate Chondrogenesis", *Endocrinology*, 141(1):346-353 (2000) (Abstract).
De Wynter et al., "CD34+AC133+ Cells Isolated From Cord Blood Are Highly Enriched in Long-Term Culture-Initiating Cells, NOD/SCID-Repopulating Cells and Dendritic Cell Progenitors", *Stem Cells*, 16:387396 (1998).
Defacque et al., "Expression of Retinoid X Receptor Alpha Is Increased Upon Monocytic Cell Differentiation", *Biochemical and Biophysical Research Communications*, 220:315-322 (1996).
Dexter et al., "Conditions Controlling the Proliferation of Haemopoietic Stem Cells In Vitro", *Journal of Cell Physiology*, 91:335-344 (1976).
DOD, Tetraethylene Pentamine DOD Hazardous Material Information; 6810-00F017710 (1991).
Donovan et al., "The End-of the Beginning for Pluripotent Stem Cells", *Nature*, 414(6859):92-97 (2001).
Dosil et al., "Mitogenic Signalling and Substrate Specificity of the Flk2/Flt3 Receptor Tyrosine Kinase in Fibroblasts and Interleukin in 3-Dependent Hematopoietic Cells", *Mol. Biol.*, 13(10):6572-6585 (1993) (Abstract Only).
Douer et al., "All-trans-retinoic acid effects the growth, differentiation and apoptosis of normal human myeloid progenitors derived from purified CD34+ bone marrow cells", *Leukemia*, 14(5):874-881 (2000).
Drayson et al., "Cell Proliferation and CD11b Expression Are Controlled Independently during HL60 Cell Differentiation Initiated by 1,25a-Dihydroxyvitamin D3 or All-trans-Retinoic Acid", *Exp. Cell Res.*, 266(1):126-134 (2001) (Abstract Only).
Dubois et al., "Treatment of Wilson's Disease With Trietylene Tetramine Hydrochloride (Trientine)", *J. Pediatr. Gastroenterol. Nutr.*, 10(1):77-81 (1990) (Abstract).
Duncan et al., "Repair of Myelin Disease: Strategies and Progress in Animal Models", *Molecular Medicine Today*, 3(12):554-561 (1997) (Abstract).
Ebner et al., "Distinct Roles for Pl3K in Proliferation and Survival of Oligodendrocyte Progenitor Cells", *Journal of Neuroscience Research*, 62:336-345 (2000). p. 338-344.
Eglitis et al., "Gene Expression in Mice After High Efficiency Retroviral-Mediated Gene Transfer", *Science*, 230: 1395-1398 (1985).
Ehring et al., "Expansion of HPCs From Cord Blood in a Novel 3D Matrix", *Cytotherapy*, 5(6):490-499 (2003).
Eipers et al., "Retroviral-Mediated Gene Transfer in Human Bone Marrow Cells Grown in Continuous Perfusion Culture Vessels", *Blood*, 86(10):3754-3762 (1996).
EM Science, Thiotepa Product Identification Sheet; THIOTEPA; 6505-01-047-3872 (1990).
Emerson, "Ex Vivo Expansion of Hematopoietic Precursors, Progenitors, and Stem Cells: The Next Generation of Cellular Therapeutics", *Blood*, 87(8): 3082-3088 (1996).
Englisch et al., "Chemically Modified Oligonucleotides as Probes and Inhibitors", *Angewandte Chemie (International Edition in English*, 30(6):613-629 (1991).
Fasouliotis et al., "Human Umbilical Cord Blood Banking and Transplantation: A State of Art", *Euro. I Obstet. Gynec. Reprod. Bio.*, 90(1):13-25 (2000).
Feldman, "Israeli Start-Up Gamida-Cell to Receive Prize", GLOBES—Online (2004).
Ferbeyre, "PML a Target of Translocations in APL Is a Regulator of Cellular Senescence", *Leukemia*, 16:1918-1926 (2002) (Abstract).
Ferrari et al., "Muscle Regeneration by Bone Marrow-Derived Myogenic Progenitors", *Science*, 279(5356):1528-1530 (1998). Erratum in: *Science*, 281(5379):923 (1998).
Ferrero et al., "The Metamorphosis of a Molecule: From Soluble Enzyme to the Leukocyte Receptor CD38", *J. Leuk. Bio.*, 65(2):151-161 (1999).
Ferry et al., "Retroviral-Mediated Gene Transfer Into Hepatocytes In Vivo", *Proc. Natl. Acad. Sci. USA*, 88:8377-8381 (1991).
Fibach et al., "Growth of Human Normal Erythroid Progenitors in Liquid Culture: A Comparison With Colony Growth in Semisolid Culture", *International Journal of Cell Cloning*, 9:57-64 (1991).
Fibach et al., "Normal Differentiation of Myeloid Leukemic Cells Induced by Differentiation-Indicing Protein", *Nature*, 237:276-278 (1972).
Fibach et al., "Proliferation and Maturation of Human Erythroid Progenitors in Liquid Culture", *Blood*, 73(1):100-103 (1989) (Abstract).
Fibach et al., "Retinoic Acid Antagonist Inhibits CD38 antigen Expression on Human Hematopoietic Cells", *Blood*, 100(11):172A & 44th Annual Meeting of the American Society of Hematology (2002) (Abstract).
Fibach et al., "The Two-Step Liquid Culture: A Novel Procedure for Studying Maturation of Human Normal and Pathological Erythroid Precursors", *Stem Cells*, 11(Supp1.1):36-41 (1993) (Abstract).
Fietz et al., "Culturing Human Umbilical Cord Blood: A Comparison of Mononuclear Vs CD34+ Selected Cells", *Bone Marrow Transplantation*, 39:11-23 (2007).
Filvaroff et al., "Functional Evidence for an Extracellular Calcium Receptor Mechanism Triggering Tyrosine Kinase Activation Associated With Mouse Keratinocyte Differentiation", *The Journal of Biological Chemistry*, 269(34):21735-21740 (1994).
Fishwild et al., "High-Avidity Human IgGx Monoclonal Antibodies From a Novel Strain of Minilocus Transgenic Mice", *Nature Biotechnology*, 14:845-851 (1996).
Fibres et al., "Akt-Mediated Survival of Oligodendrocytes Induced by Neuregulins", *The Journal of Neuroscience*, 20(20): 7622-7630 (2000) pp. 7624-7629.
Flotte et al., "Expression of the Cystic Fibrosis Transmemebrane Conductance Regulators From a Novel Adeno-Associated Virus Promoter", *The Journal of Biological Chemistry*, 268(5):3781-3790 (1993).
Flotte et al., "Gene Expression From Adeno-Associated Virus Vectors in Airways Epithelial Cells", *Amercan Journal of Respiratory Cell and Molecular Biology*, 7:349-356 (1992).
Fosmire, "Zinc Toxicity", *American Journal of Clinical Nutrition*, 51(2):225-227 (1990) (Abstract).
Freedman et al., "Generation of Human T Lymphocytes From Bone Marrow CD34+ Cells In Vitro", *Nature Medicine*, 2(2):46-51 (1996).
Fry, "Phosphoinositide 3-kinase signalling in breast cancer: how big a role might it play?", *Breast Cancer Res.*, 3(5):304-312 (2001).
Gagnon et al., "Activation of Protein Kinase B and Induction of Adipogenesis by Insulin in 3T3-L1 Preadipocytes", *Diabetes*, 48:691-698 (1999) pp. 693-697.

(56) References Cited

OTHER PUBLICATIONS

Gallacher et al., "Isolation and characterization of human CD34⁻Lin⁻ and CD34⁺Lin⁻ hematopoietic stem cells using cell surface markers AC133 and CD7", *Blood*, 95(9):2813-2820 (2000).
Gloeckner et al., "New Miniaturized Hollow-Fiber Bioreactor for In Vivo Like Cell Culture, Cell Expansion, and Production of Cell-Derived Products", *Biotechnology Progresses*, 17:828-831 (2001).
Gossler et al., "Transgenesis by Means of Blasocyst-Derived Embroyonic Stem Cell Lines", *PNAS*, 83:9065-9069 (1986).
Gould-Fogerite et al., "Chimerasome-Mediated Gene Transfer in Vitro and in Vivo", *Gene*, 84:429-438 (1989).
Grande et al., "Physiological Levels of 1Alpha, 25 Dihydroxyvitamin D3 Induce the Monocytic Commitment of CD34+ Hematopoietic Progenitors", *J. Leukoc. Biol.*, 71(4):641-651 (2002).
Grenda et al., "Mice Expressing a neutrophil Elastase Mutation Derived From Patients With Severe Congenital Neutropenia Have Normal Granulopoiesis", *Blood*, 100(9):3221-3228 (2002).
Gur et al., "Toelrance Induction by Megadose Hematopoietic Progenitor Cells: Expansion of Veto Cells by Short-Term Culture of Purified Human CD34+ Cells", *Blood*, 99:4174-4181 (2002).
Haj-Ahmad et al., "Development of a Helper-Independent Human Adenovirus Vector and Its Use in the Transfer of the Herpes Simplex Virus Thymidine Kinase Gene", *Journal of Virology*, 57(1):267-274 (1986).
Hamilton, "Stem Cell Technology to Treat Leukemia Patients Show Promise", The Wall Street Journal, Online (2003).
Hammond et al., "Suppression of In Vitro Granulocytopoiesis by Captopril and Penicillamine", *Experimental Hematology*, 16(8):674-680 (1988).
Hatayama et al., "Regulation of HSP70 Synthesis Induced by Cupric Sulfate and Zinc Sulfate in Thermotolerant HeLa Cells", *Journal of Biochemistry*, Tokyo, 114(4):592-597 (1993) (Abstract).
Haviemik et al., "Tissue Inhibitor of Matrix Metalloproteinase-1 Overexpression in M1 Myeloblasts Impairs IL-6-Induced Differentiation", *Oncogene*, 23(57): 9212-9219 (2004) (Abstract Only).
Hayashi et al., "Changes in the Balance of Phosphoinositide 3-Kinase/Protein Kinase B (Akt) and the Mitogenactivated Protein Kinases (Erk/p38MAPK) Determine a Phenotype of Visceral and Vascular Smooth Muscle Cells", *J. Cell Biol.*, 145(4):727-740 (1999).
Haylock et al., "Ex-Vivo Expansion and Maturation of Peripheral Blood CD34+ Cells Into the Myeloid Lineage", *Blood*, 80(6):1405-1412 (1992).
Hermonat et al., "Use of Adeno-Associated Virus as a Mammalian DNA Cloning Vector: Transduction of Neomycin Resistance Into Mammalian Tissue Culture Cells", *Proc. Natl. Acad. Sci. USA*, 81:6466-6470 (1984).
Herz et al., "Adenovirus-Mediated Transfer of Low Density Lipoprotein Receptor Gene Acutely Accelerates Cholesterol Clearence in Normal Mice", *Proc. Natl. Acad. Sci. USA*, 90:2812-2816 (1993).
Heuchel et al., "The Transcription Factor MTF-1 Is Essential for Basal and Heavy Metal-Induced Metallothionein Gene Expression", *The EMBO Journal*, 13(12):2870-2875 (1994).
Hida et al., "Existence of Retinoic Acid-Receptor-Independent Retinoid X-Receptor-Dependent Pathway in Myeloid Cell Function", *Jpn. J. Phamacol.*, 85(1):60-69 (2001).
Hino et al., "A Long-Term Culture of Human Hepatocytes Which Show a High Growth Potential and Express Their Differentiated Phenotypes", *Biochem. Biophy. Res. Comm.*, 256(1):184-191 (1999) (Abstract Only).
Hirase et al., "Anemia and Neutropenia in a Case of Copper Deficiency: Role of Copper in Normal Hematopoiesis", *Acta Haematol.*, 87(4):195-197 (1992).
Hirose et al., "Identification of a Transposon-Related RNA Down-Regulated by Retinoic Acid in Embryonal Carcinoma and Embryonic Stem Cells", *Exp. Cell Res.*, 221(2):294-300 (1995) (Abstract).
Hmama et al., "1-Alpha, 25-Dihydroxyvitamin D3-Induced Myeloid Cell Differentiation Is Regulated by a Vitamin D Receptor-Phospatidylinositol 3-Kinase Signaling Complex", *Journal of Experimental Medicine*, 190(11):1583-1594 (1999).
Hoffman et al., "Zinc-Induced Copper Deficiency", *Gastroenterology*, 94(2):508-512 (1988).
Hofmeister et al., "Ex Vivo Expansion of Umbilical Cord Blood Stem Cells for Transplantation: Growing Knowledge From the Hematopoietic Niche", *Bone Marrow Transplantation*, 39:11-23 (2007).
Holleman, "Triethylene Tetramine, CAS No. 112-24-3", Chemical Hazard Information Profile Draft Report, (1982) (Abstract).
Hoogenboom et al., "By-Passing Immunisation Human Antibodies From Synthetic Repertoires of Germline $V_H$ Gene Segments Rearranged In Vitro", *Journal of Molecular Biology*, 227:381-388 (1992).
Hori et al., "Growth Inhibitors Promote Differentiation of Insulin-Producing Tissue From Embryonic Stem Cells", *Proc. Natl. Acad. Sci. USA*, 99(25):16105-16110 (2002).
Hottinger et al., "The Copper Chelator D-Penicillamine Delays Onset of Disease A Extends Survival in a Transgenic Mouse Model of Familial Amyotrophic Lateral Sclerosis", *European Journal of Neuroscience*, 9(7):1548-1551 (1997) (Abstract).
Howard et al., "Formation and hydrolysis of cyclic ADP-ribose catalyzed by lymphocyte antigen CD38", *Science*, 262(5136):1056-1059 (1993) (Abstract Only).
Huang et al., "Differentiation of Human U937 Promonocytic Cells Is Impaired by Moderate Copper Deficiency", *Experimental Biology and Medicine*, 226(3):222-228 (2001).
Huber et al., "Retroviral-Mediated Gene Therapy for the Treatment of Hepatocellular Carcinoma: An Innovative Approach for Cancer Therapy", *Proc. Natl. Acad. Sci. USA*, 88:8039-8043 (1991).
Hutvágner et al., "RNAi: Nature Abhors a Double-Strand", *Current Opinion in Genetics & Development*, 12:225-232 (2002).
Hwu et al., "Functional and Molecular Characterization of Tumor-Infiltrating Lymphocytes Transduced With Tumor Necrosis Factor-a cDNA for the Gene Therapy of Cancer in Humans", *The Journal of Immunology*, 150(9): 4104-4115 (1993).
Hühn et al., "Molecular Analysis of CD26-Mediated Signal Transduction in T Cells", Immunology Letters, 72:127-132 (2000).
Imai et al., "Selective Secretion of Chemoattractants for Haemapoietic Progenitor Cells by Bone Marrow 25Endothelial Cells: A Possible Role in Homing of Haemopoietic Progenitor Cells to Bone Marrow", *British Journal of Haematology*, 106:905-911 (1999).
Imitola et al., "Directed Migration of Neural Stem Cells to Sites of CNS Injury by the Stroman Cello Derived Factor Ia/CXC Chemokine Receptor 4 Pathway", *Proc. Natl. Acad. Sci. USA*, 101(52):18117-18122 (2004).
Inbar et al., "Localization of Antibody-Combining Sites Within the Variable Portions of Heavy and Light Chains", *Proc. Natl. Acad. Sci. USA*, 69(9):2659-2662 (1972).
Itoh et al., "Inhibition of Urokinase Receptor (uPAR) Expression by RNA-Cleaving Catalytic DNA (DNAzyme) Containing Antisense uPAR", *Molecular Therapy*, 5(5/Part 2):S134 (2002).
Jelinek et al., "Novel Bioreactors for the Ex Vivo Cultivation of Hematopoietic Cells", *English Life Science*, 2(1):15-18 (2002).
Jiang et al., "Phosphatidylinositol 3-Kinase Signaling Mediates Angiogenesis and Expression of Vascular Endothelial Growth Factor in Endothelial Cells", *PNAS*, 97(4):1749-1752 (2000).
Johnson et al., "Synthesis and Biological Activity of High-Affinity Retinoic Acid Receptor Antagonists", *Bioorganic & Medicinal Chemistry*, 7(7):1321-1338 (1999).
Johnson et al., "The Cytokines IL-3 and GM-CSF Regulate the Transcriptional Activity of Retinoic Acid Receptors in Different In Vitro Models of Myeloid Differentiation", *Blood*, 99(3):746-753 (2002).
Jones et al., "Replacing the Complementarity-Determining Regions in a Human Antibody With Those From a Mouse", *Nature*, 321:522-525 (1986).
Kang et al., "Retinoic Acid and Its Receptors Repress the Expression and Transactivation Functions of Nur77: A Possible Mechanism for the Inhibition of Apoptosis by Retinoic Acid", *Experimental Cell Research*, 256: 545-553 (2000).

(56) References Cited

OTHER PUBLICATIONS

Kastner et al., "Positive and Negative Regulation of Granulopoiesis by Endogenous RARalpha", *Blood*, 97(5):1314-1320 (2001) (Abstract).
Kaufman et al., "Translational Efficency of Polycistronic mRNAs and Their Utilization to Express Heterologous Genes in Mammalian Cells", *The EMBO Journal*, 6(1):187-193 (1987).
Kawa et al., "Stem Cell Factor and/or Endothelin-3 Dependent Immortal Melanoblast and Melanocyte Populations Derived From Mouse Neural Crest Cells", *Pigment Cell Research*, 13(Suppl.8):73-80 (2000).
Kay et al.., "Hepatic Gene Therapy: Persistent Expression of Human al-Antitxypsin in Mice After Direct Gene Delivery In Vivo", *Human Gene Therapy*, 3:641-647 (1992).
Keith et al., "Multicomponent Therapeutics for Networked Systems", *Nat. Rev.: Drug Disc.*, 4:1-8 (2005).
Khachigian, "DNAzymes: Cutting a Path to a New Class of Therapeutics", *Current Opinion in Molecular Therapeutics*, 4(2):119-121 (2002).
Kim, "Differentiation and Identification of the Two Cntnlytic Metal Binding Sites in Bovine Lens Leucine Aminopeptidase by X-Ray Crystallography", *Proc. Natl. Acad. Sci. USA*, 90(11):5006-5010 (1993).
Kishimoto et al., "Molecular Mechanism of Human CD38 Gene Expression by Retinoic acid. Identification of Retinoic Acid Response Elemen in the First Intron", *J. Biol. Chem.*, 273(25):15429-15434 (1998) (Abstract).
Kitanaka et al., "CD38 ligation in human B cell progenitors triggers tyrosine phosphorylation of CD19 and association of CD19 with lyn and phosphatidylinositol 3-kinase.", *J Immunol.*, 159(1):184-192 (1997).
Kizaki et al., "Regulation of Manganese Superoxide Dismutase and Other Antioxidant Genes in Normal and Leukemic Hematopoietic Cells and Their Relationship to Cytotoxicity by Tumor Necrosis Factor", *Blood*, 82(4): 1142-1150 (1993).
Kobari et al., "CD133+ cell selection is an alternative to CD34+ cell selection for ex vivo expansion of hematopoietic stem cells.", *J Hematother Stem Cell Res.*, 10(2):273-281 (2001).
Kocher et al., "Neovascularization of Ischemic Myocardium by Human Bone-Marrow-Derived Angioblasts Prevents Cardiomyocyte Apoptosis, Reduces Remodeling and Improves Cardiac Function", *Nat. Med.*, 7(4):430-436 (2001).
Kohroki et al., "Induction of Differentiation and Apoptosis by Dithizone in Human Myeloid Leukemia Cell Lines", *Leukemia Research*, 22(5):405-412 (1998) (Discussion).
Koizumi et al., "Large Scale Purification of Human Blood CD34+ Cells From Cryopreserved Peripheral Blood Stem Cells, Using a Nylon-Fiber Syringe System and Immunomagnetic Microspheres", *Bone Marrow Transplantation*, 26:787-793 (2000).
Krause et al., "Multi-Organ, Multi-Lineage Engraftment by a Single Bone Marrow-Derived Stem Cell", *Cell*, 105(3):369-377 (2001) (Abstract).
Kronenwett et al., "Oligodeoxyribonucleotide Uptake in Primary Human Hematopoietic Cells Is Enhanced by Cationic Lipids and Depends on the Hematopoietic Cell Subset", *Blood*, 91(3):852-862 (1998).
Ku et al., "Committing Embryonic Stem Cells to Early Endocrine Pancreas In Vitro", *Stem Cells*, 22:1205-1217 (2004).
Kumagai et al., "Ligation of CD38 Suppresses Human B Lymphopoiesis", *J. Exp. Med.*, 181(3):1101-1110 (1995).
Kähne et al., "Dipeptidyl Peptidase IV: A Cell Surface Peptidase Involved in Regulating T Cell Growth (Review)", *International Journal of Molecular Medicine*, 4:3-15 (1999).
Köhler et al., "Defining Optimum Conditions for the Ex Vivo Expansion of Human Umbilical Cord Blood Cells. Influences of Progenitor Enrichment, Interference With Feeder Layers, Early-Acting Cytokines and Agitation of Culture Vessels", *Stem Cells*, 17(1):19-24 (1999).
Labrecque et al., "Impaired Granulocytic Differentiation In Vitro in Hematopoietic Cells Lacking Retinoic Acid Receptors al and γ", *Blood*, 92(2):607-615 (1998).
Lagasse et al., "Purified Hematopoietic Stem Cells Can Differentiate Into Hepatocytes In Vivo", *Nature Medicine*, 6(11):1229-1234 (2000).
Lam et al., "Preclinical Ex Vivo Expansion of Cord Blood Hematopoietic Stem and Progenitor Cells: Duration of Culture: the Media, Serum Supplements, and Growth Factors Used; and Engraftment in NOD/SCID Mice", *Transfusion*, 41(12):1567-1576 (2001) (Abstract).
Lange et al., "Biological and Clinical Advances in Stem Cell Expansion", *Leukemia*, 10:943-945 (1996).
Lapidot et al., "Cytokine Stimulation of Multilineage Hematopoiesis From Immature Human Cells Engrafted in SCID Mice", *Science*, 255:1137-1141 (1992).
Larrick et al., "PCR Amplification of Antibody Genes", Methods: *A Companion to Methods in Enzymology*, 2(2):106-110 (1991).
Lassila et al., "Role for Lys-His-Gly-NH2 in Avian and Murin B Cell Development", *Cellular Immunology*, 122(2):319-328 (1989) (Figs).
Lau et al., "A Peptide Molecule Mimicking the Copper (II) Transport Site of Human Serum Albumin", *Journal of Biological Chemistry*, 249(16):5878-5884 (1974) (Discussion).
Lavigne et al., "Enhanced Antisense Inhibition of Human Immunodeficiency Virus Type 1 in Cell Cultures by DLS Delivery System", *Biochemical and Biophysical Research Communications*, 237:566-571 (1997).
Lawlor et al., "Coordinate Control of Muscle Cell Survival by Distinct Insulin-Like Growth Factor Activated Signaling Pathways", *The Journal of Cell Biology*, 151 (6): 1131-1140 (2000) pp. 1133-1139.
Lee et al., "Clonal Expansion of Adult Rat Hepatic Stem Cell Lines by Suppression of Asymmetric Cell Kinetics (SACK)", *Biotechnology and Bioengineering*, 83(7):760-771 (Sep. 30, 2003).
Lee et al., "Effect of a vitamin $D^3$ analog, EB1089, on hematopoietic stem cells from normal and myeloid leukemic blasts", *Leukemia*, 10:1751-1757 (1996).
Lemarchand et al., "Adenovirus-Mediated Transfer of a Recombinant Human al-Antitrypsin cDNA to Human Endothelial Cells", *Proc. Natl. Acad. Sci. USA*, 89:6482-6486 (1992).
Leslie et al., "An Activating Mutation in the Kit Receptor Abolishes the Stroma Requirement for Growth of ELM Erythroleukemia Cells, But Does Not Prevent Their Differentiation in Response to Erythropoietin", *Blood*, 92(12):4798-4807 (1998).
Lewandowski et al., "Phosphatidylinositol 3-Kinases Are Involved in the All-Trans Retinoic Acid-Induced Upregulation of CD38 Antigen on Human Haematopoietic Cells", *British Journal of Hematology*, 118(2):535-544 (2002) (Fig.8).
Li et al., "Activation of Phosphatidylinositol-3 Kinase (Pl-3K) and Extracellular Regulated Kinases (Erk1/2) Is Involved in Muscarinic Receptor-Mediated DNA Synthesis in Neural Progenitor Cells", *The Journal of Neuroscience*, 21(5):1569-1579 (2001) pp. 1572-1578.
Li et al., "Cell Life Versus Cell Longevity: Ther Mysteries Surrounding the NAD+ Precursor Nicotinamide", *Current Medicinal Chemistry*, XP002539111, 13(8):883-895 (2006).
Lianguzova et al., "Pl3-Kinase Inhibitors LY294002 and Wortmannin Have Different Effects on Proliferation of Murine Embryonic Stem Cells", *Tsitologiia*, 48(7):560-568 (2006) (English Abstract Only).
Lonberg et al., "Antigen-Specific Human Antibodies From Mice Comprising Four Distinct Genetic Modifications", *Nature*, 368:856-859 (1994).
Lonberg et al., "Human Antibodies From Transgenic Mice", *International Review in Immunology*, 13:65-93 (1995).
Lovejoy et al., "Novel 'Hybrid' Iron Chelators Derived From Aroylhydrazones and Thiosemicarbazones Demonstrate Delective Antiproliferative Activity Against Tumor Cells", *Blood*, 100(2):666-676 (2002).
Lu et al., "Intravenous Administration of Human Umbilical Cord Blood Reduces Neurological Deficit in the Rat After Traumatic Brain Injury", *Cell Transplant.*, 11(3):275-281 (2002) (Abstract Only).
Luft, "Making Sense Out of Antisense Oligodeoxynucleotide Delivery: Getting There Is Half the Fun". *J. Mel. Med*, pp. 75-76 (1998).

(56) References Cited

OTHER PUBLICATIONS

Lupi et al., "Endogenous ADP-Ribosylation of the G Protein f3 Subunit Prevents the Inhibition of Type 1 Adenlyl Cyclase", *The Journal of Biological Chemistry*, 275(13):9418-9424 (2000).

Lutton et al., "Zinc Porphyrins: Potent Inhibitors of Hematopoieses in Animal and Human Bone Marrow", *Proc. Natl. Acad. Sci. USA*, 94:1432-1436 (1997).

Ma et al., "Inhibition of phosphatidylinositol 3-kinase causes apoptosis in retinoic acid differentiated hl-60 leukemia cells", *Cell Cycle*, 3(1):67-70 (2004).

Mader et al., "A Steroid-Inducible Promoter for the Controlled Overexpression of Cloned Genes in Thilcaryotic Cells", *Proc. Natl. Acad. Sci. USA*, 90:5603-5607 (1993).

Madlambayan et al., "Controlling Culture Dynamics for the Expansion of Hematopoietic Stem Cells", *J. Hematother. Stem Cell Res.*, 10(4):481-492 (2001) (Abstract Only).

Manome et al., "Coinduction of C-Jun Gene Expression and Internucleosomal DNA Fragmentation by Ionizing Radiation", *Biochemistry*, 32:10607-10613 (1993).

Mar et al., "A Conserved CATTCCT Motif Is Required for Skeletal Muscle-Specific Activity of the Cardiac Troponin T Gene Promoter", *Proc. Natl. Acad. Sci. USA*, 85:6404-6408 (1988).

Marcinkowska, E., "Does the universal 'signal transduction pathway of differentiation' exist? Comparison of different cell differentiation experimental models with differentiation of HL-60 cells in response to 1,25- dihydroxyvitamin D3", *Postepy Hig. Med. Dosw.*, 53(2):305-313 (1999) (Abstract Only).

Marks et al., "By-Passing Immunization. Human Antibodies From V-Gene Libraries Displayed on Phage", *Journal of Molecular biology*, 222:581-597 (1991).

Marks et al., "By-Passing Immunization: Building High Affinity Human Antibodies by Chain Shuffling", *Bio/Technology*, 10:779-783 (1992).

Martelli et al., "Transplants Across Human Leukocyte Antigen Barriers", *Seminars in Hematology*, 39(1):48-56 (2002).

Matuoka et al., "A Positive Role of Phosphatidylinositol 3-Kinase in Aging Phenotype Expression in Cultured Human Diploid Fibroblasts", *Arch. Gerontol. Geriatry*, 36:203-219 (2003).

Matzner et al., "Bone Marrow Stem Cell Gene Therapy of Arylsulfatase A-Deficient Mice, Using an Arylsulfatase a Mutant That Is Hypersecreted From Retrovirally Transduced Donor-Type Cells", *Human Gene Therapy*, 12:1021-1033 (2001).

McGrath et al., "Embryonic Expression and Function of the Chemokine SDF.1 and Its Receptor, CXCR4", *Developmental Biology*, 213:442-456 (1999).

McLaughlin et al., "Adeno-Associated Virus General Transduction Vectors: Analysis of Proviral Structures", *Journal of Virology*, 62(6):1963-1973 (1988).

McNiece et al., "Action of Interleukin-3, G-CSF on Highly Enriched Human Hematopoietic Preogenitor Cells: Synergistic Interaction of GM-CSF Plus G-CSF", *Blood*, 74:110-114 (1989).

McNiece et al., "CD34+ Cell Selection From Frozen Cord Blood Products Using the Isolex 300i and CliniMACS CD34 Selection Devices", *Journal of Hematotherapy*, 7:457-461 (1998).

Mehta et al., "Human CD38, a Cell-Surface Protein With Multiple Functions", *J. FASEB*, 10(12):1408-1417 (1996).

Mehta et al., "Involvement of Retinoic Acid Receptor-a-Mediated Signaling Pathway in Induction of CD38 Cell-Surface Antigen", *Blood*, 89(10):3607-3614 (1997) (Abstract).

Mehta et al., "Retinoid-Mediated Signaling Pathways in CD38 Antigen Expression in Myeloid Leukemia Cells", *Leukemia and Lymphoma*, 32(516):441-449 (1999).

Meissner et al., "Development of a Fixed Bed Bioreactor for the Expansion of Human Hematopoietic Progenitor Cells", *Cytotechnology*, 30:227-234 (1999).

Merck & Co., "The Merck Index, An Encyclopedia of Chemicals, Drugs and Biologicals", 10th Ed.(3742):549 (1983).

Mezey et al., "Turning Blood Into Brain: Cells Bearing Neuronal Antigens Generated In Vivo From Bone Marrow", *Science*, 290(5497):1779-1782 (2000).

Migliaccio et al., "Long-Term Generation of Colony-Forming Cells in Liquid Culture of CD34+ Cord Blood Cells in the Presence of Recombinant Human Stem Cell Factor", *Blood*, 79:2620-2627 (1992).

Miller et al., "Expansion In Vitro of Adult Murine Hematopoietic Stem Cells With Transplantable Lympho-Myeloid Reconstituting Ability", *Proc. Natl. Acad. Sci. USA*, 94:13648-13653 (1997).

Miller, "Progress Toward Human Gene Therapy", Blood, *The Journal of the American Society of Hematology*, 76(2): 271-278 (1990).

Mills et al., "Regulation of Retinoid-Induced Differentiation in Embryonal Carcinoma PCC4.Aza 1 R Cells: Effects of Retinoid-Receptor Selective Ligands", *Cell Growth Differ.*, 7(3):327-337 (1996) (Abstract).

Mood, et al., "Contribution of JNK, Mek, Mos and Pl-3K signaling to GVBD in *Xenopus oocytes.*", *Cell. Signalling*, 16:631-642 (2004).

Moore et al., "Ex Vivo Expansion of Cord Blood-Devined Stem Cells and Progenitons", *Blood Cells*, 20:468-481 (1994).

Morier-Teissier et al., "Synthesis and Antitumor Properties of an Anthraquinone Bisubstituted by the Copper Chelating Peptide Gly-Gly-L-His", *Journal of Medical Chemistry*, 36:2084-2090 (1993) (Abstract).

Morimoto et al., *Biochem. Int.*, 28(2):313-321 (1992).

Morosetti et al., "Infrequent Alterations of the RARa Gene in Acute Myelogenous Leukemias, Retinoic Acid-Resistant Acute Promyelocytic Leukemias, Myelodysplastic Syndromes, and Cell Lines", *Blood*, 87(10):4399-4403 (1996).

Morrison et al., "Identification of a Lineage of Multipotent Hematopoietic Progenitors", *Development*, 124:1929-1939 (1997).

Morrison et al., "The Long-Term Repopulating Subset of Hematopoietic Stem Cell Is Deterministic and Isolatable by Phenotype", *Immunity*, 1: 661-673 (1994) (Abstract).

Morrison, "Success in Specification", *Nature*, 368(6474):812-813 (1994).

Mueller et al., "Heterozygous PU.1 Mutations are Associated with Acute Myeloid Leukemia", *Blood*, 100(3):998-1007 (2002).

Muench et al., "Interactions Among Colony-Stimulating Factors, IL-113, IL-6, and Kit-Ligand in the Regulation of Primitive Murine Hematopoietic Cells", *Experimental Hematology*, 20:339-349 (1992).

Mulloy et al., "Maintaining the self-renewal and differentiation potential of human CD34+ hematopoietic cells using a single genetic element", *Blood*, 102(13):4369-4376 (2003).

Munshi et al., "Evidence for a Causal Role of CD38 Expression in Granulocytic Differentiation of Human HL-60 Cells", *The Journal of Biological Chemistry*, 277(51):49453-49458 (2002).

Muramatsu et al., "Reversible Integration of the Dominant Negative Retinoid Receptor Gene for Ex Vivo Expansion of Hematopoietic Stem/Progenitor Cells", *Biochem. Biophys. Res. Commun.*, 285(4):891-896, (2001) (Abstract).

Murray et al., "Modulation of Murine Lymphocyte and Macrophage Proliferation by Parenteral Zinc", *Clinical and Experimental Immunology*, 53(3):744-749 (1983).

Murray et al., Thrombopoietin, Flt3, and Kit Ligands Together Suppress Apoptosis of Human Mobilized CD34+ Cells and Recruit Primitive CD34+Thy-1+ Cells Into Rapid Divions, *Expert. Hemat.*, 27:1019-1028 (1999).

Muzyczka, "Use of Adeno-Associated Virus as a General Transduction Vector for Mammalian Cells", *Current Topics in Microbiology and Immunology*, 158:97-129 (1992).

Narita et al., "Cardiomycyte Differentiation by GATA-4-Deficient Embryonic Stem Cells", *Development*, 122(19):3755-3764 (1996).

Neuberger, "Generating High-Avidity Human Mabs in Mice", *Nature Biotechnology*, 14:826 (1996).

Nicolau et al., "Liposomes as Carriers for In Vivo Gene Transfer and Expression", *Methods in Enzymology*, 149(Chap.16):157-176 (1987).

Ohishi et al., "Delta-1 Enhances Marrow and Thymus Repopulating Ability of Human CD34+CD38–Cord Blood Cells", *The Journal of Clinical Investigation*, 110(8):1165-1174 (2002).

Okazaki et al., "Characteristics and Partial Purification of a Novel Cytosolic, Magnesium-Independent, Neutral Sphingomyelinase Activated in the Early Signal Transduction of 1a,25-

(56) References Cited

OTHER PUBLICATIONS

Dihydroxyvitamin D3-Induced HL-60 Cell Differentiation", *The Journal of Biological Chemistry*, 269(6):4070-4077 (1994).
Okuno et al., "Differential regulation of the human and murine CD34 genes in hematopoietic stem cells", *Proc Natl Acad Sci U S A.*, 99(9):6246-51 (2002).
Olivares et al., "Copper As an Essential Nutrient", *Am. J. Clin. Nutr.*, 63:791S (1996).
Orlic et al., "Bone marrow cells regenerate infarcted myocardium", *Nature*, 410:701-705 (2001).
Orlic et al., "Exogenous Hematopoietic Stem Cells Can Regenerate Infarcted Myocardium", *Circulation*, 102:2672 (2000) (Abstract only).
Orlic et al., "Mobilized Bone Marrow Cells Repair the Infarcted Heart, Improving Function and Survival", *PNAS*, 98(18):10344-10324 (2001).
Orlic et al., "Transplanted Adult Bone Marrow Cells Repair Myocardial Infarcts in Mice", *Ann. N.Y. Acad. Sci.*, 938:221-230 (2001) (Abstract Only).
Osawa et al., "Long-Term Lymphohematopoietic Reconstitution by a Single CD34+-Low/Negative Hematopoietic Stem Cell", *Science*, 273(5272):242-245 (1996).
Ostrakhovitch et al., "Copper Ions Strongly Activate the Phosphoinositide-3-Kinase/Akt Pathway Independent of the Generation of Reactive Oxygen Species", *Arch. Biochem. Biophy.*, 397(2):232-239 (2002).
Pack et al., "Improved Bivalent Miniantibodies, With Identical Avidity as Whole Antibodies, Produced by High Cell Density Fermentation of *Escherichia coli*", *Bio/Technology*, 11:1271-1277 (1993).
Paling et al., "Regulation of Embryonic Stem Cell Self-Renewal by Phosphoinositide 3-Kinase-Dependent Signaling", *J. Bio. Chem.*, 279(46):48063-48070 (2004).
Palmiter, "Regulation of Metallothionein Genes by Heavy Metals Appears to Be Mediated by a Zinc-Sensitive Inhibitor That Interacts With a Constitutively Active Transcription Factor, MTF-1", *Proc. Natl. Acad. Sci. USA*, 91(4):1219-1223 (1994).
Park et al., "Phosphatidylinositol 3-kinase regulates PMA-induced differentiation and superoxide production in HL-60 cells", *Immunopharmacol. Immunotoxicol.*, 24(2):211-226 (2002).
Pei et al., "Bioreactors Mediate the Effectiveness of Tissue Engineering Scaffolds", *The FASEB Journal*, 16:1691-1694 (2002).
Peled et al., "Cellular Copper Content Modulates Differentiation and Self-Renewal in Cultures of Cord Blood-Derived CD34+ Cells", *British Journal of Haematology*, 116(3):655-661 (2002).
Peled et al., "Chelatable Cellular Copper Modulates Differentiation and Self-Renewal of Cord Blood-Derived Hematopoietic Progenitor Cells", *Exp. Hematol.*, 33:1092-1100 (2005).
Peled et al., "Cooper Chelators Sustain Long-Term Expansion of Cord-Blood CD 34 + Cultures Initiated With IL-3 and G-CSF—Late Acting, Differentiation-Inducing Cytokines", *Blood*, 96(1):773a (Abstract 3343) (2000).
Peled et al., "Copper chelators enable long term CFU and CD34+ cells expansions in cultures initiated with the entire mononuclear cell (MNC) fraction.", *Blood*, 100(11) (2002). Abstract # 4076.
Peled et al., "Dependence of Human Stem Cell Engraftment and Repopulation of NOD/SCID Mice on CXCR4", *Science*, 283:845-848 (1999).
Peled et al., "Identification of a Serum-Derived Differentiation-Inducing Activity as the Copper-Binding Protein Ceruloplasmin", *Blood*, 92(10, Suppl.1, Part 1-2):618A-619A (Abstract 2551) (1998).
Peled et al., "Linear Polyamine Copper Chelator Tetraethylenepentamine Augments Long-Term Ex Vivo Expansion of Cord Blood-Derived CD34+ Cells and Increases Their Engraftment Potential in NOD/SCID Mice", *Exper. Hemat.*, 32:547-555 (2004).
Peled et al., "Regulation of Long-Term Expansion of Hemopoietic Stem/Progenitor Cells (HPC) by Intracellular Copper Content", *Blood*, 96(Part 1):776a-777a (2000).

Pera, "Human pluripotent stem cells: a progress report", *Curr. Opin. Gen. Devel.*, 11:595-599 (2001).
Percival et al., "Copper Is Required to Maintain Cu/Zn-Superoxide Dismutase Activity During HL-60 Cell Differentiation", *Proc. Soc. Exp. Biol. Med.*, 203:78-83 (1993).
Percival et al., "HL-60 Cells Can Be Made Copper Deficient by Incubating with Tetraethylenepentamine", *J. Nutr.*, 122(12):2424-2429 (1992).
Percival, "Copper and Immunity", *American Journal of Clinical Nutrition*, 67(5 Suppl.):1064S-1068S (1998). p. 1066, 1-h col., § 2, r-h col., § 2. // EP/OA of 12.1.05 in 21437; EP/OA of 20.4.06 in 20816;EP/OA of 20.4.06 in 25695.
Percival, "Neutropenia Caused by Copper Deficiency: Possible Mechanisms of Action", *Nutr. Rev.*, 53(3):59-66 (1995).
Perrotti et al., *Mol. Cell. Biol.*, 15(11):6075-6087 (1995).
Peters et al., "Long-Term Ex Vivo Expansion of Human Fetal Liver Primitive Haematopoietic Progenitor Cells in Stroma-Free Cultures", *Brit. J Haemat.*, 119:792-802 (2002).
Petersen et al., "Bone Marrow as a Potential Source of Hepatic Oval Cells", *Science*, 284(5417):1168-1170 (1999) (Abstract).
Petersen et al., "Hepatic Oval Cells Express the Hematopoietic Stem Cell Marker Thy-1 in the Rat", *Hepatology*, 27(2):433-445 (1998).
Petti et al., "Complete Remission Through Blast Cell Differentiation in PLZF/RARa-Positive Acute Promyelocytic Leukemia: In Vitro and In Vivo Studies", *Blood*, 100(3):1065-1067 (2002).
Petzer et al., "Differential Cytokine Effects on Primitive (CD34+CD38–) Human Hematopoietic Cells: Novel Responses to Flt3-Ligand and Thrombopoietin", *Journal of Experimental Medicine*, 183:2551-2558 (1996).
Petzer et al., "Self-Renewal of Primitive Human Hematopoietic Cells (Long-Term-Culture-Initiating Cells) In Vitro and Their Expansion in Defined Medium", *Proc. Natl. Acad. ScL U.S.A.*, 93:1470-1474 (1996).
Piacibelio et al., "Extensive Amplification and Self-Renewal of Human Primitive Hematopoietic Cells from Cord Blood", *Blood*, 89(8):2644-2653 (1997).
Pickart et al., "Growth Modulating Plasma Tripeptide May Function by Facilitating Copper Uptake Into Cells", *Nature*, 288(18/25):715-717 (1980) (Abstract). p. 716, col. 2, Line I.
Podestá et al., "Cyclic ADP-Ribose Generation by CD38 Improves Human Hemopoietic Stem Cell Engraftment Into NOD/SCID Mice", *The FASEB Journal*, 17:310-312 (2003).
Podestá et al., "Extracellular Cyclic ADP-Ribose Increases Intracellular Free Calcium Concentration and Stimulates Proliferation of Human Hematopoietic Progenitors", FASEB Journal, 14(5):680-690 (2000). Fig .1.
Porter et al., "Graft-Versus-Leukemia Effect of Allogeneic Bone Marrow Transplantation and Donor Mononuclear Cell Infusions", *Cancer Treatment & Research*, 77:57-85 (1997). Abstract.
Porter, "The Hydrolysis of Rabbit y-Globulin and Antibodies With Crystalline Papain", *Biochemical Journal*, 73:119-126 (1959).
Presta, "Antibody Engineering", *Current Opinion in Structural Biology*, 2:593-596 (1992).
Puccetti at al., "AML-Associated Translocation Products Block Vitamin D3-Induced Differentiation by Sequestering the Vitamin D3 Receptor", *Cancer Research*, 62:7050-7058 (2002).
Punzel et al., "The Type of Stromal Feeder Used in Limiting Dilution Assays Influences Frequency and Maintenance Assessment of human Long-Term Culture Initiating Cells", *Leukemia*, 13:92-97 (1999).
Purdy et al., "Large Volume Ex Vivo Expansion of CD34+-Positive Hematopoietic Progenitor Cells for Transplantation", *Journal of Hematotherapy*, 4:515-525 (1995).
Purton et al., "All-Trans Retinoic Acid Delays the Differentiation of Primitive Hematopoietic Precursors ($lin^{-ckit+Sca-1+}$) *While Enhancing the Terminal Maturation of Committed Granulocyte/Monocyte Progenitors*", *Blood*, 94(2):483-495 (1999).
Purton et al., "All-Trans Retinoic Acid Enhances the Long-Term Repopulating Activity of Cultured Hematopoietic Stem Cells", *Blood*, 95(2):470-477 (2000) (Abstract).
Purton et al., "All-Trans Retinoic Acid Facilities Oncoretrovirus-Mediated Transduction of Hematopoietic Repopulating Stem Cells", *J. Hematother. Stem Cell Res.*, 10(6):815-825 (2001) (Abstract).

(56) References Cited

OTHER PUBLICATIONS

Quantin et al., "Adenovirus as an Expression Vector in Muscle Cells In Vivo", *Proc. Natl. Acad. Sci. USA*, 89:2581-2584 (1992).
Rajur et al., "Covalent Protein-Oligoneucleotide Conjugates for Efficient Delivery of Antisense Molecules", *Bioconjugate Chemistry*, 8(6):935-940 (1997).
Ramsfjell et al., "Distinct Requirements for Optimal Growth and In Vitro Expansion of Human CD34+CD38- Bone Marrow Long-Term Culture-Initiating Cells (LTC-IC), Extended LTC-IC, and Murine in Vivo Long-Term Reconstituting Stem Cells", *Blood*, 94(12):4093-4102 (1999).
Rankin et al., "Quantitative Studies of Inhibitors of ADP-Ribosylation in Vitro and in Vivo", *J. Biol. Chem.*, 264(8):4312-4317 (1989).
Ratajczak et al., "Effect of Basic (FGF-2) and Acidic (FGF-1) Fibroblast Growth Factors on Early Haemopoietic Cell Development", *British Journal of Hematology*, 93:772-782 (1996).
Ratajczak et al., "Hunt for pluripotent stem cell-regenerative medicine search for almighty cell", *J Autoimmun*, 30:151-162 (2008).
Reeves et al., "High Zinc Concentrations in Culture Media Affect Copper Uptake and Transport in Differentiated Human Colon Adenocarcinoma Cells", *Journal of Nutrition*, 126(6):1701-1712 (1996) (Abstract).
Reid et al., "Interactions of Tumor Necrosis Factor With Granulocyte-Macrophage Colony-Stimulating Factor and Other Cytokines in the Regulation of Dendritic Cell Growth In Vitro From Early Bipotent CD34+ Progenitors in Human Bone Marrow", *Journal of Immunology*, 149(8):2681-2688 (1992) (Abstract). p. 2686, col. 1, 2nd §, p. 2682, col. 1, 2nd §.
Reya, "Regulation of Hematopoietic Stem Cell Self-Renewal", *Recent Progress in Hormone Res.*, 58:283-295 (2003).
Reyes et al., "Origin of Endothelial Progenitors in Human Postnatal Bone Marrow", *Journal of Clinical Investigation*, 109:337-346 (2002).
Riechmann et al., "Reshaping Human Antibodies for Therapy", *Nature*, 332:323-327 (1988).
Roach et al., "Methods for the Isolation and Maintenance of Murine Embryonic Stem Cells", *Methods in Molecular Biology—Embryonic Stem Cells: Methods and Protocols*, 185:1-16 (2002).
Roberts, "Mesenchymal Stem Cells", *Vox Sanguinis*, 87(Suppl. 2):s38-s41 (2004).
Robinson et al., "Ex Vivo Expansion of Umbilical Cord Blood", *Cytotherapy*, XP009120788, 7(3):243-250 (2005).
Rosenfeld et al., "Adenovirus-Mediated Transfer of a Recombinant al-Antitrypsin Gene to the Lung Epithelium In Vivo", *Science*, 252:431-434 (1991).
Rosenfeld et al., "In Vivo Transfer of the Human Cystic Fibrosis Transmembrane Conductance Regulator Gene to the Airway Epithelium", *Cell*, 68:143-155 (1992).
Ross et al., "Chelometric Indicators Titrations With the Solid-State Cupric Ion-Selective Electrode", *Analytical Chemistry*, 41(13):1900-1902 (1969).
Rusten et al., "The RAR-RXR as Well as the RXR-RXR Pathway is Involved Signaling Growth Inhibition of Human CD34+ Erythroid Progenitor Cells", *Blood*, 87(5):1728-1736 (1996) (Abstract).
Ryu et al., "Adenosine Triphosphate Induces Proliferation of Human Neural Stem Cells: Role of Calcium and P70 Ribosomal Protein S6 Kinase", *Journal of Neuroscience Research*, 72:352-362 (2003).
Sammons et al., "Mechanisms Mediating the Inhibitory Effect of All-Trans Retinoic Acid on Primitive Hematopoietic Stem Cells in Human Long-Term Bone Marrow Culture", *Stem Cells*, 18(3):214-219 (2000).
Samulski et al., "Helper-Free Stocks of Recombinant Adeno-Associated Viruses: Normal Integration Does Not Require Viral Gene Expression", *Journal of Virology*, 63(9):3822-3828 (1989).
Santoro et al., "A General Purpose RNA-Cleaving DNA Enzyme", *Proc. Natl. Acad. Sci. USA*, 94:4262 4266 (1997).
Sato et al., "In Vitro Expansion of Human Peripheral Blood CD34+ Cells", *Blood*, 82(12):3600-3609 (1993).

Sauve et al., "Mechanism-Based Inhibitors of CD38: A Mammalian Cyclic ADP-Ribose Synthetase", *Biochemistry*, 41(26):8455-8463 (2002).
Schechter et al., The Molecular Basis of Blood Diseases, p. 179-218 (1987).
Schmetzer et al., "Effect of GM-CSF, 1,25-Dihydroxycholecalciferol (Vit. D) and All-Trans-Retinocin Acid (ATRA) on the Proliferation and Differentiation of MDS-Bone Marrow (BM)-Cells In Vitro", *Hematology*, 2: 11-19 (1997).
Schwartz et al., "In Vitro Myelopoiesis Stimulated by Rapid Medium Exchange and Supplementation With Hematopoietic Growth Factors", *Blood*, 78(12):3155-3161 (1991).
Seed, "An LFA-3 cDNA Encodes a Phospholipid-Linked Membrane Protein Homologous to Its Receptor CD2", *Nature*, 329:840-842 (1987).
Segev et al., "Differentiation of Human Embryonic Stem Cells Into Insulin-Producing Clusters", *Stem Cells*, XP009038283, 22(3):265-274, (2004) (Abstract).
Sekhar et al., "Retroviral Transduction of CD34-Enriched Hematopoietic Progenitor Cells Under Serum-Free Conditions", *Human Gene Therapy*, 7:33-38 (1996).
Selden, "Transfection Using DEAE-Dextran", *Short Protocols in Molecular Biology*, Unit 9.2: 9-9-9-11 (1984).
Sergeant et al., "Iron and Copper Requirements for Proliferation and Differentiation of a Human Promyelocytic Leukemia Cell Line (HL-60)", *Journal of Cellular Physiology*, 163(3):477-485 (1995).
Shimakura et al., "Murine Stromal Cell Line HESS-5 Maintains Reconstituting Ability of Ex Vivo-Generated Hematopoietic Stem Cells From Human Bone Marrow and Cytokine-Mobilized Peripheral Blood", *Stem Cells*, 18:183-189 (2000).
Shimizu et al., "Treatment and Management of Wilson's Disease", *Pediatr. Int.*, 41(4):419-422 (1999) (Abstract).
Shioda et al., "Anti-HIV-1 and Chemotactic Activities of Human Stromal Cell-Derived Factor la (SDFla) and SDF-11 Are Abolished by CD26/Dipeptidyl Peptidase IV-Mediated Cleavage", *Proc. Natl. Acad. Sci. USA*, 95:6331-6336 (1998).
Sigurdsson et al., "Copper Chelation Delays the Onset of Prion Disease", *J. Biol. Chem.*, 278(47):46199-46202 (2003) (Abstract).
Silvennoinen et at., "CD38 signal transduction in human B cell precursors. Rapid induction of tyrosine phosphorylation, activation of syk tyrosine kinase, and phosphorylation of phospholipase C-gamma and phosphatidylinositol 3-kinase", *J. Immunol.*, 156(1):100-107 (1996) (Abstract Only).
Simon et al., "Copper Deficiency and Sideroblastic Anemia Associated with Zinc Ingestion", *Am. J. Hematol.*, 28(3):181-183 (1988).
Slavin et al., "Donor Lymphocyte Infusion: The Use of Alloreactive and Tumor-Reactive Lymphocytes for Immunotherapy of Malignant and Nonmalignant Diseases in Conjunction With Allogeneic Stem Cell Transplantation", *Journal of Hematotherapy & Stem Cell Research*, 11:265-276 (2002).
Slavin et al., "Treatment of Leukemia by Alloreactive Lymphocytes and Nonmyeloablative Stem Cell Transplantation", *Journal of Clinical Immunology*, 22(2):64-69 (2002).
Smith, "Embryo-Derived Stem Cells: of Mice and Men", *Annual Reviews of Cell and Developmental Biology*, 17:435-462 (2001).
Smith, "The World According to PARP", *Trends in Biochemical Sciences*, 26(3):174-179 (2001).
Spencer et al., "Controlling Signal Transduction With Synthetic Ligands", *Science*, 262:1019-1024 (1993).
Sprangrude et al., "Purification and Characterization of Mouse Hematopoietic Stem Cells", *Science*, 241(4861):58-62 (1988).
Struyf et al., "Natural Truncation of RANTES Abolishes Signaling Through the CC Chemokine Receptors CCR1 and CCR3, Impairs Its Chemotactic Potency and Generates a CC Chemokine Inhibitor", *European Journal Immunology*, 28:1262-1271 (1998).
Suda et al., "A Study of Trientine Therapy in Wilson's Disease With Neurology Symptoms", *No To Hattatsu*, 25(5): 429-434 (1993) (Abstract).
Szilvassy et al., "Differential Homing and Engraftment Properties of Hematopoetic Progenitor Cells From Murine Bone Marrow Mobilized Peripheral Blood Cells and Fetal Liver", *Blood*, 98(7):2108-2115 (2001).

(56) References Cited

OTHER PUBLICATIONS

Takeshita et al., "Selective Stimulation by Ceramide of the Expression of the a Isoform of Retinoic Acid and Retinoid X Receptors in Osteoblastic Cells", *Journal of Biological Chemistry*, 275(41):32220-32226 (2000).
Tashiro-Itoh et al., "Metallothionein Expresion and Concentrations of Copper and Zinz are associated with Tumor Differentiation in Hepatocellular Carcinoma", *Liver*, 17(6):300-306 (1997).
Tateishi-Yuyama et al., "Therapeutic angiogenesis for patients with limb ischaemia by autologous transplantation of bone-marrow cells: a pilot study and a randomid controlled trial", *The Lancet*, 360:427-435 (2002).
Tateno et al., "Long-term cultivation of adult rat hepatocytes that undergo multiple cell divisions and express normal parenchymal phenotypes.", *Am. J Pathol.*, 148(2):383-392 (1996).
Todisco et al., "CD38 Ligation Inhibits Normal and Leukemic Myelopoiesis", *Blood*, 95(2):535-542 (2000) (Abstract).
Tratschin et al., "A Human Parvovirus, Adeno-Associated Virus, as a Eucaryotic Vector: Transient Expression and Encapsidation of the Procaryotic Gene for Chloramphenicol Acetyltransferase", *Molecular and Cellular Biology*, 4(10):2072-2081 (1984).
Tratschin et al., "Adeno-Associated Virus Vector for High-Frequency Integration, Expression, and Rescue of Genes in Mammalian Cells", *Molecular and Cellular Biology*, 5(11):3251-3260 (1985).
Tratschin et al., "Genetic Analysis of Adeno-Associated Virus: Properties of Deletion Mutants Constructed In Vitro and Evidence for an Adeno-Associated Virus Replication Function", *Journal of Virology*, 51(3):611-619 (1984).
Trounson, "The Derivation and Potential Use of Human Embryonic Stem Cells", *Reproduction, Fertility and Development*, 13(7-8):523-532 (2001).
Tse et al., "Angiogenesis in Ischaemic Myocardium by Intramyocardial Autologous Bone Marrow Mononuclear Cell Implantation", *Lancet*, 361:47-49 (2003).
Tuba et al., "Synthesis and Structure—Activity Relationships of Neuromuscular Blocking Agents", *Current Medicinal Chemistry*, 9:1507-1536 (2002).
Turnpenny et al., "Evaluating human embryonic germ cells: concord and conflict as pluripotent stem cells", *Stem Cells*, 24:212-220 (2006).
Ueno et al., "A Novel Retinoic Acid Receptor (RAR)-Selective Antagonist Inhibits Differentiation and Apoptosis of HL-60 Cells: Implications of RARa-Mediated Signals in Myeloid Leukemic Cells", *Leukemia Research*, 22(6):517-525 (1998).
Vaca et al., "Nicotinamide Induces Both Proliferation and Differentiation of Embryonic Stem Cells Into Insulin-Producing Cells", *Transplantion Proceedings*, XP002539110, 35(5):2021-2023 (2003) (Abstract).
Van Beusechem et al., "Long-Term Expression of human Adenosine Deaminase in Rhesus Monkeys Transplanted With Retrovirus-Infected Bone-Marrow Cells", *Proc. Natl. Acad. Sci. USA*, 89:7640-7644 (1992).
Van Epps et al., "Harvesting, Characterization, and Culture of CD34+ Cells From Human Bone Marrow, Peripheral Blood, and Cord Blood", *Blood Cells*, 20(2-3):411-423 (1994) (Abstract).
Verfaillie, "Can Human Hematopoietic Stem Cells Be Cultured Ex Vivo?", *Stem Cells*, 12(5):466-476 (1994) (Abstract).
Verfaillie, "Direct Contact Between Human Primitive Hematopoietic Progenitors and Bone Marrow Stroma Is Not Required for Long-Term In Vitro Hematopoiesis", *Blood*, 79(11):2821-2826 (1992).
Verhoeyen et al., "Reshaping Human Antibodies: Grafting an Antilysozyme Activity", *Science*, 239:1534-1536 (1988).
Verlinden et al., "Interaction of Two Novel 14-Epivitamin D3 Analogs With Vitamin D3 Receptor-Retinoid X Receptor Heterodimers on Vitamin D3 Response Elements", *Journal of Bone and Mineral Research*, 16(4):625-638 (2001).
Vilensky et al., "British Anti-Lewisite (Dimercaprol): an Amazing History", *Ann. Emerg. Med.*, 41(3):378-83 (2003) (Abstract).

Virág et al., "The Therapeutic Potential of Poly(ADP-Ribose) Polymerase Inhbititors", *Pharmacological Reviews*, 54(3):375-429 (2002).
Vlahos et al., "A specific inhibitor of phosphatidylinositol 3-kinase, 2-(4-morpholinyl)-8-phenyl-4H-1-benzopyran-4-one (LY294002)", *I Biol. Chem.*, 269(7):5241-5248 (1994).
Wall et al., "Inhibition of the Intrinsic NAD+ Glycohydrolase Activity of CD38 by Carbocyclic NAD Analogues", *Biochemical Journal*, 335(3):631-636 (1998).
Walton et al., "Prediction of Antisense Oligonucleotide Binding Affinity to a Structured RNA Target", *Biotechnology and Bioengineering*, 65(1):1-9 (1999).
Wang et al., "In Vitro Culture of Umbilical Cord Blood MNC and CD34+ Selected Cells", *Sheng Wu Gong Cheng Xue Bao*, 18(3):343-347 (2002) (Abstract).
Wang et al., "PH-Sensitive Immunoliposomes Mediate Target-Cell-Specific Delivery and Controlled Expression of a Foreign Gene in Mouse", *Proc. Natl. Acad. Sci. USA*, 84:7851-7855 (1987).
Wasa et al., "Copper Deficiency with Pancytopenia During Total Parental Nutrition", *J. Parenter. Enteral. Nutr.*, 18(3):190-192 (1994).
Weissmann, "Translating Stem and Progenitor Cell Biology to the Clinic: Barriers and Opportunities", *Science*, 287(5457):1442-1446 (2000) (Abstract).
Wendling et al., "Retinoid X Receptor Are Essential for Early Mouse Development and Placentogenesis", *Proc. Natl. Acad. Sci. USA*, 96(2):547-551 (1999).
Whitlow et al., "Single-Chain Fv Proteins and Their Fusion Proteins", *Methods: A Companion to Methods in Enzymology*, 2(2):97-105 (1991).
Wick et al., "New ways in hepatocyte cultures: Cell immobilisation technique", *ALTEX*, 14(2):51-56 (1997) (Abstract Only).
Wilson et al., "Hepatocyte-Directed Gene Transfer In Vivo Leads to Transient Improvement of Hypercholesterolemia in Low Density Lipoprotein Receptor-Deficient Rabbits", *The Journal of Biological Chemistry*, 267(2):963-967 (1992).
Wilson et al., "Retrovirus-Mediated Transduction of Adult Hepatocytes", *Proc. Natl. Acad. Sci. USA*, 85:30143018 (1988).
Wolff et al., "Direct Gene Transfer Into Mouse Muscle In Vivo", *Science*, 247:1465-1468 (1990).
Wondisford et al., "Cloning of the Human Thyrotropin B-Subunit Gene and Transient Expression of Biologically Active Human Thyrotropin After Gene Transfection", *Molecular Endocrinology*, 2:32-39 (1988).
Wu et al., "Receptor-Mediated Gene Delivery and Expression In Vivo", *The Journal of Biological Chemistry*, 263(29):14621-14624 (1988).
Wulf et al., "Somatic Stem Cell Plasticity: Current Evidence and Emerging Concepts", *Exp. Hemat.*, 29:1361-1370 (2001).
Xia et al., "Surface Fucosylation of Human Cord Blood Cells Augments Binding to P-Selectin and E-Selectin and Enhances Engraftment in Bone Marrow", *Blood*, 104(10):3091-3096 (2004).
Yang et al., "In vitro trans-differentiation of adult hepatic stem cells into pancreatic endocrine hormone-producing cells", *Proc. Natl. Acad. Sci. U.S.A.*, 99(12):8078-8083 (2002).
Yau et al., "Endogenous Mono-ADP-Ribosylation Mediates Smooth Muscle Cell Proliferation and Migration Via Protein Kinase Induction of C-Fos Expression", *European Journal of Biochemistry*, 270:101-110, 2003.
Yin et al., "AC133, A Novel Marker for Human Hematopoietic Stem and Progenitor Cells", *Blood*, 90(12):50025012 (1997).
Ylä-Herttuala et al., "Genetransfer as, a tool to induce therapeutic vascular growth", *Nature Medicine*, 9(6):694-701 (2003).
Zidar et al., "Observations on the Anemia and Neutropenia of Human Copper Deficiency", *Am. J. Hematol.*, 3:177-185 (1977).
Zocchi et al., "Ligand-Induced Internalization of CD38 Results in Intracellular Ca2+ Moblization: Role of NAD+ Transport Across Cell Membranes", *FASEB J.*, 13(2):273-283 (1999) (Abstract).
Zon et al., "Developmental Biology of Hematopoiesis", *Blood*, 86(8):2876-2891 (1995).

(56) References Cited

OTHER PUBLICATIONS

Blyszczuk et al. "Embryonic Stem Cells Differentiate Into Insulin-Producing Cells Without Selection of Nestin-Expressing Cells", International Journal of Developmental Biology, 48: 1095-1104, 2004.
Chivu et al. "In Vitro Hepatic Differentiation of Human Bone Marrow Mesenchymal Stem Cells Under Differential Exposure to Liver-Specific Factors", Translational Research, 154(3): 122-132, Sep. 2009. Abstract.
Communication Pursuant to Article 94(3) EPC Dated Nov. 17, 2009 From the European Patent Office Re.: Application No. 05784625.5.
Response Dated Mar. 4, 2010 to Communication Pursuant to Article 94(3) EPC of Nov. 17, 2009 From the European Patent Office Re.: Application No. 05784625.5.
Response Dated Mar. 8, 2010 to Official Action of Oct. 23, 2009 From the US Patent and Trademark Office Re.: U.S. Appl. No. 11/606,525.
Response Dated Feb. 18, 2010 to Communication Pursuant to Article 94(3) EPC of Aug. 20, 2009 From the European Patent Office Re.: Application No. 06821601.9.
Response Dated Dec. 23, 2008 to Official Action of Nov. 25, 2008 From the US Patent and Trademark Office Re.: U.S. Appl. No. 11/606,525.
Response Dated Jan. 31, 2010 to Search Report and Written Opinion of Aug. 10, 2009 From the Intellectual Property Office of Singapore Issued by the Australian Patent Office Re.: Application No. SG 200804154-3.
Zulewski et al. "Multipotential Nestin-Positive Stem Cells Isolated From Adult Pancreatic Islets Differentiate Ex Vivo Into Pancreatic Endocrine, Exocrine, and Hepatic Phenotypes", Diabetes, 50: 521-533, 2001.
"13th Annual Meeting on Surgical Research." *Langenbeck's Archives of Surgery*. 394.5(2009):915-970.
Bonora-Centelles et al. "Sequential Hepatogenic Transdifferentiation of Adipose Tissue-Derived Stem Cells: Relevance of Different Extracellular Signaling Molecules, Transcription Factors Involved, and Expression of New Key Marker Genes." *Cell Transplant*. 18.12(2009):1319-1340.
van Poll et al. "Mesenchymal Stem Cell-Derived Molecules Directly Modulate Hepatocellular Death and Regeneration In Vitro and In Vivo" *Hepatol*. 47.5(2008):1634-1643.
"Trientine (Systemic)." *MEDLINEplus Drug Information*. Retrieved Jan. 12, 2004.
Alici et al. "Autologous Antitumor Activity by NK Cells Expanded From Myeloma Patients Using GMP-Compliant Components." *Blood*. 111.6(2008):3155-3162.
Boitano et al. "Aryl Hydrocabron Receptor Antagonists Promote the Expansion of Human Hematopoietic Stem Cells." *Science*. 329. 5997(2010):1345-1348.
Collins et al. "Stirred Culture of Peripheral and Cord Blood Hematopoietice Cells Offers Advantages over Traditional Static Systems for Clinically Relevant Applications." *Biotechnol. Bioeng*. 59.5(1998):534-543.
De Ridder et al. "Hypoxic Tumor Cell Radiosensitization: Role of the iNOS/NO Pathway." *Bull. Cancer*. 95.3(2008):282-291.
Freshney, ed. "Culture of Specific Cell Types." *Culture of Animal Cells*. New York: John Wiley and Sons. Third Ed. (1994):309-311, 327-328.
Kahn et al. "Overexpression of CXCR4 on Human CD34+ Progenitors Increases Their Proliferation, Migration, and NOD/SCID Repopulation." *Blood*. 103.8(2004):2942-2949.
Nguyen et al. "The Search for Endogenous Activators of the Aryl Hydrocarbon Receptor." *Chem. Res. Toxicol*. 21.1(2008):203-116.
Olson et al. "Tissue-Specific Homing and Expansion of Donor NK Cells in Allogeneic Bone Marrow Transplantation." *J. Immunol*. 183(2009):3219-3228.
Peled et al. "Nicotinamide Modulates Ex-Vivo Expansion of Cord Blood Derived CD34+ Cells Cultured With Cytokines and Promotoes Their Homing and Engraftment in SCID Mice." *Blood*. 108(2006):218A. (Abstract #725).
Sieff et al. "Changes in Cell Surface Antigen Expression During Hemopoietic Differentiation." *Blood*. 60.3(1982):703-713.
Verneris et al. "The Phenotypic and Functional Characteristics of Umbilical Cord Blood and Peripheral Blood Natural Killer Cells." *Brit. J. Haematol*. 147(2009):185-191.
Zhang et al. "Flavonoids as Aryl Hydrocarbon Receptor Agonists/Antagonists: Effects of Structure and Cell Context." *Environ. Health Persp*. 111.16(2003):1877-1882.
Bachanova et al. "Allogeneic Natural Killer Cells for Refractory Lymphoma." *Cancer Immunol. Immunother*. 59(2010):1739-1744.
Beider et al. "Involvement of CXCR4 and IL-2 in the Homing and Retention of Human NK and NK T Cells to the Bone Marrow and Spleen of NOD/SCID Mice." *Blood*. 102.6(2003):1951-1958.
Berg et al. "Clinical-Grade ex vivo-Expanded Human Natural Killer Cells Up-Regulate Activating Receptors and Death Receptor Ligands and Have Enhanced Cytolytic Activity Against Tumor Cells." *Cythotherapy*. 11.3(2009):341-355.
Bernardini et al. "CCL3 and CXCL12 Regulate Trafficking of Mouse Bone Marrow NK Cell Subsets." *Blood*. 111.7(2008):3626-3634.
Caligiuri. "Human Natural Killer Cells." *Blood*. 112.3(2008):461-469.
Cho et al. "Expansion and Activation of Natural Killer Cells for Cancer Immunotherapy." *Korean J. Lab. Med*. 29.2(2009):89-96.
Decot et al. "Natural-Killer Cell Amplification for Adoptive Leukemia Relapse Immunotherapy: Comparison of Three Cytokines, IL-2, IL-15, or IL-7 and Impact on NKG2D, KIR2DL1, and KIR2DL2 Expression." *Exp. Hematol*. 38.5(2010):351-362.
Frias et al. "Generation of Functional Natural Killer and Dendritic Cells in a Human Stromal-Based Serum-Free Culture System Designed for Cord Blood Expansion." *Exp. Hematol*. 36(2008):61-68.
Harada et al. "A Wilms Tumor Cell Line, HFWT, Can Greatly Stimulate Proliferation of CD56+ Human Natural Killer Cells and Their Novel Precursors in Blood Mononuclear Cells." *Exp. Hematol*. 32(2004):614-621.
Humeau et al. "Successful Reconstitution of Human Hematopoiesis in the SCID-hu Mouse by Genetically Modified, Highly Enriched Progenitors Isolated from Fetal Liver." *Blood*. 90.9(1997):3496-3506.
Klingemann et al. "Ex vivo Expansion of Natural Killer Cells for Clinical Applications." *Cythotherapy*. 6.1(2004):15-22.
Koehl et al. "Ex vivo Expansion of Highly Purified NK Cells for Immunotherapy After Haploidentical Stem Cell Transplantation in Children." *Klin. Pädiatr*. 217(2005):345-350.
Markel et al. "Natural Killer Lysis Receptor (NKLR)/NKLR-Ligand Matching as a Novel Approach for Enhancing Anti-Tumor Activity of Allogeneic NK Cells." *PLoS ONE*. 4.5(2009):e5597.
Meyer-Monard et al. "Clinical-Grade Purification of Natural Killer Cells in Haploidentical Hematopoietic Stem Cell Transplantation." *Transfusion*. 49(2009):362-371.
Miller et al. "Role of Monocytes in the Expansion of Human Activated Natural Killer Cells." *Blood*. 80.9(1992):2221-2229.
Robertson et al. "Biology and Clinical Relevance of Human Natural Killer Cells." *Blood*. 76.12(1990):2421-2438.
Rosenberg. "Lymphokine-Activated Killer Cells: A New Approach to Immunotherapy of Cancer." *J. Natl. Cancer Inst*. 75.4(1985):595-603.
Schleinitz et al. "Natural Killer Cells in Human Autoimmune Diseases." *Immunology*. 131(2010):451-458.
Von Drygalski et al. "Murine Bone Marrow Cells Cultured Ex Vivo in the Presence of Multiple Cytokine Combinations Lose Radioprotective and Long-Term Engraftment Potential." *Stem Cells Dev*. 13(2004):101-111.
Yu et al. "CD94 Surface Density Identifies a Functional Intermediary Between the CD56bright and CD56dim Human NK-Cell Subsets." *Blood*. 115.2(2010):274-281.
Zucchini et al. "Natural Killer Cells in Immunodefense Against Infective Agents." *Exp. Rev. Anti Infect. Ther*. 6.6(2008):867-885.

\* cited by examiner

Capture and arrest of CD34+ cells to immobilized VCAM-1 (0.5 ug/ml) under shear flow

METHODS OF IMPROVING STEM CELL HOMING AND ENGRAFTMENT

FIELD AND BACKGROUND OF THE INVENTION

The present invention relates to methods for improving homing, retention and engraftment efficiency of transplanted cells.

Bone marrow transplantation (BMT) is a clinical procedure in which pluripotent hematopoietic cells obtained from the bone marrow are transplanted into a patient. BMT is the treatment of choice in several hematological disorders, including malignancies, Severe Combined Immune Deficiencies (SCIDs), congenitally or genetically determined hematopoietic abnormalities, anemia, aplastic anemia, leukemia and osteopetrosis.

Primitive or pluripotent hematopoietic stem cells usually reside in the bone marrow, although cord blood is another functional source of transplantable hematopoietic stem/progenitor cells (Gluckman, E., et al 1989 N. Engl. J. Med. 321:1174). All of these primitive hematopoietic cells may be identified by their surface CD34 antigen. Hematopoietic stem cells differentiate along one of two major pathways—either into lymphoid stem cells or myeloid stem cells. Both further differentiate into progenitor cells for each type of mature blood cell. These progenitor cells have lost the capacity for self-renewal and are committed to a given cell lineage. Thus, lymphoid stem cells differentiate into T or B progenitor and myeloid stem cells differentiate into progenitor cells for erythrocytes, neutrophils, eosinophils, basophils, monocytes, mast cells, and platelets.

Under steady state conditions, the majority of hematopoietic stem and progenitor cells reside in the bone marrow and only a few of these cells are detectable in peripheral blood. However, stem cells may be mobilized into the peripheral blood by treatment with myelosuppressive agents and/or certain hematopoietic growth factors. Studies have demonstrated that peripheral blood stem cells (PBSC) infused in a host exhibit enhanced potential for engraftment as compared to bone marrow-derived stem and progenitor cells. Thus, PBSC mobilized by chemotherapy, hematopoietic growth factors or a combination of these modalities are currently used in both autologous and non-autologous transplantation settings [Anderlini, P. and Korbling, M. (1997) Stem. Cells 15, 9-17]. In the case of non-autologous transplantation, the donors of stem cells are healthy individuals and the procedure for mobilization of stem cells into the blood stream has to be achieved with minimal discomfort. In this case, stem cells mobilization with hematopoietic growth factors is preferred to mobilization with antiblastic drugs (i.e. cyclophosphamide).

In addition to stem and progenitor cells, more differentiated cells can be used for transplantation, for treatment of diseases or conditions of specific organs or tissues characterized by cell dysfunction or cell death. For many such diseases current medical therapies or surgical procedures are either inadequate or nonexistent. Cellular therapy can replace or augment existing tissue to provide restorative therapy for these conditions. Exemplary cell types suitable for transplantation include: neural tissue derived cells, hepatocytes, myocytes, retinal cells, endocrine cells, melanocytes, keratinocytes, and chondrocytes. It has been shown in both animal models and in human studies that engraftment of transplanted cells can successfully reestablish tissue function. Thus, neurons can be transplanted, for example, for Parkinson's Disease and other neurodegenerative disease. Muscle cells, such as myoblasts, can be transplanted for, for example, treatment of ischemic cardiac myopathy. Islet cells can be transplanted to treat diabetes and/or other insulin- and glucagon-related disease or conditions. Differentiated blood cells, such as lymphocytes and dendritic cells, can also be transplanted, for example, for adoptive immunotherapy with NK cells.

However, studies have shown that the majority of transplanted cells, such as hepatocytes and neural cells, are cleared from the body following transplantation, and do not localize to target organs or tissues (De Roos et al Transplantation 1997; 63:513-18; Gagandeep et al, Gene Therapy 1999; 6:729-36). Efforts to improve homing, retention and engraftment of transplanted cells, such as treatment of hepatocytes with Con A before implantation (Ito et al, Muscle Nerve 1998; 21:291-7) have been only marginally effective. Thus, efforts have been directed to methods for pooling and storage of the freshly prepared cells (see, for example, U.S. Pat. Nos. 6,713,245 and 6,821,779 to Koopmans et al), in order to provide greater numbers of cells for transplantation.

Following transplantation, cells must migrate towards their target tissues. Chemoattractants, such as certain of the cytokines (CXCL1-CXCL16, and CCL1-CCL-27) aid in steering the cells towards their objective. Stromal cell-derived factor 1α (SDF-1α), also termed CXCL12, is a powerful chemoattractant of CD34$^+$ cells, including hematopoietic stem cells and neural stem cells (Aiuti J. Exp. Med. 1997; 185:111-120) and is widely expressed in many tissues during development (McGrath Dev. Biol. 1999; 213:442-456) and adulthood (Imai Br. J. Haematol. 1999; 106:905-911). It also chemoattracts non-stem cells such as T lymphocytes. CXC chemokine receptor 4 (CXCR4) is the cognate receptor for SDF-1α and is expressed on stem cells. Recent studies have implicated SDF-1α/CXCR4 as a pathway that activates stem cells molecular programs and homing during injury (Jaime Imitola et al., Proc Natl Acad Sci USA. 2004 Dec. 28; 101(52): 18117-18122).

CD26/dipeptidylpeptidase IV (DPPIV) a membrane-bound extracellular peptidase that cleaves dipeptides such as SDF-1α from the N terminus of polypeptide chains after a proline or an alanine, is a non-lineage-specific antigen whose expression in hematopoietic and other cells is regulated by differentiation and activation. Proteolytic cleavage of chemokines has implications with respect to the ability of cells to be attracted and/or activated by chemokines (Baggiolini, M. 1998, Nature 392:565).

Several functional studies allude to the role CD26/DPPIV plays in migration and mobilization of T-cells and hematopoietic cells [Shioda et al. (1998) Proc. Natl. Acad. Sci. USA 95:6331]. Inhibition of endogenous CD26/DPPIV activity on CD34$^+$ cells was shown to enhance the chemotactic response of these cells to SDF-1α (Christopherson K W 2nd, et al., Science. 2004 Aug. 13; 305(5686):1000-1003; Christopherson K W 2nd, J Immunol. 2002 Dec. 15; 169(12):7000-7008), while N-terminal-truncation of SDF-1α with DPPIV results in failure to induce the migration of CD34$^+$ cord blood cells.

Nicotinamide (NA), the amide form of niacin (vitamin B3), is a base-exchange substrate and a potent inhibitor of NAD (+)-dependent enzymes endowed with mono- and poly-ADP-ribosyltransferase activities. ADP-ribosylation is implicated in the modification of a diverse array of biological processes (Corda D, Di Girolamo M. 2003; 22(9):1953-1958; Rankin P W, et al., J Biol Chem. 1989; 264:4312-4317; Banasik M. et al., J Biol Chem. 1992; 267:1569-1575; Ueda K, Hayaishi O, Annu Rev Biochem. 1985; 54:73-100; Smith S. Trends Biochem Sci. 2001; 26:174-179; Virág L, Szabó C. Pharm. Reviews. 2002; 54:375-429).

The endogenous ADP-ribosyl transferases responsible for mono- or poly-ADP-ribosylation reactions modify molecules involved in cell signaling, such as core histones (de la Cruz X, Lois S, et al., Bioessays. 2005; 27(2):164-75), the alpha-subunit of heterotrimeric GTP-binding (G) proteins, the small GTPase Rho, monomeric actin and elongation factor 2 (EF-2). These post-translational modifications lead to activation or inactivation of cell functions modulated by these proteins (Lupi R, et al., J Biol Chem. 2000; 275:9418-9424; Lupi R, et al. Biochem J. 2002:367:1-7; Yau L, et al., Eur. J. Biochem. 2003; 270:101-110).

U.S. Pat. Appl. 2004/0247574 teaches the use of CD26 inhibitors for improving engraftment efficiency of stem cell transplants by both improving stem cell homing to bone marrow and by increasing the number of mobilized donor stem cells. It does not teach down-regulation of CD26 surface expression but rather down regulation of CD26 catalytic activity. Specifically, U.S. Pat. Appl. 2004/0247574 does not teach the use of nicotinamide for down-regulating CD26 surface expression.

PCT Application IL03/00064 discloses the use of nicotinamide, and other inhibitors of CD38, for the inhibition of differentiation in ex-vivo expanding stem and progenitor cells. However, PCT IL03/00064 does not teach administration of nicotinamide for enhancing homing, retention and engraftment of cells, or administration of nicotinamide to stem and progenitor cells for short intervals of 3 days or less, administration of nicotinamide to non-stem and non-progenitor (i.e. committed) cell populations or the administration of nicotinamide without provision of conditions for cellular proliferation.

It is therefore the object of this invention to overcome the drawbacks described in the currently available treatments and provide compositions and methods for the enhancement of cell migration, retention and homing potential of transplanted cells.

SUMMARY OF THE INVENTION

According to one aspect of the present invention there is provided a method of enhancing cell engraftment potential, the method comprising ex-vivo or in-vitro subjecting a population of cells to an amount of nicotinamide for a period of time sufficient to enhance cell homing and engraftment potential, wherein the method is further characterized by at least one of the following:

(i) wherein said population of cells is a hematopoietic stem and/or progenitor cell population, and said period of time is selected insufficient for stem cell expansion, or under conditions insufficient for stem and/or progenitor cell expansion;

(ii) wherein said amount of nicotinamide and said period of time are selected sufficient to down regulate CD26 expression by cells of said population of cells but not for stem and/or progenitor cell expansion;

(iii) said population of cells does not include hematopoietic cells, hematopoietic stem cells, mononuclear cells, early liver progenitor cells, committed progenitor cells, non-hematopoietic stem and progenitor cells, or embryonic stem and progenitor cells;

(iv) said subjecting is in the absence of nutrients;
(v) said subjecting is in the absence of a cytokine;
(vi) said subjecting is in the absence of FLT-3 ligand;
(vii) said subjecting is in the absence of stem cell factor (SCF);
(viii) said subjecting is in the absence of granulocyte colony stimulating factor (GCSF);
(ix) said subjecting is in the absence of an early acting cytokine; and
(x) said subjecting is in the absence of a late acting cytokine.

According to another aspect of the present invention there is provided a method of transplanting cells in a subject, the method comprising: (a) ex-vivo subjecting a population of cells comprising the cells to an amount of nicotinamide for a period of time sufficient to enhance homing and engraftment in said cells; the method further characterized by at least one of the following:

(i) wherein said population of cells is a hematopoietic stem and/or progenitor cell population, and said period of time is selected insufficient for stem cell expansion, or under conditions insufficient for stem and/or progenitor cell expansion;

(ii) wherein said amount of nicotinamide and said period of time are selected sufficient to down regulate CD26 expression by cells of said population of cells but not for stem and/or progenitor cell expansion;

(iii) said population of cells does not include hematopoietic cells, hematopoietic stem cells, mononuclear cells, early liver progenitor cells, committed progenitor cells, non-hematopoietic stem and progenitor cells, or embryonic stem and progenitor cells;

(iv) said subjecting is in the absence of nutrients;
(v) said subjecting is in the absence of a cytokine;
(vi) said subjecting is in the absence of FLT-3 ligand;
(vii) said subjecting is in the absence of stem cell factor (SCF);
(viii) said subjecting is in the absence of granulocyte colony stimulating factor (GCSF);
(ix) said subjecting is in the absence of an early acting cytokine;
(x) said subjecting is in the absence of a late acting cytokine; and subsequently
(b) transplanting the cells in a subject in need thereof.

According to still further features in the described preferred embodiments the subject is a human subject.

According to still further features in the described preferred embodiments the nicotinamide is selected from the group consisting of nicotinamide, a nicotinamide analog, a nicotinamide metabolite, a nicotinamide analog metabolite and derivatives thereof.

According to still further features in the described preferred embodiments the population of cells is derived from an organ selected from the group consisting of a muscle, skin, a bone, a lymph organ, a pancreas, a liver, a gallbladder, a kidney, a digestive tract organ, a respiratory tract organ, a reproductive organ, a urinary tract organ, a blood-associated organ, a thymus, a spleen, a nervous system organ.

According to still further features in the described preferred embodiments the population of cells does not include hematopoietic cells, mononuclear cells, early liver progenitor cells, committed progenitor cells, non-hematopoietic stem and progenitor cells, or embryonic stem and progenitor cells.

According to still further features in the described preferred embodiments, the population of cells comprises stem cells.

According to still further features in the described preferred embodiments the stem cells are derived from a source selected from the group consisting of hematopoietic cells, umbilical cord blood cells, mobilized peripheral blood cells, bone marrow cells and embryonic stem and/or progenitor cells.

According to still further features in the described preferred embodiments the stem cells are derived from bone marrow or peripheral blood.

According to still further features in the described preferred embodiments the stem cells are derived from neonatal umbilical cord blood.

According to still further features in the described preferred embodiments the stem cells are derived from a mononuclear cell fraction.

According to still further features in the described preferred embodiments the stem cells are enriched for hematopoietic stem cells.

According to still further features in the described preferred embodiments the methods of enhancing stem cell engraftment potential and transplanting further comprising the step of selecting the population of cells enriched for hematopoietic stem cells prior to, concomitant with or following the step of ex-vivo subjecting.

According to still further features in the described preferred embodiments the selecting is effected via CD34

According to still further features in the described preferred embodiments the methods of enhancing stem cell engraftment potential and transplanting, further comprising the step of selecting the population of cells enriched for early hematopoietic stem cells prior to, concomitant with or following the step of ex-vivo subjecting.

According to still further features in the described preferred embodiments the selecting is effected via CD133.

According to still further features in the described preferred embodiments the selecting is effected via CD34/CD38.

According to still further features in the described preferred embodiments the period of time is between 1 and 18 weeks.

According to still further features in the described preferred embodiments the period of time is between 1 and 7 days.

According to still further features in the described preferred embodiments the period of time is between 2 and 4 days.

According to still further features in the described preferred embodiments the period of time is between 12-30 hours.

According to still further features in the described preferred embodiments the period of time does not exceed 72 hours.

According to still further features in the described preferred embodiments said population of cells is a hematopoietic stem and progenitor cell population, and said period of time is selected insufficient for stem cell expansion.

According to still further features in the described preferred embodiments said population of cells is a hematopoietic stem and progenitor cell population, and said subjecting is performed under conditions insufficient for stem cell expansion.

According to still further features in the described preferred embodiments said conditions insufficient for stem cell expansion are selected from the group consisting of absence of nutrients, absence of late acting cytokines and absence of early acting cytokines.

According to still further features in the described preferred embodiments said period of time is sufficient to down-regulate expression of CD26 on the cells, but insufficient for cell proliferation.

According to still further features in the described preferred embodiments a concentration of the nicotinamide is 0.01-60 mg/ml.

According to still further features in the described preferred embodiments the effective amount of nicotinamide is 1.0-40 mg/kg body weight.

According to still further features in the described preferred embodiments the effective amount of nicotinamide is 10-20 mg/kg body weight.

According to still another aspect of the present invention there is provided a cell population comprising the cells characterized by enhanced homing and/or engraftment according to the above methods.

According to an additional aspect of the present invention there is provided a pharmaceutical composition comprising as an active ingredient the cell population and a pharmaceutically acceptable carrier.

According to yet an additional aspect of the present invention there is provided use of nicotinamide for the manufacture of a medicament identified for improving stem cell engraftment and/or homing.

The present invention successfully addresses the shortcomings of the presently known configurations by providing methods for enhancing stem cell mobilization and migration, both prior to and following stem cell transplantation.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a is a histogram of the results of flow cytometry of recipient's bone marrow cells showing homing of CFSE+/CD34+ cells after transplantation. FIG. 1b is a histogram of the results of flow cytometry of recipient's bone marrow cells showing homing of total CFSE+ cells after transplantation. Homing of human cells is presented as number of positive events (cytometry) per 100,000 BM cells analyzed. Each bar represents the average ±SE of 3 independent experiments (6-7 mice/experimental group). Representative flow cytometry analysis of bone marrow cells from non-injected mice (FIG. 1c) and mice injected with non-cultured cells (FIGS. 1d and 1g), cells cultured with cytokines (FIGS. 1e and 1h) and cells cultured with cytokines and nicotinamide (FIGS. 1f and 1i) are shown. Total human cells that home to the BM are gated (see area R2) based on low side scatter (y axis) and log fluorescence distribution of CFSC expression (x axis) (FIGS. 1c-1f). The bright fluorescence of CFSE was sufficient to separate labeled human cells from unlabeled murine cells by at least 1 log. Cells gated in R2 were then analyzed for CFSE (x axis) and CD34-APC (y axis) (FIGS. 1g-1i). The upper and lower right quadrants represent total human cells while the upper right quadrant represents the human CD34+ cells that home to the BM;

FIGS. 4a and 4b show the percentage of human (CD45+) cells in the cell populations before transplantation: non-cultured CD34$^+$ cells (non-cultured, gray ovals), the entire progeny of cultures following 3-week exposure to cytokines alone (cytokines alone, closed ovals), or cytokines and nicotinamide (cytokines+NA, arrows). The percent of engraftment 4 weeks post transplantation was determined by flow cytometry of human CD45 cells in the NOD/SCID marrow (y-axis). The numbers of SCID repopulating cells (SRC) were calculated by plotting the engraftment frequencies at each dose. The resultant curves indicates the estimated frequency of SRCs within non-cultured CD34+ cells (FIG. 4c), culture with cytokines (FIG. 4d) or cytokines and nicotinamide (FIG. 4e). The number shown in each box indicates the calculated frequency of SRCs using the maximum likelihood estimator. FIG. 4f shows the immunophenotype of engrafted human cells in representative mice transplanted with the progeny of $12 \times 10^3$ CD34+ cells cultured for 3-weeks with nicotinamide, as determined by FACS. Mouse bone marrow cells were dually stained with FITC-conjugated anti-CD45 (human) and antibodies to human differentiation markers as indicated. Percentages of dual positive cells are shown within each quadrant. Note the greater than 7 fold enhancement of engraftment in the nicotinamide-treated mice (FIG. 4e), as compared with mice treated with cytokines alone (FIG. 4d);

FIG. 4a shows the numbers of positively engrafted mice per total number of transplanted cells, for each of the doses of transplanted cells ($5.0 \times 10^4$; $2.5 \times 10^4$; and $1.25 \times 10^4$ cells). FIGS. 4b and 4c show the percentage of total human (CD45+) (FIG. 4b) cells and human progenitor (CD45+CD34+) (FIG. 4c) cells in the bone marrow of mice transplanted with cells derived from culture initiated with $1.25 \times 10^4$ CD34+ cells. Note the enhanced engraftment of both total human, and human progenitor cells resulting from nicotinamide treatment.

DESCRIPTION OF THE PREFERRED EMBODIMENTS

Figure 1A:
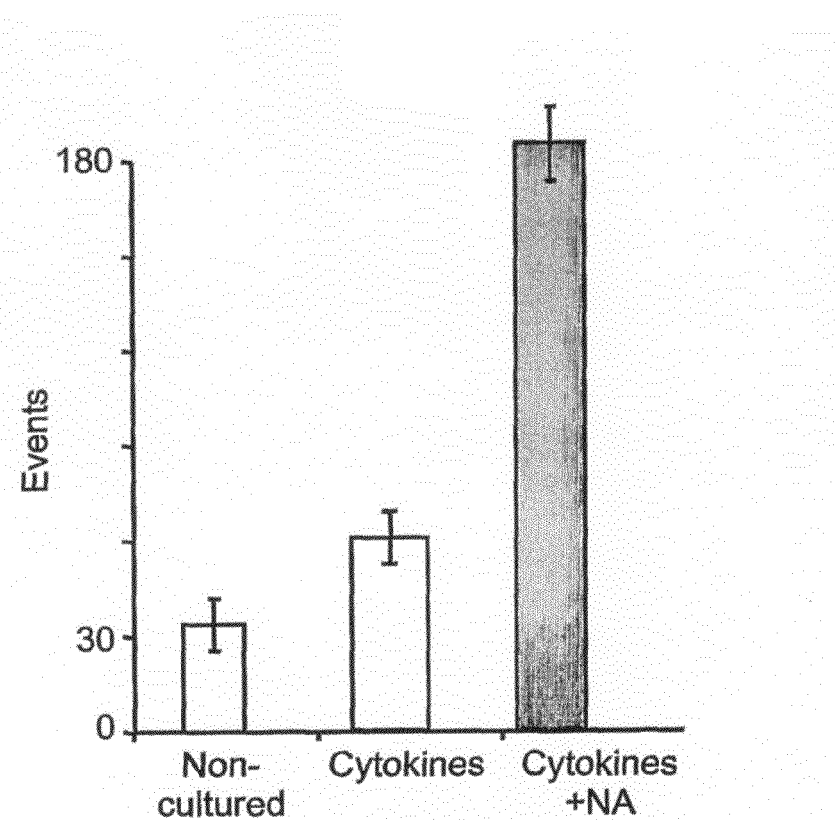
FIGS. 1a-1i are a graphic representation of flow cytometry analysis of the effect of nicotinamide on homing of hematopoietic stem cells into bone marrow of NOD/SCID mice. Non-cultured mononuclear cells or their entire progeny following 3-week expansion with cytokines and nicotinamide (cytokines+NA), or cytokines alone (cytokines) were labeled with CFSE and infused into sublethally irradiated NOD/SCID mice ($10 \times 10^6$ cells/mouse for the non-cultured group containing $5 \times 10^4$ CD34+ cells and the total progeny of $5 \times 10^4$ CD34+ cells following 3-week expansion with or without nicotinamide; $20 \times 10^6$ cells/mouse containing $180 \times 10^4$ CD34+ cells).

The present invention is of methods of improving homing and engraftment of transplantable cells.

The principles and operation of the present invention may be better understood with reference to the accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Successful blood and marrow transplantations, both autologous and allogenic, require the infusion of a sufficient number of hematopoietic stem cells capable of homing to the marrow cavity and regenerating a full array of hematopoietic cell lineages in a timely fashion. Recruitment of stem cells from the marrow into the blood is termed mobilization, or, more commonly stem cell mobilization. It is well established that enhancement of stem cell mobilization and/or homing will result in successful stem cell transplantation.

SDF-α chemoattracts hematopoietic stem and progenitor cells (HSCs/HPCs) and is thought to play a crucial role in the mobilization of HSCs/HPCs from the bone marrow as well as in stem cell homing.

CD26 is a widely distributed 110 kDa cell-surface glycoprotein with known dipeptidyl peptidase IV (DPPIV) activity in its extracellular domain capable of cleaving N-terminal dipeptides from polypeptides with either proline or alanine residues in the penultimate position. CD26 inhibits SDF activity by cleaving the latter at its position-2 proline, thereby inhibiting its stem cell mobilizing/homing functions.

U.S. Pat. Appl. 2004/0247574 teaches the use of CD26 inhibitors for improving engraftment efficiency of stem cell transplants by both improving stem cell homing to bone marrow and by increasing the number of mobilized donor stem cells. It does not teach down-regulation of CD26 surface expression but rather down regulation of CD26 catalytic activity. Specifically, U.S. Pat. Appl. 2004/0247574 does not teach the use of nicotinamide for down-regulating CD26 surface expression.

While reducing the present invention to practice, the present inventor uncovered that nicotinamide can be successfully used to down-regulate cell-surface expression of CD26, enhance the expression and function of adhesion and integrin molecules, increase induced transplantable cell migration, and significantly improve homing and engraftment of transplantable cells in-vivo.

As is demonstrated hereinbelow and in the Examples section which follows, the present inventor showed that short-term incubation of cells with nicotinamide is sufficient to down-regulate CD26 expression. A significant reduction in CD26-expressing CD34+ and AC133+ cells was observed following as few as 20 hours of incubation with nicotinamide.

Of greater significance, nicotinamide was shown effective in enhancing the functionality of molecules critical to the process of cell binding and arrest. Indeed, evaluation of cell migration potential in-vitro following nicotinamide exposure showed that nicotinamide both enhanced CXCL12-inducible migration and VLA-4-mediated binding and retention on VCAM-1 in transplantable cells cultured with nicotinamide (see Example 3 below). Since the processes of cell migration are mediated by "recognition" pairs such as VLA-4 and VCAM-1 in a wide variety of cells, this surprising finding indicates that nicotinamide, and nicotinamide derivatives and analogs, can be effective in enhancing binding and retention, critical to the ability of transplanted cells to successfully home, engraft and repopulate host tissues, for cells of diverse origins and stages of differentiation.

Actual in-vivo transplantation experiments with nicotinamide-treated cells provided conclusive evidence for the effect of nicotinamide on cell engraftment and homing potential. Example 2 below shows that exposure of mononuclear cells to nicotinamide prior to transplantation into NOD/SCID mice increased the homing to bone marrow sixfold over identical cells cultured without nicotinamide. Yet further, Example 4 below shows that at clearly sub-optimal doses of cells, while control cultured cells failed to cause repopulation of bone marrow in NOD/SCID mice, transplantation of nicotinamide-treated cells resulted in a high degree of engraftment and successful repopulation.

Taken together these results suggest a novel role for nicotinamide in cell homing and engraftment and as such in cell transplantation.

Thus, according to one aspect of the present invention there is provided a method of enhancing cell homing and engraftment potential, the method comprising ex-vivo or in vitro subjecting a population of cells to an amount of nicotinamide for a period of time sufficient for enhancing cell homing and engraftment potential.

As used herein the phrase "enhancing cell engraftment potential" refers to an improvement in efficiency, quality or rapidity of cell transplantation which may result from improved homing to the target tissue, improved adhesion, reduced rejection and the like. Methods for assessing cell engraftment potential include, for example, cell migration and other in vitro techniques, and histological, immunological and/or radiological assessment of tissues and organs from actual in-vivo transplantation, as described in detail hereinbelow. A self renewal potential of the stem cells can be determined in-vitro by long term colony formation (LTC-CFUc), or by in-vivo engraftment in the SCID-Hu mouse model. The SCID-Hu mouse model employs C.B-17 scid/scid (SCID) mice transplanted with human fetal thymus and liver tissue or fetal BM tissue and provides an appropriate model for the evaluation of putative human hematopoietic stem cells. Because of the reconstitution of the SCID mice with human fetal tissue, the model affords the proliferation of stem cells, in this case human hematopoietic stem cells to proliferate, and function in the hematopoietic microenvironment of human origin. Mice are typically irradiated, then delivered stem cells into the grafts, and reconstitution is measured by any number of methods, including FACS and immunohistochemistry of repopulated organs (Humeau L., et al Blood (1997) 90:3496; also see Materials and Experimental Methods below).

As used herein the term "ex-vivo" refers to a process in which cells are removed from a living organism and are propagated outside the organism (e.g., in a test tube).

As used herein, the term "in-vitro" refers to a process in which cells originating from a cell line or lines (such as NTera2 neural cells, embryonic cell lines, etc.) maintained in the laboratory, are manipulated outside of an organism. Such cell lines are often immortalized cells.

As used herein the phrase "population of cells" refers to a homogeneous or heterogeneous isolated population of cells which comprise cell populations suitable for transplantation. In a preferred embodiment, at least a portion of the population of cells of this aspect of the present invention expresses CD26 or VLA-4 on the cell-surface.

As used herein, the phrase "stem cells" refers both to the earliest renewable cell population responsible for generating cell mass in a tissue or body and the very early progenitor cells, which are somewhat more differentiated, yet are not committed and can readily revert to become a part of the earliest renewable cell population.

As used herein, the phrases "non-stem", "non-progenitor" and "committed cells" refer to cells at various stages of differentiation, which generally no longer retain the ability to revert to become a part of a renewable cell population. Methods of ex-vivo culturing stem, progenitor, and non-stem, non-progenitor committed cells are well known in the art of cell culturing. To this effect, see for example, the text book "Culture of Animal Cells—A Manual of Basic Technique" by Freshney, Wiley-Liss, N.Y. (1994), Third Edition, the teachings of which are hereby incorporated by reference.

The population of cells of the present invention may be from an autologous or non-autologous donor (allogeneic or xenogeneic).

In a preferred embodiment, the cells for transplantation are stem and/or progenitor cells, and the source of the stem cell population is an unfractionated mononuclear cell preparation, not having been enriched for CD34+ or other hematopoietic stem cells. In another embodiment, the stem cells are identified by stem cell markers such as CD34+, CD34+/CD38−, CD133+, CD34+/Lin−, and other stem cell markers known in the art. In yet another embodiment, the source of the stem cell population are stem cells having been enriched for hematopoietic stem cells by selection according to stem cell markers.

For example, stem cells of the present invention may be derived from a source selected from the group consisting of hematopoietic cells, umbilical cord blood cells, and mobilized peripheral blood cells.

As used herein "nicotinamide" refers to nicotinamide as well as to products that are derived from nicotinamide, analogs thereof and metabolites of nicotinamide or nicotinamide analogs, such as, for example, NAD, NADH and NADPH.

As used herein, the phrase "nicotinamide analog" refers to any molecule that is known to act similarly to nicotinamide. Representative examples of nicotinamide analogs include, without limitation, benzamide, nicotinethioamide (the thiol analog of nicotinamide), nicotinic acid and α-amino-3-indolepropionic acid.

As used herein the term "subject" refers to a mammalian subject, preferably a human subject.

The phrase "a nicotinamide or a nicotinamide analog derivative" refers to any structural derivative of nicotinamide itself or of an analog of nicotinamide. Examples of such derivatives include, without limitation, substituted benzamides, substituted nicotinamides and nicotinethioamides and N-substituted nicotinamides and nicotinthioamides.

Additionally or alternatively, stem cell mobilization may be effected prior to harvest of cells for stem cell transplantation using mobilizing agents which are well known in the art. Generally, the mobilization process is initiated by stress-induced activation of neutrophils and osteoclasts by chemotherapy and repeated stimulation with cytokines such as granulocyte colony-stimulating factor (G-CSF), resulting in shedding and release of membrane-bound stem cell factor (SCF), proliferation of progenitor cells, as well as activation and/or degradation of adhesion molecules. Mobilizing agents which may be used in accordance with the present invention include, but are not limited to, DNA damaging agents, single chemotherapeutic agents (e.g., cyclophosphamide), combined chemotherapy regimens [e.g., iphosphamide, carboplatin and etoposide (ICE) and methylprednisolone, ara-c, and cisplatin (ESHAP)], cytokines such as G-CSF, GM-CSF, SCF, FLT-3 ligand, and chemokines such as IL-8, MIP-1α, Groβ, and SDF-1. The mode of administration, as well as the time frame needed to achieve mobilization and the types of cells mobilized depend on the molecules used. For example, G-CSF is usually administered daily as a dose of 5-10 μg/gk for 5-10 days, alone or after therapy. The adjustment of the mobilization regimen is done by the physician and reviewed in Cottker-Fox et al. (2003) Hematology 419-437.

Methods of preparation of cells for transplantation are well known in the art. For preparation of non-stem cells, cells can be obtained from donor tissue by dissociation of individual cells from the connecting extracellular matrix of the tissue. Tissue from a particular region is removed using a sterile procedure, and the cells are dissociated-using any method known in the art including treatment with enzymes such as trypsin, collagenase, DNAse and the like, or by using physical methods of dissociation such as with a blunt instrument.

Cells prepared for transplantation can be maintained in a physiological solution, or cultured in suspension or on a fixed substrate. Suitable culture media capable of supporting cells include HEM, DMEM, RPMI, F-12, and the like. If required, the medium can contain supplements required for cellular metabolism such as glutamine and other amino acids, vitamins, minerals and useful proteins such as transferrin, and the like. The medium may also contain antibiotics to prevent contamination with yeast, bacteria, and fungi, such as penicillin, streptomycin, gentamicin, and the like. If cells are to be cultured, conditions should be close to physiological conditions (preferably, a pH of about 6 to about 8, and a temperature of about 30° C. to about 40° C.). The culture medium can be optionally supplemented with at least one proliferation-inducing growth factor, such as EGF, amphiregulin, acidic fibroblast growth factor (aFGF or FGF-1), basic fibroblast growth factor (bFGF or FGF-2), transforming growth factor alpha (TGF-alpha), cytokines such as G-CSF, GM-CSF, SCF, FLT-3 ligand, and/or chemokines such as IL-8, MIP-1α, Groβ, and SDF-1, and combinations thereof. In addition to proliferation-inducing growth factors, other growth factors may be added to the culture medium, including NGF, platelet-derived growth factor (PDGF), thyrotropin releasing hormone (TRH), and the like.

Selection and enrichment of specific cell types can be performed, such as separation of hepatocytes from liver tissue, separation of neurons from glial cells, or isolation of islet cells from pancreatic tissue, by morphological, physical, immunohistochemical (FACS) or other means. Fresh or cultured cell preparations can be cryopreserved until they are needed by any method known in the art. The cells can be suspended in an isotonic solution, preferably a cell culture medium, containing a particular cryopreservant. Such cryopreservants include dimethyl sulfoxide (DMSO), glycerol, and the like. Further methods for preparation and storage of cells for transplantation are known in the art, and disclosed in detail in, for example, the Handbook of Transplantation (Kipshidze and Serruys, eds. London, UK, 2004).

Methods of preparation of stem cells are well known in the art, commonly selecting cells expressing one or more stem cell markers such as CD34, CD133, etc, or lacking markers of differentiated cells. Selection is usually by FACS, or immunomagnetic separation, but can also be by nucleic acid methods such as PCR (see Materials and Experimental Methods hereinbelow). Embryonic stem cells and methods of their retrieval are well known in the art and are described, for example, in Trounson A O (Reprod Fertil Dev (2001) 13: 523), Roach M L (Methods Mol Biol (2002) 185: 1), and Smith A G (Annu Rev Cell Dev Biol (2001) 17:435). Adult stem cells are stem cells, which are derived from tissues of adults and are also well known in the art. Methods of isolating or enriching for adult stem cells are described in, for example, Miraglia, S. et al. (1997) Blood 90: 5013, Uchida, N. et al. (2000) Proc. Natl. Acad. Sci. USA 97: 14720, Simmons, P. J. et al. (1991) Blood 78: 55, Prockop D J (Cytotherapy (2001) 3: 393), Bohmer R M (Fetal Diagn Ther (2002) 17: 83) and Rowley S D et al. (Bone Marrow Transplant (1998) 21: 1253), Stem Cell Biology Daniel R. Marshak (Editor) Richard L. Gardner (Editor), Publisher: Cold Spring Harbor Laboratory Press, (2001) and Hematopoietic Stem Cell Transplantation. Anthony D. Ho (Editor) Richard Champlin (Editor), Publisher: Marcel Dekker (2000).

It will be appreciated that nicotinamide can enhance engraftment and homing potential in a wide variety of cell types. For example, nicotinamide can down-regulate surface expression of CD26, and enhance functionality of VLA-4, CXCR-2 or other adhesion molecules from any cell-type expressing same and since these molecules are widely expressed in cell populations of diverse origin, the population of cells of this aspect of the present invention may comprise unselected cell populations, such as crude cell preparations from tissue, or mononuclear stem and/or progenitor cells, as well as more homogenous populations of selected cell types.

As used herein, the phrase "hematopoietic mononuclear cells" refers to the entire repertoire of white blood cells present in a blood sample, usually hematopoietic mononuclear cells which comprise a major fraction of hematopoietic committed cells and a minor fraction of hematopoietic stem and progenitor cells. In a healthy human being, the white blood cells comprise a mixture of hematopoietic lineages committed and differentiated cells (typically over 99% of the mononuclear cells are lineages committed cells) including, for example: Lineage committed progenitor cells $CD34^+$ $CD33^+$ (myeloid committed cells), $CD34^+CD3^+$ (lymphoid committed cells) $CD34^+CD41^+$ (megakaryocytic committed cells) and differentiated cells—$CD34^-$ $CD33^+$ (myeloids, such as granulocytes and monocytes), $CD34^-CD3^+$, $CD34^-CD19+$ (T and B cells, respectively), $CD34^-CD41^+$ (megakaryocytes), and hematopoietic stem and early progenitor cells such as $CD34^+$Lineage negative ($Lin^-$), CD34-Lineage negative $CD34^+CD38^-$ (typically less than 1%).

Hematopoietic mononuclear cells are typically obtained from a blood sample by applying the blood sample onto a Ficoll-Hypaque layer and collecting, following density-cushion centrifugation, the interface layer present between the Ficoll-Hypaque and the blood serum, which interface layer essentially entirely consists of the white blood cells present in the blood sample.

Presently, hematopoietic stem cells can be obtained by further enrichment of the hematopoietic mononuclear cells obtained by differential density centrifugation as described above. This further enrichment process is typically performed by immuno-separation such as immunomagnetic-separation or FACS and results in a cell fraction that is enriched for hematopoietic stem cells (for detailed description of enrichment of hematopoietic stem cells, see Materials and Experimental Procedures in the Examples section hereinbelow).

Regardless of the origin of cells employed and their composition, once the cells are obtained, they are subjected to (contacted with) an amount of nicotinamide for a period of time sufficient to enhance engraftment and homing of the cells following transplantation. Such a period of time may be brief, or lengthier, as required. In one preferred embodiment, the contacting is for a period of time sufficient to down-regulate CD26 surface expression. In another preferred embodiment, the cells are hematopoietic stem cells, and the contacting is for a period of time insufficient for stem cell proliferation (also referred to as expansion) while sufficient to down-regulate CD26 surface expression. In yet another embodiment, the contacting is for a period of time sufficient to increase functionality of VLA-4, CXCR2 and other adhesion and/or integrin molecules.

Methods of determining protein cell-surface expression are well known in the art. Examples include immunological methods, such as, FACS analysis (see Examples section) as well as biochemical methods (cell-surface labeling, e.g., radioactive, fluorescence, avidin-biotin).

Methods of assaying cell-proliferation are well known in the art (such as MTT, thymidine incorporation, FACS). It will be appreciated that cell doubling rate may also be derived from the literature.

Depending on the cell type, and the intended use thereof, cells may be ex-vivo subjected to nicotinamide for long-term contact, i.e. periods of weeks or more, and cells may even be stored in contact with nicotinamide prior to use for transplantation. Further, according to certain embodiments, short-term exposure is desirable. Long-term contacting can be for between 1 and 18 weeks, preferably between 3 and 9 weeks, more preferably between 2 and 5 weeks, most preferably between 2 and 3 weeks. Short term contacting can be for 1 to 2 weeks, preferably one week or less, more preferably between 1-5 days.

While reducing the present invention to practice, it was uncovered that 20 hours exposure of hematopoietic stem cells to nicotinamide was sufficient to effect a reduction in CD26 expression, crucial to cell homing and engraftment, although insufficient to allow for stem cell expansion or proliferation to take place. Thus, according to one embodiment of the present invention, cells are ex-vivo subjected to nicotinamide for a period of time not exceeding a few days, preferably 30 hours, more preferably 1-30 hours, even more preferably 5-30 hours, even more preferably 10-30 hours. In another preferred embodiment, the cells are stem and/or progenitor cells, and the duration of exposure to nicotinamide is selected insufficient for stem cell expansion, or under conditions insufficient for stem cell expansion, such as absence of cytokines, absence of nutrients, sub-optimal temperature, etc.

Nicotinamide is preferably provided in a final concentration of 0.01-60 mg/ml, preferably 1-40 mg/ml, more preferably 5-30 mg/ml, and most preferably 10-20 mg/ml. The selection of culture medium and medium supplements, depends on the cells and their intended use.

In one preferred embodiment cells subjected to nicotinamide can be used for transplantation to a subject in need thereof following nicotinamide exposure for the predetermined period of time, without further ex-vivo expansion. It will be appreciated that exposure to nicotinamide can be performed on cells that have received additional ex-vivo treatment, such as expansion, selection, genetic modification, etc. well known in the art, including prior ex-vivo exposure to nicotinamide, and preferably closely preceding the use thereof for engraftment.

Following exposure to nicotinamide, the cells may then be transplanted in (administered to) a subject in need thereof. The following summarizes some clinical applications which may be addressed according to the teachings of the present invention.

Hematopoietic cell transplantation: Transplantation of hematopoietic cells has become the treatment of choice for a variety of inherited or malignant diseases. While early transplantation procedures utilized the entire bone marrow (BM) population, recently, more defined populations, enriched for stem cells ($CD34^+$ cells) have been used [Van Epps Blood Cells 20:411, (1994)]. In addition to the marrow, such cells could be derived from other sources such as peripheral blood (PB) and neonatal umbilical cord blood (CB) [Emerson Blood 87:3082 (1996)]. Compared to BM, transplantation with PB cells shortens the period of pancytopenia and reduces the risks of infection and bleeding [Brugger N Engl J Med 333:283, 1995; Williams Blood 87:1687, (1996); Zimmerman J Heamatotherapy 5:247, (1996)].

An additional advantage of using PB for transplantation is its accessibility. The limiting factor for PB transplantation is the low number of circulating pluripotent stem/progenitor cells.

To obtain enough PB-derived stem cells for transplantation, these cells are "harvested" by repeated leukophoresis following their mobilization from the marrow into the circulation by treatment with chemotherapy and cytokines [Brugger N Engl J Med 333:283, 1995; Williams Blood 87:1687, (1996)]. Such treatment is obviously not suitable for normal donors.

The use of ex-vivo expanded stem cells for transplantation has the following advantages [Koller Blood 82:378, (1993); Lebkowski Blood Cells 20:404, (1994)]:

It reduces the volume of blood required for reconstitution of an adult hematopoietic system and may obviate the need for mobilization and leukophoresis [Brugger N Engl J Med 333:283, 1995].

It enables storage of small number of PB or CB stem cells for potential future use.

In the case of autologous transplantation of recipients with malignancies, contaminating tumor cells in autologous infusion often contribute to the recurrence of the disease [Brugger N Engl J Med 333:283, 1995]. Selecting and expanding $CD34^+$ stem cells will reduce the load of tumor cells in the final transplant.

The cultures provide a significant depletion of T lymphocytes, which may be useful in the allogeneic transplant setting for reducing graft-versus-host disease.

Clinical studies indicate that transplantation of ex-vivo expanded cells derived from a small number of PB $CD34^+$ cells can restore hematopoiesis in recipients treated with high doses of chemotherapy, although the results do not yet allow firm conclusions about long term in-vivo hematopoietic capabilities of these cultured cells [Brugger N Engl J Med 333: 283, 1995; Williams Blood 87:1687, (1996)].

For successful transplantation, shortening of the duration of the cytopenic phase, as well as long-term engraftment, is crucial. Inclusion of intermediate and late progenitor cells in the transplant could accelerate the production of donor-derived mature cells thereby shortening the cytopenic phase. It is important, therefore, that ex-vivo expanded cells include, in addition to stem and/or progenitor cells subjected to nicotinamide as described hereinabove, more differentiated cells in order to optimize short-term recovery and long-term restoration of hematopoiesis. Inclusion of expanded intermediate and late committed cells, especially those committed to the neutrophilic and megakaryocytic lineages, concomitant with the expanded stem and/or progenitor cells, should serve this purpose [Sandstrom Blood 86:958, (1995)].

Such cultures may be useful in restoring hematopoiesis in recipients with completely ablated bone marrow, as well as in providing a supportive measure for shortening recipient bone marrow recovery following conventional radio- or chemo-therapies.

Tissue regeneration: Stem cell populations of the present invention, can be used for the promotion of tissue regeneration. Transplantation of stem cells, has great promise for benefits in regenerative medicine, reconstructive surgery, tissue engineering, regenerating new tissues and naturally healing diseased or injured organs (for review see Czyz et al, Biol Chem, 2003; 384:1391-40, Sylvester et al Arch Surg 2004; 139:93-99). Further, neurons and supporting glial cells have been used for transplantation in treatment of Huntington's disease (U.S. Pat. No. 6,524,865 to Freed et al) and pancreatic islet cells are being used for transplantation for type I and type II diabetes (see, for example, U.S. Pat. No. 6,326,201, to Fung et al; and U.S. Pat. No. 7,045,349 to Benedict et al). Muscle, and muscle derived cells, are being investigated for clinical use, and have shown, promising results when transplanted into injured heart tissue, bone tissue and articular structures (see U.S. Pat. No. 6,866,842 to Chancellor, et al). Thus, according to one aspect of the instant invention, the cells for engraftment or transplantation can be derived from an organ selected from the group consisting of a muscle, skin, a bone, a lymph organ, a pancreas, a liver, a gallbladder, a kidney, a digestive tract organ, a respiratory tract organ, a reproductive organ, a urinary tract organ, a blood-associated organ, a thymus, a spleen and a nervous system organ. Examples of cells which can be prepared for implantation by the methods of the present invention include primary cultures as well as established cell lines. Examples of these include, but are not limited to pancreatic islet cells, human foreskin fibroblasts, beta cell insulomas, NT2 cells, embryonic cells, embryonic stem cells, hepatocytes, dopamine secreting ventral mesencephalon cells, neuroblastoid cells, adrenal medulla cells, T-cells combinations of these, and the like. As can be seen from this partial list, cells of all types, including dermal, neural, blood, organ, muscle, glandular, bone, digestive, reproductive and immune system cells, as well as cells of all species of origin, can be prepared successfully by this method.

Recent reports have demonstrated the capability of transplanted or transfused stem cells to enhance regeneration in non-homologous tissue, other than that which the stem cells were derived. For example, enhanced myogenesis and angiogenesis in infarcted myocardium have been observed following infusion of bone marrow stem cells (Tse et al, Lancet 2003, 361:47-79, Jackson et al J Clin Invest 2001; 107:1395-402, Orlic et al Nature 2001; 410:701-5; Lee et al, Cell Cycle 2005; 4:861-64, Nagaya et al Am J Heart Circ Phys 2004; 287:H2670-76). Other studies have shown bone marrow, endothelial and skeletal muscle stem cells to be beneficial in ischemic renal injury (Togel et al, AJP Renal Phys 2005; 289:F31-F42 and Arriero, et al, AMJ Ren Phys 2004; 287: F621-27).

Gene therapy: For successful long-term gene therapy, a high frequency of genetically modified cells with transgenes stably integrated within their genome, is an obligatory requirement. In BM tissue, for example, while the majority of cells are cycling progenitors and precursors, stem cells constitute only a small fraction of the cell population and most of them are in a quiescent, non-cycling state. Viral-based (e.g., retroviral) vectors require active cell division for integration of the transgene into the host genome. Therefore, gene transfer into fresh stem cells is highly inefficient. The ability to store and process a selected population of cells ex-vivo, and enhance their homing and engraftment potential would provide for an increased probability of the successful use of genetically modified cell transplantation [Palmiter Proc Natl Acad Sci USA 91(4): 1219-1223, (1994)].

Adoptive immunotherapy: Ex-vivo-expanded, defined lymphoid subpopulations have been studied and used for adoptive immunotherapy of various malignancies, immunodeficiencies, viral and genetic diseases [Freedman Nature Medicine 2: 46, (1996); Heslop Nature Medicine 2: 551, (1996); Protti Cancer Res 56: 1210, (1996)].

The treatment enhances the required immune response or replaces deficient functions. This approach was pioneered clinically by Rosenberg et al. [Rosenberg J Natl Cancer Inst. 85: 622, 1993] using a large number of autologous and also allogeneic ex-vivo expanded non-specific killer T cells, and subsequently ex-vivo expanded specific tumor infiltrating lymphocytes.

Functionally active, antigen-presenting cells could be grown from a starting population of $CD34^+$ PB cells in cytokine-supported cultures, as well. These cells can present soluble protein antigens to autologous T cells in-vitro and, thus, offer new prospects for the immunotherapy of minimal residual disease after high dose chemotherapy. Ex-vivo expansion of antigen-presenting dendritic cells has been studied as well, and is an additional promising application of the currently proposed technology [Bernhard Cancer Res 10: 99, (1995); Fisch Eur J Immunol 26: 595, (1996); Siena Expt Hematol 23:1463, (1996)].

Additional Examples for Ex-Vivo Applications:

Additional applications of non-stem, differentiated cells, as well as stem and progenitor cell treatment with nicotinamide include skin regeneration, hepatic regeneration, muscle regeneration, stimulation of bone growth for applications in osteoporosis and transplantation of chondrocytes/chondroblasts and/or synovial cells for treatment of articular and arthritic disorders.

According to one aspect of the present invention, the ex-vivo contacting of cell populations with nicotinamide, according to the features described hereinabove, can be utilized for preparing a population of stem or non-stem cells ex-vivo or in-vitro for implanting the cells in an organ of a subject in need thereof.

Cells of the present invention may be transplanted by means of direct injection into an organ, injection into the bloodstream, intraperitoneal injection, etc. Suitable methods of transplantation can be determined by monitoring the homing and engraftment of the implanted cells to the desired organ, the expression of desired organ-specific genes or markers, and the function of the derived organ of the subject. In the pancreas, for example, maintenance of euglycemia, secretion of insulin and/or C peptide can be a measure of the restoration of function to a diabetic host animal following cell replacement therapy as disclosed hereinbelow. In the liver, for example, albumin synthesis can be monitored.

Cell populations of the present invention can be provided per se, along with the culture medium containing same, isolated from the culture medium, and combined with a pharmaceutically acceptable carrier as well as with additional agents which may promote cell engraftment and/or organ function (e.g., immunosuppressing agents, antibiotics, growth factor). Hence, cell populations of the invention can be administered in a pharmaceutically acceptable carrier or diluent, such as sterile saline and aqueous buffer solutions. The use of such carriers and diluents is well known in the art.

Compositions of the present invention may, if desired, be presented in a pack or dispenser device, such as an FDA-approved kit, which may contain one or more unit dosage forms containing the active ingredient (e.g., cells). The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

The cells prepared according to the methods of the present invention can be administered to the subject per se, or in a pharmaceutical composition where it is mixed with suitable carriers or excipients.

As used herein, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier," which may be used interchangeably, refer to a carrier or a diluent that does not cause significant irritation to an organism and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Suitable routes of administration may, for example, include oral, rectal, transmucosal, especially transnasal, intestinal, or parenteral delivery, including intramuscular, subcutaneous, and intramedullary injections, as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., a nucleic acid construct) effective to prevent, alleviate, or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition. (See, e.g., Fingl, E. et al. (1975), "The Pharmacological Basis of Therapeutics," Ch. 1, p. 1.)

Depending on the severity and responsiveness of the condition to be treated, dosing can be of a single or a plurality of administrations, with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Procedures

Cord Blood Samples—

Cells were obtained from umbilical cord blood after normal full-term delivery (informed consent was given). Samples were collected and frozen according to Rubinstein et al. [Rubinstein et al. Proc Natl Acad Sci USA. 1995; 92 (22):10119-10122.] within 24 h postpartum. Prior to use, the cells were thawed in Dextran buffer (Sigma, St. Louis, Mo., USA) containing 2.5% human serum albumin (HAS, Bayer Corp. Elkhart, Ind., USA), layered on a Ficoll-Hypaque gradient (1.077 g/mL; Sigma), and centrifuged at 800×g for 30 min. The mononuclear cells in the interface layer were collected and washed three times in phosphate-buffered saline (PBS, Biological Industries) containing 0.5% HSA. To purify the CD34+ cells, the mononuclear cell fraction was subjected to two cycles of immunomagnetic bead separation, using a "MiniMACS CD34 progenitor cell isolation kit" (Miltenyi Biotec Bergisch, Gladbach, Germany), according to manufacturer's instructions. The purity of the CD34+ population thus obtained was 95-98%, as evaluated by flow cytometry.

FACS Analysis of CD34+ Cells—

Percentages of progenitor cells positive for CD26 were determined by staining of CD34+ cells with anti-CD26 FITC purchased from Becton Dickinson.

Ex Vivo Expansion—

Purified CD34+ cells were cultured in culture bags (American Fluoroseal Co., Gaithersburg, Md.) at $1 \times 10^4$ cells/ml in MEMα medium, 10% fetal calf serum (FCS) and cytokines: Thrombopoietin (TPO), interleukin-6 (IL-6), FLT-3 ligand and stem cell factor (SCF), each at a final concentration of 50 ng/ml (Perpo Tech, Inc., Rocky Hill, N.J.), with or without 5 mM nicotinamide (NA) (Sigma Aldrich, Milwaukee, Wis.) and incubated at 37° C. in a humidified atmosphere of 5% $CO_2$ in air. Preliminary studies conducted with various concentrations of NA (1-10 mM), indicated that in combination with the 4 cytokines, 5 mM was the optimal NA concentration (data not shown). Until week 3, the cultures were topped weekly with the same volume of fresh medium and then weekly demi-depopulated. Cell counting, colony forming unit (CFUc) assay and immunophenotype analysis were performed as described hereinbelow.

Immunophenotyping of CD34+ Cells—

MiniMACS re-isolated CD34+ cells were washed with PBS solution containing 1% BSA and double stained (at 4° C. for 30 min) with PE-conjugated anti-CD34 and FITC-conjugated antibodies to CXCR4, VLA-4 (Chemicon Intnl, Inc. Temecula, Calif., USA), LFA-1 (IQ product), CD38, or with a mixture of FITC-conjugated antibodies against differentiation antigens (CD38, CD33, CD14, CD15, CD3, CD61, CD19) for determination of CD34+Lin− cells. (Antibodies to CD34, CD38 and CD61 were purchased from DAKO Glostrup, Corp, Carpenteria, Calif., USA, while the others were from Becton Dickinson and Co, San Jose, Calif., USA). The cells were then washed in the above buffer and analyzed, using a FACScalibur® flow cytometer (Becton Dickinson and Co, San Jose, Calif.). Emission of $10^4$ cells was measured using logarithmic amplification, and analyzed using CellQuest software (Becton Dickinson and Co, San Jose, Calif., USA). The FACS analysis results are presented as percentages of CD34+ cells. The absolute number of CD34+ CD38− and CD34+Lin− cells was calculated from the total number of CD34+ cells in culture.

CFSE Labeling—

Non-cultured or cultured cells were washed and resuspended at less than $10^7$ cells/mL in serum-free medium. CFSE (Molecular Probes, Inc., Eugene, Oreg., USA) was added at a final concentration of 5 μg/ml, and the cells were incubated for 10 minutes at 37° C. Uptake of the dye was stopped by the addition of 10% FCS. After labeling, cells were washed three times in PBS supplemented with 10% FCS and analyzed by flow cytometry for fluorescence intensity, then injected intravenously into sublethally irradiated NOD/SCID mice (10-20 million cells per mouse).

In Vitro Migration Assay—

RPMI plus 10% FCS (0.6 ml) containing 100 ng/ml CXCL12 (R&D Systems) was put into the lower chamber of a Costar 24-well "transwell" culture plate (Corning, Inc, Corning, N.Y.). Cells ($2 \times 10^5$) in 100-μl medium were introduced into the upper chamber, over a porous membrane (pore size, 5 μm). After 4 hours, cells were collected from both chambers and counted by flow cytometry (FACSsort, Becton Dickinson and Co, San Jose, Calif., USA). Spontaneous migration control migration was performed without CXCL12 in the lower chamber.

In Vivo Analysis of Homing—

NOD/SCID mice (8-10 week old) (Harlan Ltd., Israel) were sub-lethally irradiated (at 375cGy at 67cGy/min) and 24 hours later inoculated via the tail vein with either CFSE-labeled cultured, or non-cultured CB cells. Mice were sacrificed at 24 hours post injection and bone marrow samples were obtained by flushing their femurs and tibias with IMDM at 4° C. Homing of human cells was detected by flow cytometry via visualization of CFSE-stained cells over a background of unlabeled murine cells. The bright fluorescence of CFSE was sufficient to separate labeled human cells from unlabeled murine cells by at least 1 log. To quantify homing of human progenitor cells, bone marrow cells were stained with APC-conjugated antihuman CD34 monoclonal antibodies and CFSE$^+$CD34$^+$ (human progenitor) cells were enumerated. For each sample 100,000 events were recorded and analyzed.

Transplantation of Human CD34$^+$ Cells into NOD/SCID mice—

NOD/SCID mice were bred and maintained in sterile intra-ventilated cages (Techniplast, Bugugiatte, Italy). Eight-week-old mice were sub-lethally irradiated as described above. Mice were then inoculated via the tail vein with fresh purified CB-derived CD34$^+$ cells or their entire progeny following 3-weeks in culture. To avoid donor variability, CB-derived CD34$^+$ cells from several units were pooled and used for expansion cultures as well as group injection. Mice were sacrificed at week 4, and marrow samples were obtained by flushing their femurs and tibias with IMDM at 4° C. Flow cytometric analysis of NOD/SCID marrow cells was performed as described hereinabove, using monoclonal antibodies against human leukocyte differentiation antigens to identify human cell engraftment.

Quantification of SCID Repopulating Cells (SRCs)—

The frequencies of SRCs were quantified by a limiting dilution analysis and applying Poisson statistics to the single-hit model as described previously. Mice were scored as positively engrafted if 0.5% of their marrow cells expressed human CD45. The frequencies of SRCs and statistical comparison between individual populations were calculated by maximum likelihood estimator using L-Calc. Software (StemCell Technologies, Vancouver, BC).

Shear Flow Experiments—

Soluble purified seven-domain human VCAM-1, sVCAM-1 was mixed in coating medium (PBS buffered with 20 mM sodium bicarbonate pH, 8.5) with a fixed amount of carrier (2 μg/ml HSA) and adsorbed as 10-μl spots on polystyrene plates (Becton Dickinson and Co, San Jose, Calif., USA) for 2 hours at 37° C., alone or with the indicated amounts of intact or heat-inactivated chemokines. Plates were washed and blocked with HSA (20 mg/ml). VCAM-1 site densities were assessed using $^{125}$I-labeled anti-VCAM-1 mAb, 4B9. Cell monolayers of non-cultured cells and cells following culturing with or without nicotinamide and VCAM-1/chemokine-coated substrates were assembled as the to lower surface of the flow chamber (260-μm gap) and extensively washed with binding medium. The flow chamber was mounted on the stage of an inverted phase contrast microscope (Diaphot 300; Nikon Europe BV, Badhoevedorp, The Netherlands). All flow experiments were conducted at 37° C. Cells were perfused at 10$^6$ cells/ml through the chamber at desired flow rate generated with an automated syringe pump. The entire duration of cell perfusions were recorded on a videotape with a long integration LIS-700 CCD video camera (Applitech Rigicam, Israel) and a Time Lapse SVHS-Video recorder (AG-6730; Panasonic, Japan). All cellular interactions with the adhesive substrates were determined by manually tracking the motions of individual cells along 0.9-mm field paths for 1 min. Cellular interactions with VCAM-1-bearing surfaces were >95% α4 integrin dependent. In each experiment all events were normalized to a constant cell population flowing in immediate proximity with the substrate. Frequency of each category of tethers was expressed in percentage of units (event×cell$^{-1}$×10$^2$); 1% unit measured at 0.5, 1, and 1.5 dyn/cm$^2$ corresponded to tethering rate of 1.5×10$^{-1}$, 3×10$^{-3}$, and 4.5×10$^{-3}$ events×cell$^{-1}$ mm$^{-1}$ s$^{-1}$, respectively, expressed as the mean±range or SD.

Statistics—

The non-parametric Wilcoxon Rank Test was applied for testing differences between the study groups. All the tests applied were two-tailed, and a p value of ≤5% was considered statistically significant. The data were analyzed using SAS software (SAS Institute, Cary, N.C.).

Experimental Results

Example 1

Nicotinamide Down-Regulates CD26/dipeptidylpeptidase IV Expression on CD34+ Cells The effect of short-term incubation with nicotinamide on HSC CD26 membranal expression was addressed by FACS analysis.

Freshly purified CD34+ cells were FACS analyzed for the expression of CD26 (T-0) then incubated±Nicotinamide 5 mM for 20 hours (T-20 hours) and FACS analyzed again. As demonstrated in a duplicate experiment summarized in Table 1 below, following 20 hours incubation (T-20) in the presence of Nicotinamide, CD26 expression was significantly reduced by the presence of Nicotinamide (2-3 fold reduction) as compared to cells maintained for 20 hours in the absence of Nicotinamide as well as to freshly purified CD34+ cells (T-0).

TABLE 1

| | | CD26+ cells (%) | |
| --- | --- | --- | --- |
| | | T-20 | |
| | T-0 | Control | +Nicotinamide |
| Exp. 1 | 8.5 | 5 | 2.7 |
| Exp. 2 | 10 | 12 | 6 |

Example 2

Nicotinamide Increases Bone Marrow Homing of Cultured Cells

Reduced engraftment efficacy of cultured cells has been attributed, at least in part, to a defect in their homing ability relative to non-cultured cells (Szilvassy, S. J., et al, Blood, 2000; 95:2829-37). To evaluate the effect of nicotinamide on the homing of cultured cells, NOD/SCID mice were transplanted with either 10×10$^6$ non-cultured mononuclear cells (MNC), containing 5×10$^4$ CD34+ cells (0.5% CD34+ cells), or with their total progeny following 3-weeks in culture with cytokines, with or without nicotinamide, each transplantation containing 180×10$^4$ CD34+ cells. Prior to transplantation, the cells were labeled with CFSE. Twenty-four hours post transplantation total CFSE-labeled cells and CFSE labeled CD34+ cells that homed to the mouse bone marrow of the recipient mice were quantified by FACS.

Figure 1B:
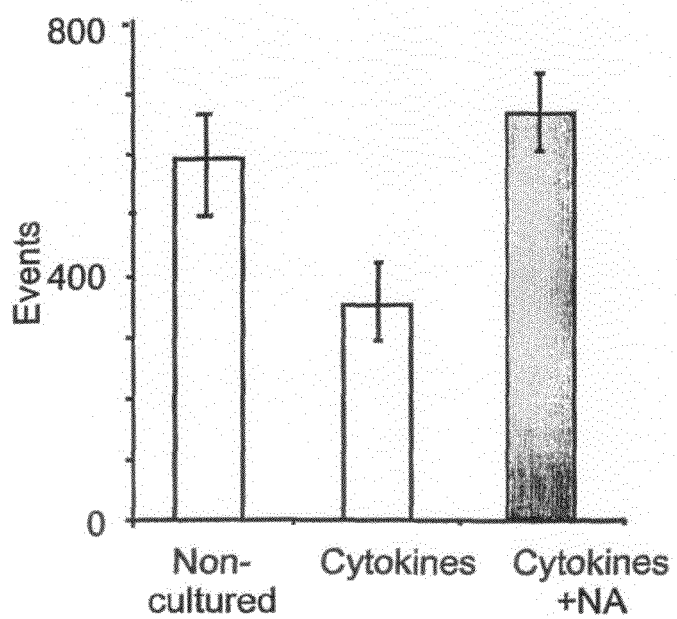
Figure 1C:
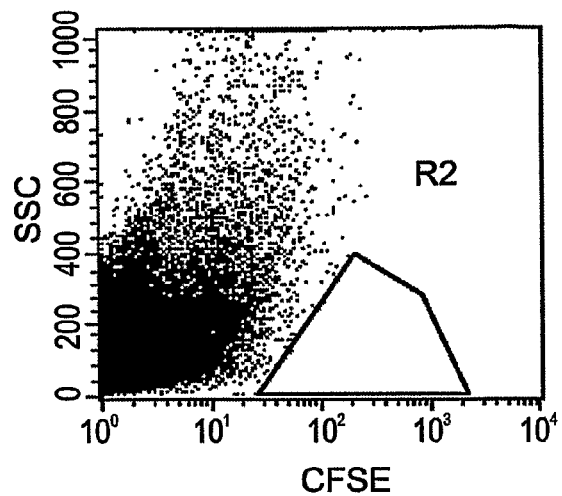
Figure 1D:
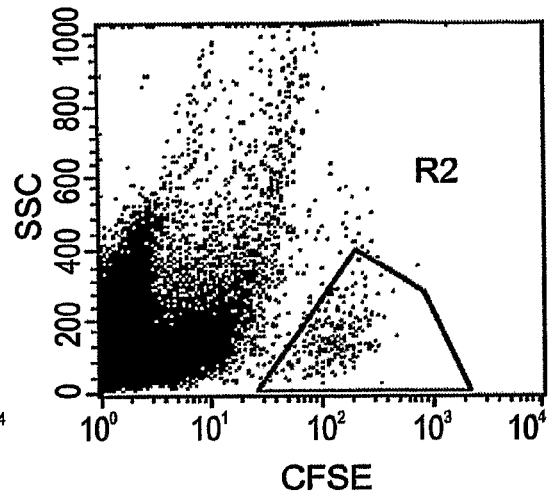
Figure 1E:
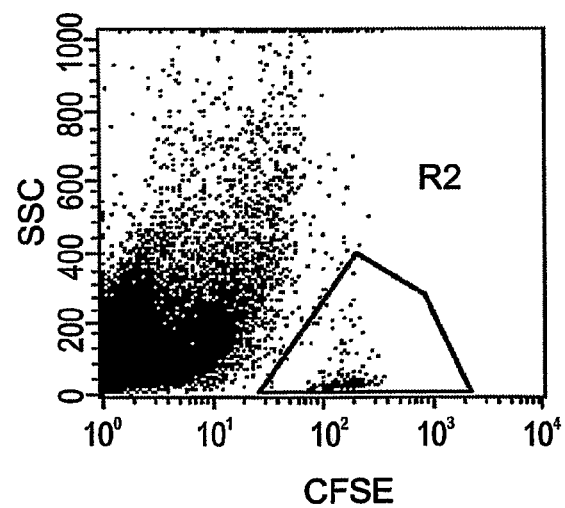
Figure 1F:
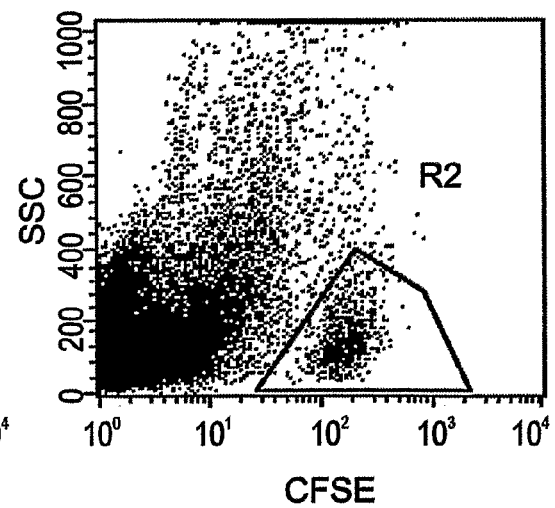
Figure 1G:
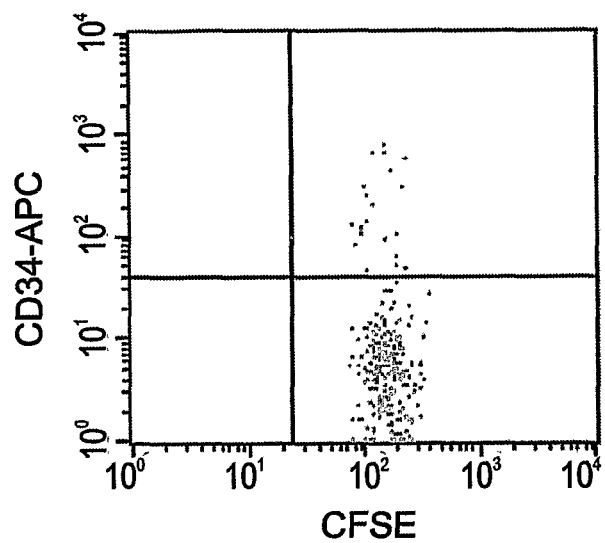
Figure 1H:
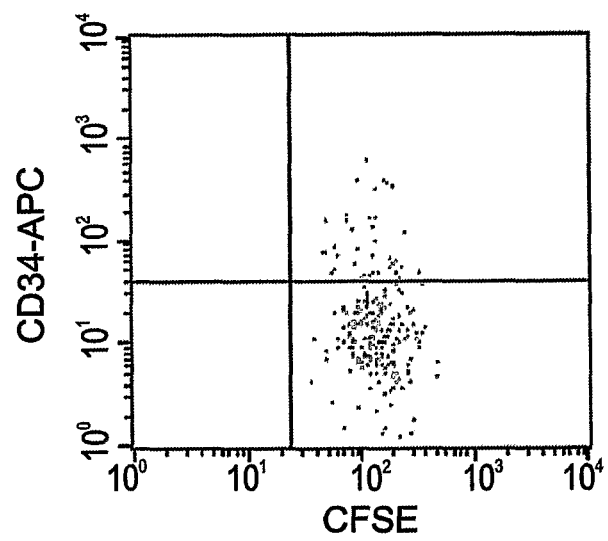
Figure 1I:
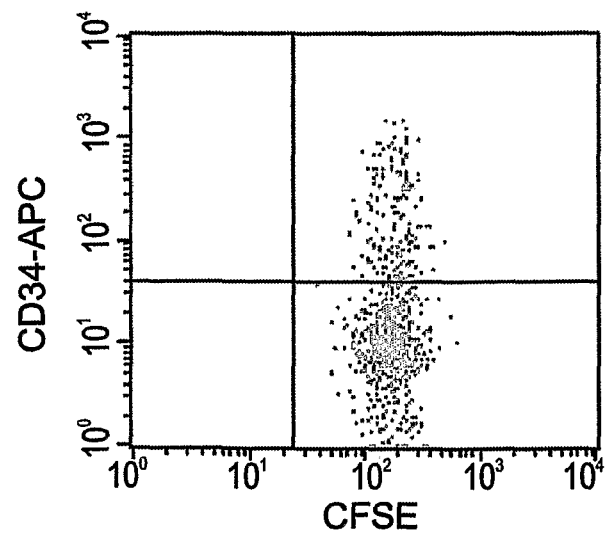

Even though the same number of cells and CD34+ cells were transplanted from both cultured groups, the homing of nicotinamide-treated CD34+ cells was 6-fold higher, while the homing of CD34+ cells without exposure to nicotinamide was only 2-fold higher relative to the homing of non-cultured CD34+ cells (n=21, p<0.05) (FIG. 1a). The homing of cultured cells (MNC) was 2-fold higher with nicotinamide-treated cells compared to nicotinamide-untreated cells, and similar to the homing of non-cultured MNC (n=21, p<0.05) (FIG. 1b). FIGS. 1c-1i show FACS analysis dot plots of representative mice transplanted with non-cultured or cultured cells.

Example 2

Nicotinamide Increases Functionality of Chemokine Receptors and Adhesion Molecules Alterations in chemokine and adhesion molecules, either expression or functionality, have been suggested to cause a homing defect in cultured CD34+ cells, since the binding of cells to specific "docking" ligands is critical for the efficient passage of cells from circulation to target tissues (Foguenne, J., et al. Haematologica, 2005; 90:445-51). This is specially significant in view of the broad distribution of integrins and adhesion molecules such as VLA-4 and LFA-1 across a variety of cell types (muscle cells, lymphocytes, eosinophils, etc). In order to determine the role of such adhesion and related molecules in nicotinamide-mediated enhancement of homing and engraftment of cells, the effect of nicotinamide on in-vitro migration and the functionality of the adhesion molecule Very Late Activation Antigen-4 (VLA-4) was tested.

Figure 2:
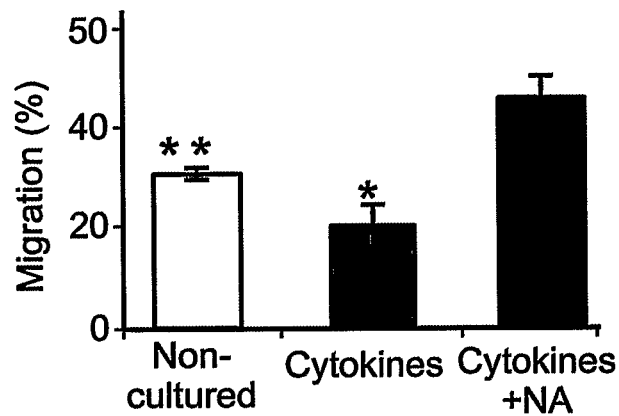
FIG. 2 is a histogram showing the effect of nicotinamide on in-vitro migration of hematopoietic cells. CXCL12 (100 ng/ml)-induced transwell migration of the purified CD34+ cells either before (non-cultured) or after 3-week culture with cytokines and nicotinamide (cytokines+NA) or cytokines alone (cytokines) (n=3, *p<0.02, **p=0.05) was measured as described hereinbelow. Note the enhanced migration of cells cultured in the presence of nicotinamide.

Using a trans-well migration assay, CXCL12-induced migration of non-cultured and cultured hematopoietic cells was tested, assessing the effects of nicotinamide on integrin and adhesion molecule function. CXCL12 powerfully stimulated the migration of both treated and untreated CD34+ cells (FIG. 2d). However, CXCL12-induced migration was significantly higher in cells cultured with nicotinamide (cytokines+NA) compared to the cells cultured without nicotinamide (p>0.02) or non-cultured cells (p=0.05) (FIG. 2). These results suggest that treatment of CD34+ cells with NA can potentially increase the responsiveness of CXCR4 to its ligand CXCL12, resulting in enhanced engraftment and homing potential of the nicotinamide-treated cells.

Figure 3:
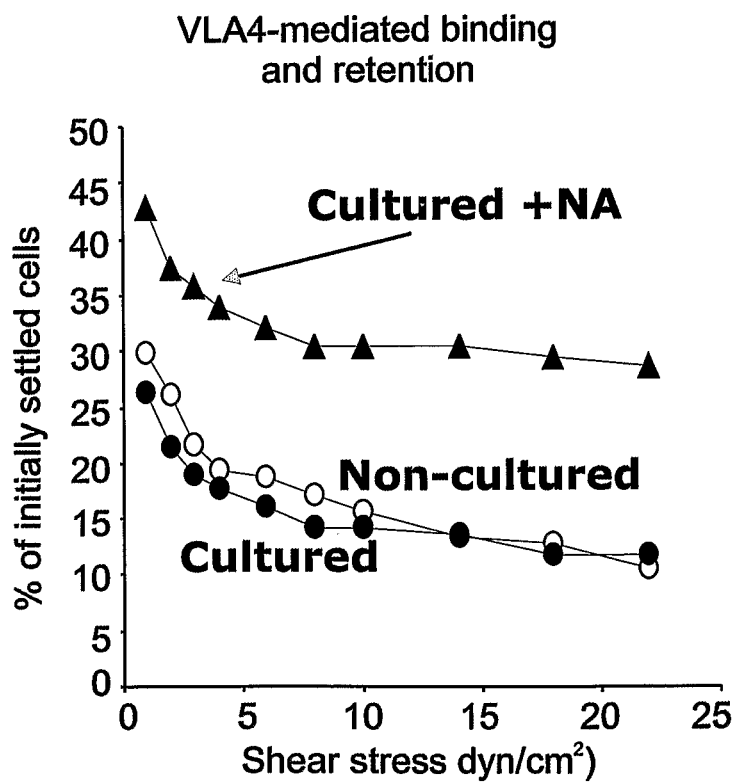
FIG. 3 is a graph showing the effect of nicotinamide on VLA4-mediated binding of cells to immobilized adhesion molecules under shear flow. CD34+ cells cultured as described in FIGS. 1 and 2 hereinabove were assayed for capture and arrest under shear stress, on immobilized VCAM-1 adsorbed as 10 μl dots on polystyrene. Cell settling events, and arrest were analyzed under perfusion (shear stress) by video photography. Assayed cell populations were cells before culture (non-cultured, open circles), cells cultured with cytokines, as described in FIG. 2 (cultured, closed circles), and cells cultured with cytokines and nicotinamide (cultured+NA, closed triangles). Note the significant and consistent effect of nicotinamide on adhesion molecule-mediated binding.

When the functional quality of cell binding to adhesion molecules was investigated using shear flow analysis, the strong effect of nicotinamide on VLA4-mediated binding and retention on VCAM was revealed. FIG. 3 shows the significantly enhanced percentage of initially settled cells resistant to removal by shear stress evident in the cells treated with nicotinamide.

Thus, the results in FIGS. 2 and 3 reveal that nicotinamide treatment of cells before transplantation increases the function of adhesion and cytokine-related molecules in these cells, enhances cell migration, and therefore enhance cell's transplantation potential, as indicated by increased initial capture and binding to immobilized VCAM-1, and retention under increased flow, as compared to non-cultured or cytokines-alone cultured cells.

Example 4

NA Increased the SCID-Repopulating Capacity of Cytokine-Cultured Cells

Figures 4A, 4B, 4C, 4D:
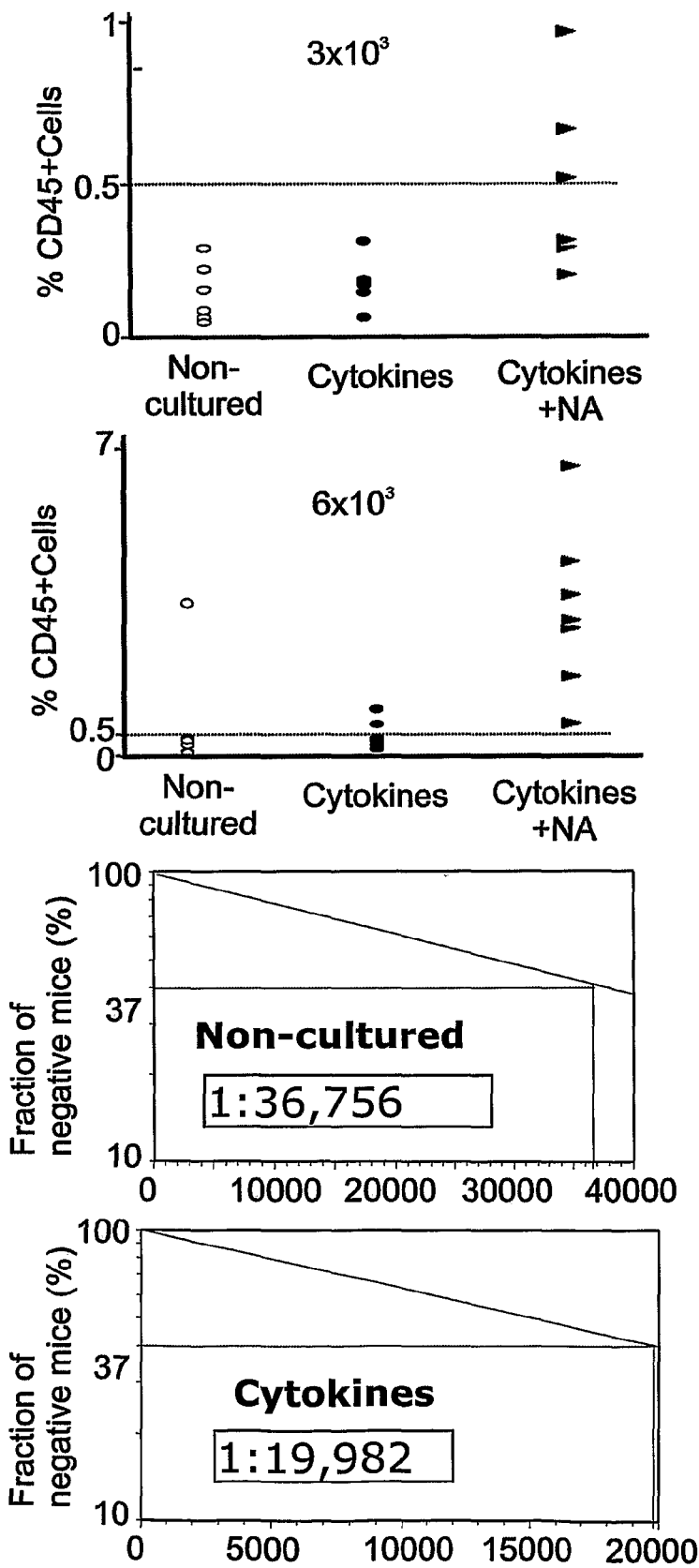
FIGS. 4a-4f is a graphic representation of the effect of nicotinamide on homing and engraftment of human hematopoietic cells transplanted into NOD/SCID mice.

Nicotinamide treatment was tested for ability to enhance homing and engraftment of transplanted cells by repopulation of NOD/SCID mice. To evaluate repopulating capacity, NOD/SCID mice were transplanted with non-cultured CD34$^+$ cells (n=12) over a range of doses intended to achieve a sub-optimal transplantation, and subsequent non-engraftment in a fraction of mice or their progeny following 3-weeks expansion with cytokines (n=12) or cytokines+NA (n=13). Human cell engraftment was evaluated 4-weeks post transplantation. Mice were scored as positively engrafted if 0.5% of the recipient bone marrow cells expressed human CD45 antigen (CD45+). As shown in FIG. 4a, transplantation of $3\times10^3$ CD34$^+$ cells resulted in no engraftment in the non-cultured cells. Similarly, the progeny of $3\times10^3$ CB CD34$^+$ cells cultured with cytokines only also failed to engraft. The presence of nicotinamide in culture, however, resulted in 50% engraftment of $3\times10^3$ CB CD34$^+$ cells in the mice. At a dose range of $6\times10^3$ cells (FIG. 4b), fresh CB CD34$^+$ cells engrafted in only 16.7% of the mice, whereas the progeny of $6\times10^3$ CD34$^+$ cells cultured with cytokines engrafted in 33.3% of the mice. In contrast, at the same dose range, the progeny of cytokines nicotinamide cultured cells engrafted in 100% of the mice (FIG. 4b).

Figure 4E:
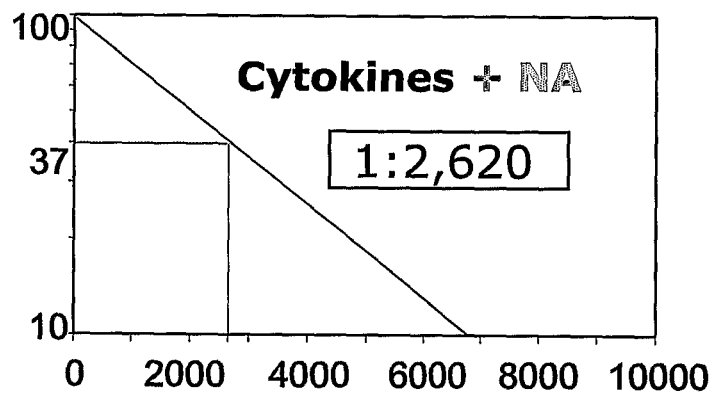
Figure 4F:
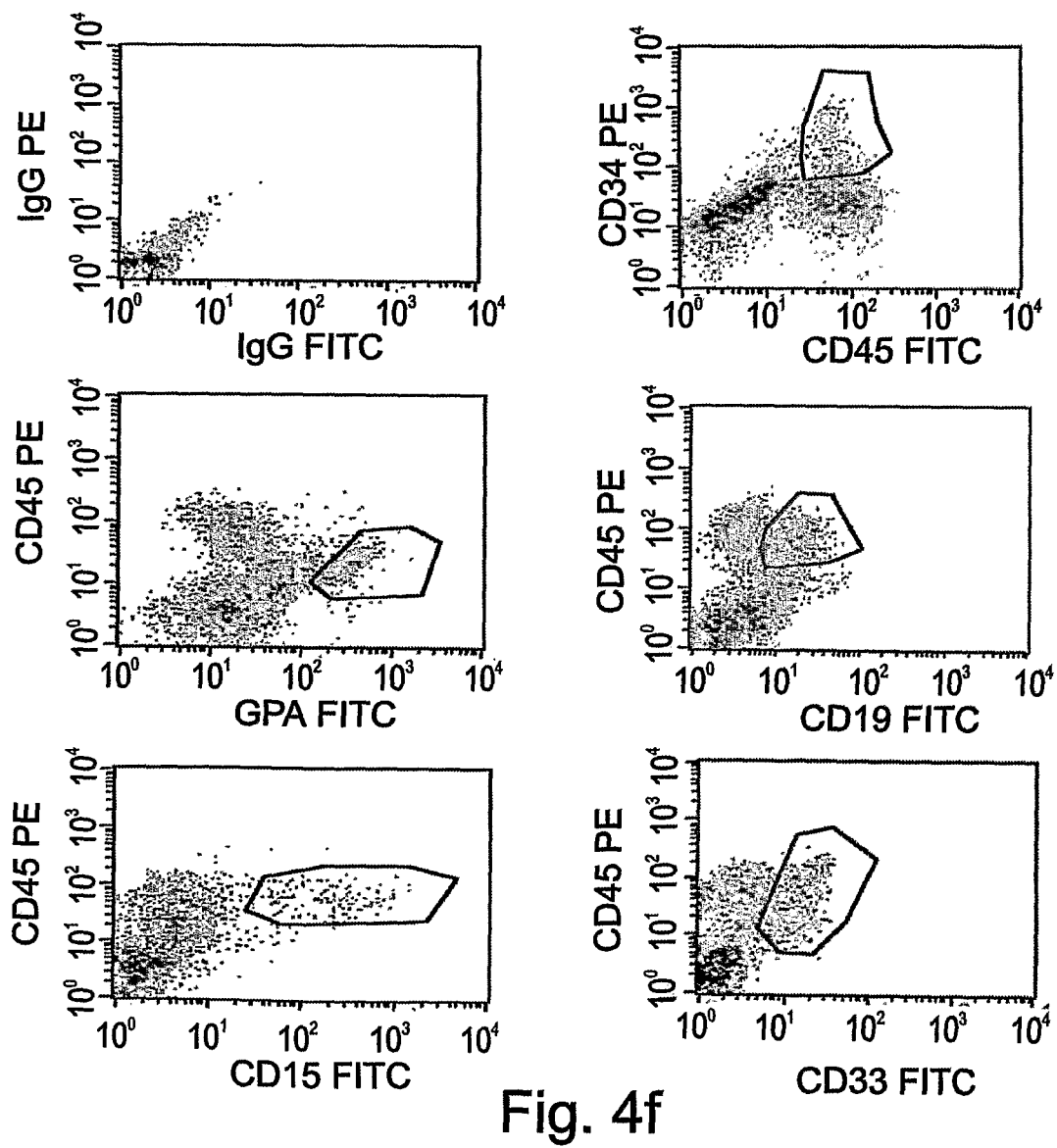

The frequency of SCID repopulating cells (SRCs) was calculated using the maximum likelihood estimator as described hereinabove (FIGS. 4c-4e). The frequency of SRCs within non-cultured CD34$^+$ cells was 1 in 36,756 cells (95% confidence interval [CI], 1/113,366-1/11,917) (FIG. 4c.). The SRC frequency within cells cultured with cytokines alone was 1 in 19,982 (CI, 1/47,972-1/8,323) (FIG. 4d) and the SRC frequency within cells cultured in the presence of nicotinamide and cytokines was significantly higher, at 1 in 2,620 (CI, 1/5,127-1/1,339) (FIG. 4e). Therefore, culture conditions including nicotinamide supported a 14-fold greater number of SRCs than non-cultured cells and 7.6-fold more SRCs than cytokine alone-cultured cells. FIG. 4f demonstrates in vivo multilineage differentiation of NA-treated cultured cells engrafted in NOD/SCID mice.

Figures 5A, 5B, 5C:
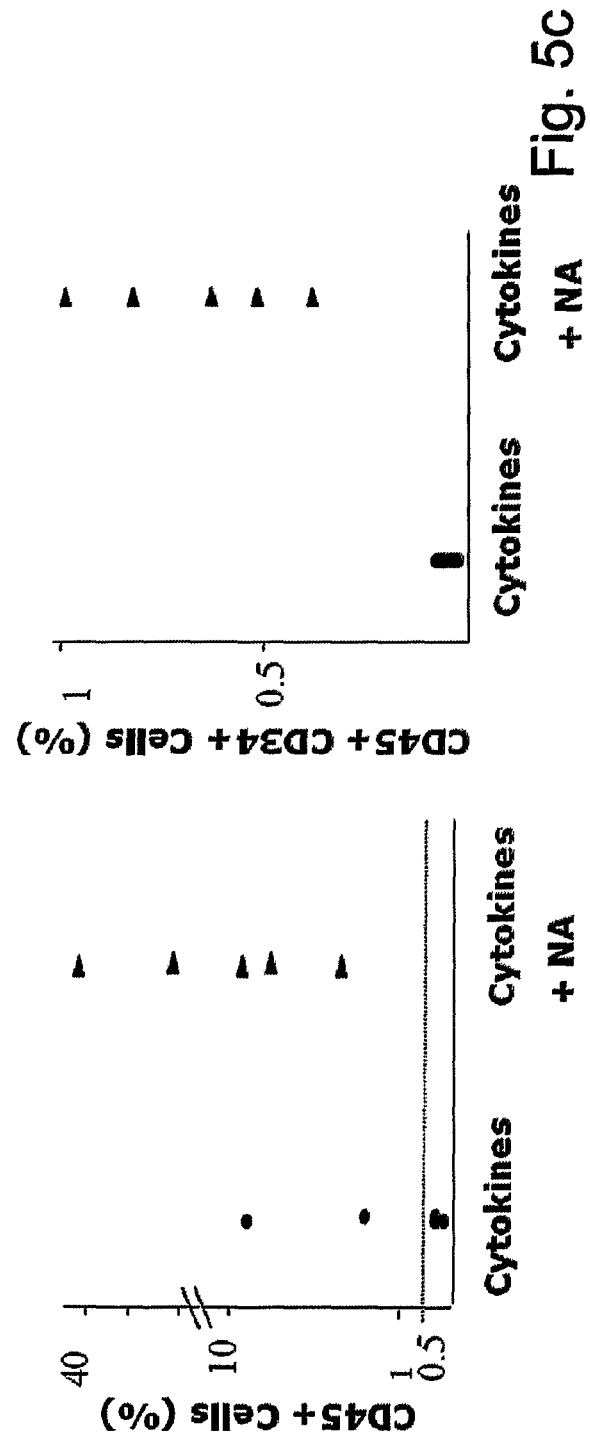
FIGS. 5a-5c are a graphic representation of the effect of nicotinamide (NA) on the engraftment potential of cells cultured under differentiation-promoting conditions. Cultures were initiated with purified cord blood-derived CD34+ cells in medium supplemented with SCF, TPO, IL-6 and FLT3, 50 ng/ml each, and IL-3, 20 ng/ml, with (cytokines+NA, arrows) or without (cytokines, ovals) 10 mM nicotinamide. After 3 weeks, cells were harvested, and transplanted into SCID mice as indicated. Mice were transplanted with $1.25-5 \times 10^4$ CD34+ cells or with their progeny following expansion. Mice were sacrificed 4 weeks later and bone marrow cells were analyzed by FACS for the presence of CD34+ (human progenitor) and CD45+ (human) cells. Mice were scored as engrafted when the number of human (CD45+) cells constituted ≤0.5% of the marrow population.

Effect of Nicotinamide on Homing and Engraftment in IL-3 Treated Cells:

IL-3 has been reported to accelerate differentiation and attenuate SCID repopulating ability of transplanted cells. In order to test whether nicotinamide modulates the engraftment potential of cells exposed to the cytokine, nicotinamide's effect on CB-derived CD34+ cells cultured with IL-3 was assessed. Transplantation experiments indicated that treatment with nicotinamide indeed increased the SCID repopulating potential of IL-3 supplemented cultures. FIG. 5a shows the proportion of engraftment following injection of 1.25 to $5\times10^4$ cells. FIGS. 5b-c exhibits the engraftment of total human cells (FIG. 5b) and progenitor cells (FIG. 5c) following transplantation of the lowest cell dose evaluated in this experiment ($1.25\times10^4$ cells). The results show the presence of human (CD45+) cells in bone marrow of 5 out of 5 mice transplanted with nicotinamide treated cells, but in only 2 out of 5 mice transplanted with cytokine alone treated cells (FIG. 5a). Engraftment of human progenitors (CD45+CD34+) 4-weeks after transplantation was observed only in mice transplanted with cells cultured with nicotinamide.

The results brought hereinabove clearly show that exposure of cells to nicotinamide enhances expression and function of adhesion and integrin molecules critical to cell engraftment and homing, can increase cell migration potential, and clearly provides superior engraftment and homing of transplanted cells. Thus, nicotinamide can be used to provide cell populations for transplantation, having enhanced homing and engraftment potential.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

The teachings of PCT Application IL03/00064, which are hereby incorporated by reference as if fully set forth herein, are intended to be excluded from the scope of the present invention and appending claims.

LIST OF REFERENCES

Aiuti J. Exp. Med. 1997; 185:111-120
Anderlini, P. and Korbling, M. (1997) Stem. Cells 15, 9-17
Baggiolini, M. 1998, Nature 392:565
Banasik M. et al., J Biol Chem. 1992; 267:1569-1575
Bernhard Cancer Res 10: 99, (1995)
Christopherson K W 2nd, et al., Science. 2004 Aug. 13; 305(5686):1000-1003
Christopherson K W 2nd, J Immunol. 2002 Dec. 15; 169(12): 7000-7008
Corda D, Di Girolamo M. 2003; 22(9):1953-1958
de la Cruz X, Lois S, et al., Bioessays. 2005; 27(2):164-75
De Roos et al Transplantation 1997; 63:513-18
Fisch Eur J Immunol 26: 595, (1996)
Foguenne, J., et al. Haematologica, 2005; 90:445-51
Freedman Nature Medicine 2: 46, (1996)
Gagandeep et al, Gene Therapy 1999; 6:729-36
Heslop Nature Medicine 2: 551, (1996)
Humeau L., et al Blood (1997) 90:3496
Ito et al, Muscle Nerve 1998; 21:291-7
Imai Br. J. Haematol. 1999; 106:905-911
Jaime Imitola et al., Proc Natl Acad Sci USA. 2004 101(52): 18117-18122
Kipshidze and Serruys, eds. London, UK, 2004
Lupi R, et al., J Biol Chem. 2000; 275:9418-9424
Lupi R, et al. Biochem J. 2002:367:1-7
McGrath Dev. Biol. 1999; 213:442-456
Protti Cancer Res 56: 1210, (1996)
Rankin P W, et al., J Biol Chem. 1989; 264:4312-4317
Roach M L. Methods Mol Biol (2002) 185: 1
Siena Expt Hematol 23:1463, (1996)
Shioda et al. (1998) Proc. Natl. Acad. Sci. USA 95:6331
Smith A G. Annu Rev Cell Dev Biol (2001) 17:435
Smith S. Trends Biochem Sci. 2001; 26:174-179
Trounson A O. Reprod Fertil Dev (2001) 13: 523
Ueda K, Hayaishi O, Annu Rev Biochem. 1985; 54:73-100
Virág L, Szabó C. Pharm. Reviews. 2002; 54:375-429
Yau L, et al., Eur. J. Biochem. 2003; 270:101-110

What is claimed is:

1. A method of enhancing cell homing and engraftment potential, the method comprising ex-vivo or in vitro culturing a population of isolated CD34+ hematopoietic stem cells in the presence of 1 to 10 mM nicotinamide for a period of time of 5-30 hours, wherein said period of time is insufficient for proliferation of said isolated CD34+ hematopoietic stem cells, and wherein said culturing results in down-regulation of CD26 expression as compared to isolated CD34+ hematopoietic stem cells cultured in the absence of nicotinamide.

2. The method of claim 1, wherein said nicotinamide is selected from the group consisting of nicotinamide, a nicotinamide analog, a nicotinamide metabolite, a nicotinamide analog metabolite and derivatives thereof.

3. The method of claim 1, wherein said population of CD34+ hematopoietic stem cells is from a source selected from the group consisting of umbilical cord blood cells, mobilized peripheral blood cells, and bone marrow cells.

4. The method of claim 1, wherein said population of CD34+ hematopoietic stem cells is from bone marrow or peripheral blood.

5. The method of claim 1, wherein said population of CD34+ hematopoietic stem cells is from neonatal umbilical cord blood.

6. The method of claim 1, wherein said population of CD34+ hematopoietic stem cells is from a mononuclear cell fraction.

7. The method of claim 1, further comprising the step of selecting a population of cells enriched for hematopoietic stem cells via CD34 prior to, concomitant with or following said step of ex-vivo culturing.

8. The method of claim 7, wherein said selecting is effected via CD133.

9. The method of claim 7, wherein said selecting is effected via CD34/CD38.

10. The method of claim 1, wherein said population of cells is cultured in 5 mM nicotinamide for 20 hours.

* * * * *

UNITED STATES PATENT AND TRADEMARK OFFICE
CERTIFICATE OF CORRECTION

| | | |
|---|---|---|
| PATENT NO. | : 8,846,393 B2 | Page 1 of 1 |
| APPLICATION NO. | : 12/085406 | |
| DATED | : September 30, 2014 | |
| INVENTOR(S) | : Peled | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1186 days.

Signed and Sealed this
Fifteenth Day of September, 2015

Michelle K. Lee
*Director of the United States Patent and Trademark Office*